United States Patent
Li et al.

(10) Patent No.: US 11,167,000 B2
(45) Date of Patent: Nov. 9, 2021

(54) USES AND DEVELOPMENT OF NEURODEFEND FOR TREATING NEURODEGENERATIVE DISEASES

(71) Applicant: Hong Kong Baptist University, Hong Kong (HK)

(72) Inventors: Min Li, Hong Kong (HK); Ashok Iyaswamy, Hong Kong (HK); Siva Sundara Kumar Durairajan, Thiruvarur (IN); Senthilkumar Krishnamoorthi, Hong Kong (HK); Huan Zhang, Hong Kong (HK); Sravan G. S. Sreenivasamurthy, Hong Kong (HK)

(73) Assignee: Hong Kong Baptist University, Hong Kong (HK)

( * ) Notice: Subject to any disclaimer, the term of this patent is extended or adjusted under 35 U.S.C. 154(b) by 420 days.

(21) Appl. No.: 16/219,976

(22) Filed: Dec. 14, 2018

(65) Prior Publication Data

US 2019/0282646 A1    Sep. 19, 2019

Related U.S. Application Data

(60) Provisional application No. 62/643,774, filed on Mar. 16, 2018.

(51) Int. Cl.
| | |
|---|---|
| *A61K 36/505* | (2006.01) |
| *A61P 25/28* | (2006.01) |
| *A61K 36/718* | (2006.01) |
| *A61K 9/00* | (2006.01) |
| *A61K 36/74* | (2006.01) |
| *A61K 36/537* | (2006.01) |

(52) U.S. Cl.
CPC .......... *A61K 36/505* (2013.01); *A61K 9/0053* (2013.01); *A61K 36/537* (2013.01); *A61K 36/718* (2013.01); *A61K 36/74* (2013.01); *A61P 25/28* (2018.01)

(58) Field of Classification Search
CPC .... A61K 2300/00; A61K 36/31; A61K 36/48; A61K 36/704; A61K 2800/92; A61K 8/9789; A23V 2002/00; A23V 2200/318; A23V 2250/21; A23L 11/05; A23L 33/105; A61P 17/14; A61Q 7/00
See application file for complete search history.

(56) References Cited

U.S. PATENT DOCUMENTS

2009/0104295 A1* 4/2009 Kohno ................... A61K 36/31
424/757

OTHER PUBLICATIONS

Durairajan SSK, Ashok I, Sravan GS, Ananth KK, Sandeep M, Wenbin S, Chuanbin Y, Juxian S, Sookja C, Huang J, Ilango K, Han QB & Li M. A modified formulation of Huanglian-Jie-Du-Tang reduces memory impairments and β-amyloid plaques in a triple transgenic mouse model of Alzheimer's disease, Sci Rep 2017;7: 6238. p. 1-13.

* cited by examiner

*Primary Examiner* — Aaron J Kosar
(74) *Attorney, Agent, or Firm* — Idea Intellectual Limited; Margaret A. Burke; Sam T. Yip

(57) ABSTRACT

A herbal composition with significant potent therapeutic effects for treating neurodegenerative diseases by targeting both amyloid-β (Aβ) and tau-associated neurofibrillary tangles (NFTs) is provided.

16 Claims, 74 Drawing Sheets

LD₅₀ of ND23

| Group | Dose (g/kg) | | Death | | |
|---|---|---|---|---|---|
| 1 | 80 | - | 0 | 0 | 0 |
| 2 | 40 | 40 | 0 | 0 | 0 |
| 3 | 20 | 20 | 0 | 0 | 0 |
| 4 | 10 | 10 | 0 | 0 | 0 |
| 5 | 5 | 5 | 0 | 0 | 0 |

$LD_{50} = 80-(0/4) = 80$ g/kg

LD$_{50}$ of ND15

| Group | Dose (g/kg) | Dose difference (g/kg) | Dead | Mean d | Product A·D |
|---|---|---|---|---|---|
| 1 | 80 | 0 | 1 | 0.5 | 0 |
| 2 | 40 | 40 | 0 | 0 | 0 |
| 3 | 20 | 20 | 0 | 0 | 0 |
| 4 | 10 | 10 | 0 | 0 | 0 |
| 5 | 5 | 5 | 0 | 0 | 0 |

$LD_{50} = 80-(0/4) = 80$ g/kg

| Biochemical constituents | WT_Vehicle | ND1_1.9 g/kg | ND1_3.8 g/kg | ND1_7.6 g/kg |
|---|---|---|---|---|
| ALT/GPT(IU/L) | 18.14±2.89 | 15.33±5.03 | 17.30±3.08 | 16.93±3.14 |
| AST/GOT(IU/L) | 23.99±3.72 | 23.68±3.51 | 22.65±3.18 | 25.08±2.64 |
| BUN(mM) | 11.72±0.88 | 10.44±0.43 | 11.87±1.03 | 11.31±0.65 |
| Cr(μM) | 36.89±4.29 | 39.64±1.36 | 38.65±3.58 | 36.45±3.64 |
| T-BIL(μM/L) | 1.73±0.00 | 1.73±0.00 | 1.73±0.00 | 1.73±0.00 |
| Na(mM/L) | 102.80±15.20 | 104.28±1.93 | 107.66±3.09 | 102.74±4.95 |
| Γ-GT(U/L) | 11737.2±0 | 127028.2±6639 | 120387.2±0 | 120387.2±8852 |
| ALB(g/L) | 27.37±3.40 | 26.51±2.50 | 27.72±1.05 | 28.36±4.32 |
| ALP(KU/100ml) | 23.02±1.24 | 25.99±1.10 | 26.27±7.81 | 24.57±5.85 |
| K(mM) | 5.89±0.99 | 4.90±0.29 | 5.52±0.32 | 5.93±0.32 |
| Cl(mM) | 63.37±0.75 | 62.54±0.48 | 63.36±0.46 | 62.58±0.39 |
| TC(mM) | 2.38±0.30 | 2.28±0.53 | 1.93±0.72 | 1.91±0.32 |
| TG(mM) | 0.15±0.03 | 0.15±0.03 | 0.14±0.02 | 0.16±0.03 |

Figure 30A

| Biochemical constituents | WT_Vehicle | ND23_1.9 g/kg | ND23_3.8 g/kg | ND23_7.6 g/kg |
|---|---|---|---|---|
| ALT/GPT(IU/L) | 18.33±1.61 | 15.96±1.29 | 17.93±3.89 | 16.71±4.96 |
| AST/GOT(IU/L) | 19.62±3.45 | 18.45±0.33 | 20.46±1.01 | 21.50±1.60 |
| BUN(mM) | 11.70±1.96 | 9.11±0.32 | 11.34±0.78 | 10.16±0.60 |
| Cr(μM) | 35.28±4.48 | 34.86±4.23 | 34.55±4.45 | 39.80±5.98 |
| T-BIL(μM/L) | 0.84±0 | 0.84±0 | 0.89±0.44 | 0.84±0 |
| Na(mM/L) | 110.68±5.79 | 111.57±4.57 | 120.95±7.80 | 121.69±16.04 |
| Γ-GT(U/L) | 11950.2±2213 | 12163.2±6259.31 | 11950.2±2213 | 11950.2±2213 |
| ALB(g/L) | 29.52±2.14 | 28.29±1.63 | 28.47±4.56 | 31.13±4.78 |
| ALP(KU/100ml) | 18.46±2.42 | 16.73±2.27 | 17.97±4.28 | 18.05±3.14 |
| K(mM) | 5.21±0.41 | 5.22±0.30 | 5.45±0.38 | 5.96±0.28 |
| Cl(mM) | 63.20±0.66 | 62.17±0.13 | 62.86±0.52 | 62.76±0.40 |
| TC(mM) | 2.12±0.31 | 2.19±0.38 | 1.95±0.77 | 2.04±0.37 |
| TG(mM) | 0.14±0.00 | 0.14±0.04 | 0.15±0.01 | 0.15±0.03 |

Figure 30B

| Biochemical constituents | WT_Vehicle | ND15_1.9 g/kg | ND15_3.8 g/kg | ND15_7.6 g/kg |
|---|---|---|---|---|
| ALT/GPT(IU/L) | 13.01±3.21 | 13.80±4.31 | 13.84±2.56 | 13.78±1.38 |
| AST/GOT(IU/L) | 18.88±2.68 | 19.71±5.94 | 17.53±1.73 | 19.40±2.17 |
| BUN(mM) | 14.77±2.75 | 15.41±1.64 | 14.07±1.73 | 13.02±1.22 |
| Cr(μM) | 36.89±4.29 | 39.64±1.36 | 38.65±3.58 | 38.45±3.36 |
| T-BIL(μM/L) | 3.18±0.44 | 2.62±0 | 3.21±0 | 3.06±0.44 |
| Na(mM/L) | 113.53±6.91 | 111.67±2.67 | 116.95±9.39 | 112.84±5.82 |
| Γ-GT(U/L) | 6311.2±0 | 6417.7±1106.5 | 6786.53±1043.2 | 6311.2±0 |
| ALB(g/L) | 27.37±3.40 | 26.51±2.50 | 27.72±1.05 | 28.36±4.32 |
| ALP(KU/100ml) | 5.46±0.43 | 5.62±0.75 | 5.35±1.63 | 5.73±1.10 |
| K(mM) | 5.73±0.61 | 5.82±0.40 | 5.91±0.45 | 5.37±0.12 |
| Cl(mM) | 69.59±0.75 | 70.92±1.96 | 70.31±0.78 | 71.00±0.86 |
| TC(mM) | 1.84±0.18 | 1.73±0.19 | 1.72±0.17 | 1.95±0.64 |
| TG(mM) | 0.30±0.05 | 0.30±0.05 | 0.35±0.01 | 0.22±0.05 |

Figure 30C

USES AND DEVELOPMENT OF NEURODEFEND FOR TREATING NEURODEGENERATIVE DISEASES

CROSS REFERENCE OF RELATED APPLICATION

This application is a non-provisional application which claims priority to U.S. Provisional Patent Application Ser. No. 62/643,774 filed Mar. 16, 2018, which is hereby incorporated by reference in its entirety.

FIELD OF INVENTION

This invention relates to the field of pharmaceuticals, health supplements and industrial chemical products. In particular, this invention provides herbal composition for treating neurodegenerative diseases by targeting both amyloid-β (Aβ) and tau-associated neurofibrillary tangles (NFTs).

BACKGROUND OF INVENTION

Alzheimer disease (AD) is a common neurodegenerative disorder mostly affecting the aged population and a complete cure does not appear to be available. AD is the most common brain disease in the world which affects 4-8% of the elderly population worldwide. Prevalence studies indicate that the global Alzheimer's disease (AD) population will proliferate to 114 million by 2050. In Hong Kong alone the prevalence of mild dementia is 17.5% in total population. Currently, AD drugs in the market are rudimentary. Existing drugs can only relieve certain symptoms but they cannot cure the disease. As such, effective and safe drugs are the need of the hour for the complete cure of AD.

The key hallmark features of AD are: loss of cholinergic neurons; formation of senile plaques (SP) by accumulation of amyloid β-peptide (Aβ) derived from amyloid precursor protein (APP); and formation of tau-associated neurofibrillary tangles (NFTs). Neurodegenerative diseases with tau inclusions are denoted as tauopathy. In AD, Aβ and NFTs are well correlated with cognitive impairment, tackling Aβ and NFTs now seems to be the strategy that is most likely to succeed since combination therapy has been reported to be beneficial in treating AD. The inventors' previous work has showed that modified HLJDT (i.e., HLJDT without Huangqin: HLJDT-M) has positive activity compared to the classic formula HLJDT in reducing the amyloid-β (Aβ) load in both in vitro and in vivo. Although HLJDT-M shows a Aβ-reducing effect, it does not have a Tau-reducing effect and hence, there is a dire need to optimize HLJDT-M for AD treatment.

Citation or identification of any reference in this section or any other section of this application shall not be construed as an admission that such reference is available as prior art for the present application.

SUMMARY OF INVENTION

Accordingly, the objective of the invention is to provide herbal composition with significant potent therapeutic effects for treating neurodegenerative diseases by targeting both amyloid-β (Aβ) and tau-associated neurofibrillary tangles (NFTs).

The first aspect of the present invention provides a herbal composition comprising a herbal extract of Huanglian, Huangbai, ZhiZi, Yanhusuo, Danshen and Gouteng.

In one embodiment of the first aspect of the present invention, the herbal extract comprises Huanglian, Huangbai, ZhiZi, Yanhusuo, Danshen and Gouteng in the weight ratio of 0.83-4.15:1.66-3.46:1.53-4.16:2.69-2.91: 4.57-6.22:4.22-6.24.

In one embodiment of the first aspect of the present invention, the herbal extract comprises Huanglian, Huangbai, ZhiZi, Yanhusuo, Danshen and Gouteng in a weight ratio of 0.83:1.66:4.16:2.91:4.57:6.24.

In one embodiment of the first aspect of the present invention, the herbal extract comprises Huanglian, Huangbai, ZhiZi, Yanhusuo, Danshen and Gouteng in a weight ratio of 4.15:3.46:3.46:2.76:6.22:6.22.

In one embodiment of the first aspect of the present invention, the herbal extract comprises Huanglian, Huangbai, ZhiZi, Yanhusuo, Danshen and Gouteng in a weight ratio of 3.45:1.92:1.53:2.69:5.76:4.22.

A second aspect of the present invention provides use of the herbal composition in the manufacture of a pharmaceutical composition for treating neurodegenerative diseases caused by amyloid-β (Aβ) and tau-associated neurofibrillary tangles.

A third aspect of the present invention provides method of treating neurodegenerative diseases caused by amyloid-β (Aβ) and tau-associated neurofibrillary tangles in human by administering the herbal composition in a dosage from 0.154 g/kg/day to 0.617 g/kg/day.

In one embodiment of the second and third aspect of the present invention, the herbal composition is administered orally.

In one embodiment of the second and third aspect of the present invention, the neurodegenerative diseases caused by amyloid-β (Aβ) and tau-associated neurofibrillary tangles in human comprising Alzheimer's disease.

Throughout this specification, unless the context requires otherwise, the word "include" or "comprise" or variations such as "includes" or "comprises" or "comprising", will be to imply the inclusion of a stated integer or group of integers but not the exclusion of any other integer or group of integers. It is also noted that in this disclosure and particularly in the claims and/or paragraphs, terms such as "included", "comprises", "comprised", "comprising" and the like shall have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the present invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the present invention and apply throughout. Unless otherwise defined, all other technical terms used herein have the same meaning as commonly understood to one of ordinary skill in the art to which the present invention belongs.

Other aspects and advantages of the present invention will be apparent to those skilled in the art from a review of the ensuing description.

BRIEF DESCRIPTION OF DRAWINGS

The above and other objects and features of the present invention will become apparent from the following description of the present invention, when taken in conjunction with the accompanying drawings, in which:

FIG. 8I1 shows the time line for ND treatment and behavior experiments schedule in 5XFAD mice.

FIG. 30A shows quantified results of the biochemical constituents of the blood plasma of ND1 (1.9, 3.8, 7.6 g/kg/day) treated groups were assessed and tabulated in the table.

FIG. 30B shows quantified results of the biochemical constituents of the blood plasma of ND23 (1.9, 3.8, 7.6 g/kg/day) treated groups were assessed and tabulated in the table.

FIG. 30C shows quantified results of the biochemical constituents of the blood plasma of ND15 (1.9, 3.8, 7.6 g/kg/day) treated groups were assessed and tabulated in the table.

FIG. 31A shows the quantitative analysis of the ND1 treated 3XTg-AD animal. Iba1 burden were assessed by Image J software.

FIG. 31B shows fluorescence images showing ND1 (1.9, 3.8, 7.6 g/kg/day) reduces the Iba1 positive cell load in 3XTg-AD mice by immunohistochemistry.

FIG. 32A shows the quantitative analysis of the ND23 treated 3XTg-AD animal. Iba1 burden were assessed by Image J software.

FIG. 32B shows fluorescence images showing ND23 (1.9, 3.8, 7.6 g/kg/day) reduces the Iba1 positive cell load in 3XTg-AD mice by immunohistochemistry.

FIG. 33A shows the quantitative analysis of the ND15 treated 3XTg-AD animal. Iba1 burden were assessed by Image J software.

FIG. 33B shows fluorescence images showing ND15 (1.9, 3.8, 7.6 g/kg/day) reduces the Iba1 positive cell load in 3XTg-AD mice by immunohistochemistry.

FIG. 34A shows the quantitative analysis of the ND1 treated 5XFAD animal. GFAP burden were assessed by Image J software.

FIG. 34B shows the quantitative analysis of the ND1 treated 5XFAD animal. Iba1 burden were assessed by Image J software.

FIG. 34C shows fluorescence images showing ND1 (1.9 and 3.8 g/kg/day) reduces the GFAP and Iba1 positive cell load in 5XFAD mice by immunohistochemistry.

FIG. 35A shows the quantitative analysis of the ND23 treated 5XFAD animal. GFAP burden were assessed by Image J software.

FIG. 35B shows the quantitative analysis of the ND23 treated 5XFAD animal. Iba1 burden were assessed by Image J software.

FIG. 35C shows fluorescence images showing ND23 (3.8 and 7.6 g/kg/day) reduces the GFAP and Iba1 positive cell load in 5XFAD mice by immunohistochemistry.

DETAILED DESCRIPTION OF THE INVENTION

The present invention is further illustrated by the following embodiments and examples which may only be used for illustrative purpose but are not intended to limit the scope of the presently-claimed invention.

Figure 1A:
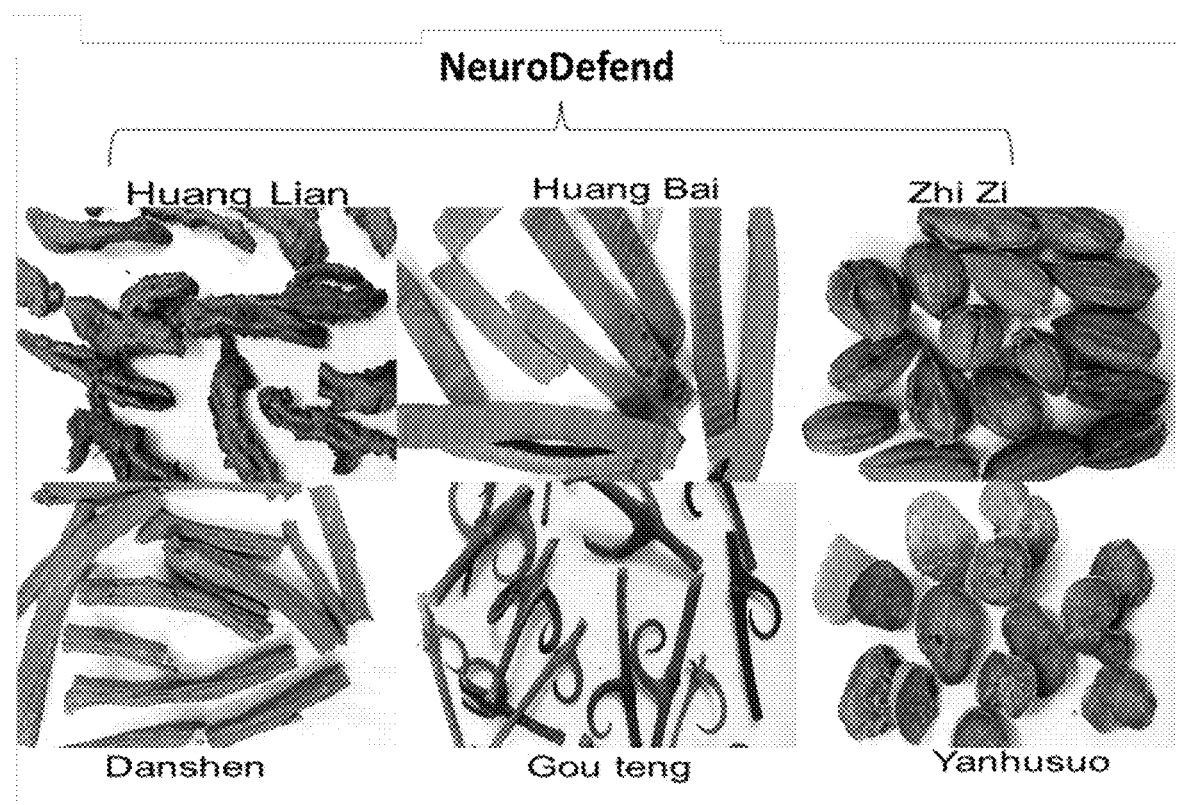
FIG. 1A shows the parts of herbs used for the preparation of the herbal extract of composition of the present invention (NeuroDefend (ND)).

The present invention provides a formulation based on traditional Chinese medicine for the treatment or prevention of neurodegenerative diseases. The inventors' results show that NeuroDefend (ND), a herbal extract, using Uniform design to target Aβ and NFTs would be the novel approach for treating AD. The present invention provides ND, a extract of a herbal combination at key weight ratios which is shown to be an effective therapeutic strategy for ameliorating and treating AD. The term "herbal combination" herein refer to a mixture of dry Huanglian, Huangbai, Zhizi, Danshen, Gouteng and Yanhusuo. The term "herbal extract" herein refers to the extract of the herbal combination in herbal powder form obtained through water decoction of the dry herb, steeping in alcohol and lyophilization. The herbal extract of the present invention can be formulated into other forms for different administration purposes. Even though all of the above medicinal plants have been separately utilized in traditional Chinese medicines for the treatment of variety of neural diseases, it has not been previously disclosed that the active components mentioned above in combination would produce a composition with the noteworthy synergistic therapeutic effects in treating neurodegenerative diseases. The present invention provides a new non-toxic highly effective therapeutic composition in treating neural diseases occurred either individually or associated with other diseases or conditions. The therapeutic composition comprises a extract of the herbal combination (ND) consisting of Huanglian, Huangbai, Zhizi, Danshen, Gouteng and Yanhusuo (FIG. 1A). The extract of the herbal combination contains new and biologically active components. The new and biologically active components in the herbal extract of the present invention refer to biologically active chemical components that are formed during extraction of the herbal combination and are not naturally and originally found in the individual herbs of the herbal combination. As such, the resultant chemical components in the herbal extract of the present invention lead to enhanced therapeutic properties that is different from the herbs could exhibit have the herbs not been combined in the way the present invention provides. In one embodiment, the herbal extract comprises Huanglian, Huangbai, ZhiZi, Yanhusuo, Danshen and Gouteng in the weight ratio of 0.83-4.15:1.66-3.46:1.53-4.16:2.69-2.91:4.57-6.22:4.22-6.24. In one embodiment, the herbal extract comprises Huanglian, Huangbai, ZhiZi, Yanhusuo, Danshen and Gouteng in a weight ratio of 0.83:1.66:4.16:2.91:4.57:6.24. In one embodiment, the herbal extract comprises Huanglian, Huangbai, ZhiZi, Yanhusuo, Danshen and Gouteng in a weight ratio of 4.15:3.46:3.46:2.76:6.22:6.22. In one embodiment, the herbal extract comprises Huanglian, Huangbai, ZhiZi, Yanhusuo, Danshen and Gouteng in a weight ratio of 3.45:1.92:1.53:2.69:5.76:4.22. The weight ratio of the herbs refers to the weight ratio in the herbs in the herbal extract. It is understood that the weight ratio of the herbs in the herbal extract and the herbal combination are maintained. The present composition is relatively inexpensive, highly effective and of low toxicity. The present invention provides 24 herbal extracts (namely ND preparations, ND1 to ND24) as shown in Table 1. ND1, ND23 and ND15 reduce the accumulation of abnormal β-amyloid precursor protein (APP), its C-terminal fragments (CTFs) and phosphorylated Tau—all of which are neuroprotective targets in a cell model of AD. In the animal experiments, it is demonstrated that the present composition is not toxic up to 76 to 80 g/kg/day as inferred from the acute and sub-chronic toxicity experiments. The present invention is shown to be orally bio available and brain permeable in mice. ND1 and ND23 reduce the accumulation of abnormal APP, its CTFs and senile plaques in 5XFAD transgenic AD mice. Further, it is shown that ND1, ND15 and ND23 improve the hippocampal dependent memory, learning and memory retention in 3XTg triple transgenic AD mice. These ND preparations are useful for preventing or treating the diseases related to neuronal loss. The ND preparations and pure compounds contained therein will then be systematically screened in silico and tested in cellular and animal models of AD. The most potent compound(s) will be chosen for the next stage of new drug development of neurodegenerative diseases. The present invention provides three compositions in order to vary the potency for AD mice in different stages of the illnesses noted above. These compositions have been designated ND1, ND15 and ND23. ND15 is the strongest, most effective formula and thus is suitable for clearing Aβ and Tau pathological symptoms. ND23 has moderate potency particularly adapted for use on symptoms of a general nature. ND1 is a mild version especially suitable for long-term care and preventive purposes.

| Group | X1: Huanglian | X2: Hunagbai | X3: ZhiZi | X4: Yanhusuo | X5: Danshen | X6: Gouteng | Total weight in g |
|---|---|---|---|---|---|---|---|
| 1 | 2 | 4 | 10 | 7 | 11 | 15 | 49 |
| 2 | 2 | 6 | 5 | 9 | 12 | 8 | 42 |
| 3 | 2 | 9 | 7 | 5 | 9 | 11 | 43 |
| 4 | 3 | 8 | 4 | 4 | 13 | 13 | 45 |
| 5 | 3 | 4 | 3 | 3 | 8 | 12 | 33 |
| 6 | 3 | 10 | 9 | 8 | 15 | 9 | 54 |
| 7 | 4 | 7 | 6 | 8 | 10 | 13 | 48 |
| 8 | 4 | 5 | 9 | 10 | 8 | 14 | 50 |
| 9 | 4 | 3 | 8 | 6 | 13 | 8 | 42 |
| 10 | 5 | 6 | 10 | 5 | 14 | 10 | 50 |
| 11 | 5 | 10 | 5 | 6 | 12 | 14 | 52 |
| 12 | 5 | 3 | 4 | 10 | 10 | 10 | 42 |
| 13 | 6 | 8 | 8 | 10 | 13 | 11 | 56 |
| 14 | 6 | 7 | 7 | 3 | 15 | 15 | 53 |
| 15 | 6 | 5 | 5 | 4 | 9 | 9 | 38 |
| 16 | 7 | 9 | 10 | 9 | 9 | 13 | 57 |
| 17 | 7 | 4 | 6 | 8 | 14 | 13 | 52 |
| 18 | 7 | 7 | 3 | 6 | 11 | 9 | 43 |
| 19 | 8 | 3 | 9 | 4 | 12 | 12 | 48 |
| 20 | 8 | 9 | 3 | 9 | 14 | 15 | 58 |
| 21 | 8 | 8 | 7 | 7 | 8 | 8 | 46 |
| 22 | 9 | 10 | 6 | 3 | 11 | 10 | 49 |
| 23 | 9 | 5 | 4 | 7 | 15 | 11 | 51 |
| 24 | 9 | 6 | 8 | 5 | 10 | 14 | 52 |

Table 1 shows 24 herbal extracts of the present invention.

Figure 1B:
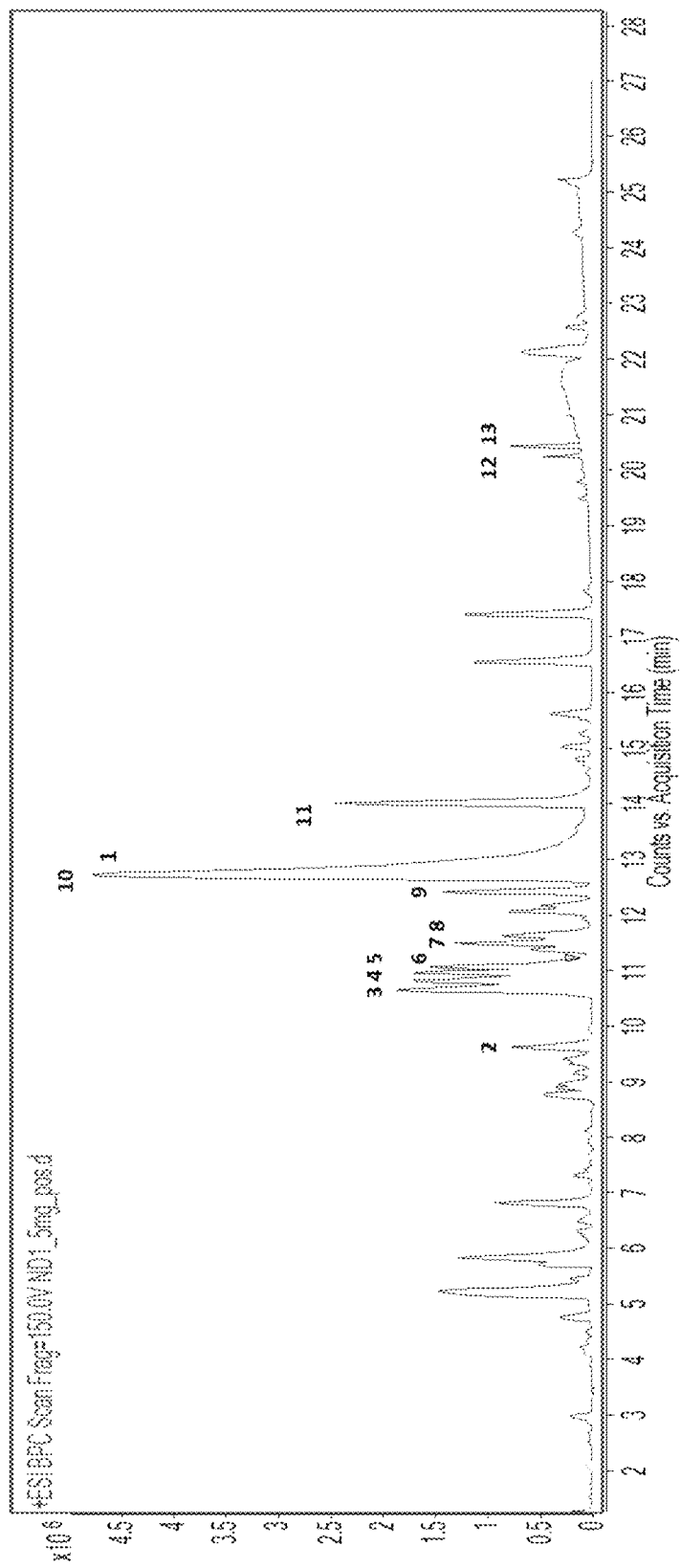
FIG. 1B shows the bioactive components in ND1 determined by LC-ESI-Q/TOF chromatograms.
Figure 1C:
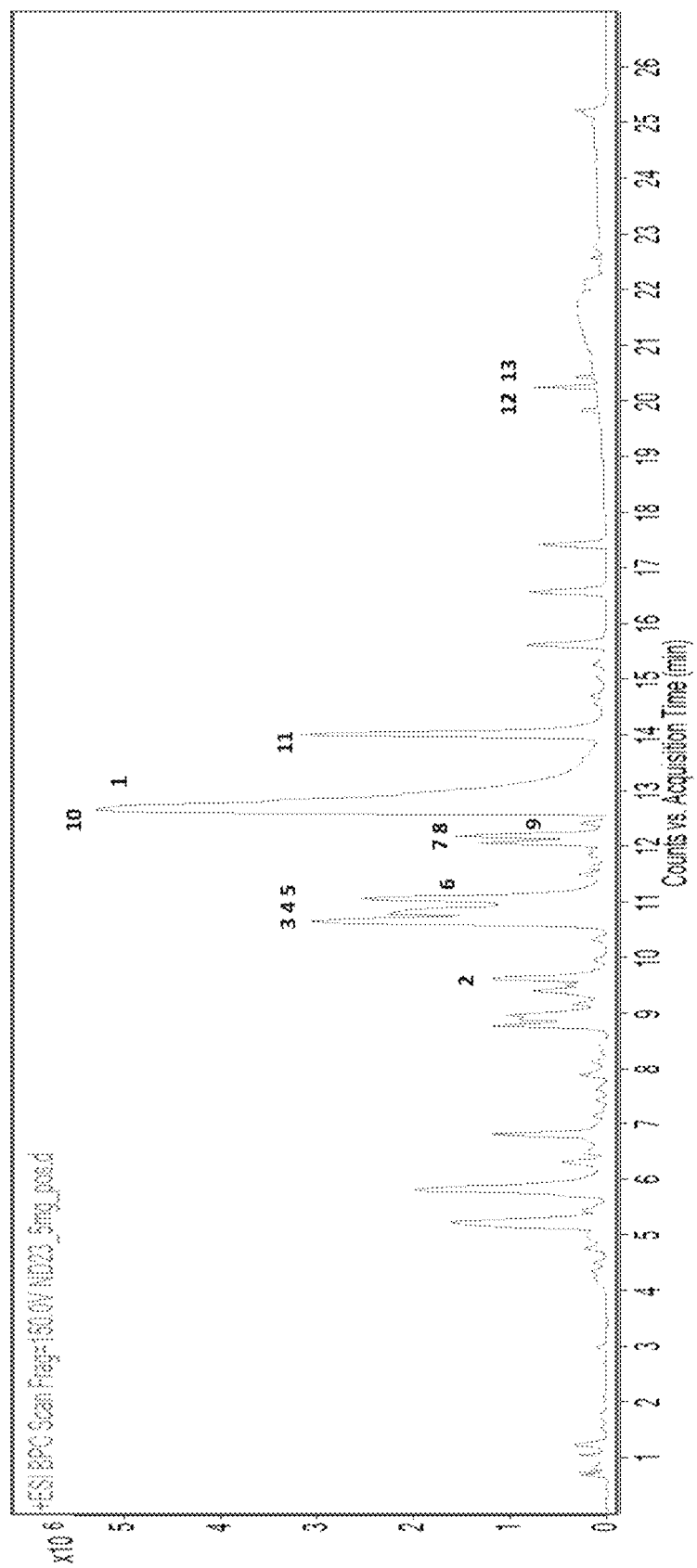
FIG. 1C shows the bioactive components in ND23 determined by LC-ESI-Q/TOF chromatograms.
Figure 1D:
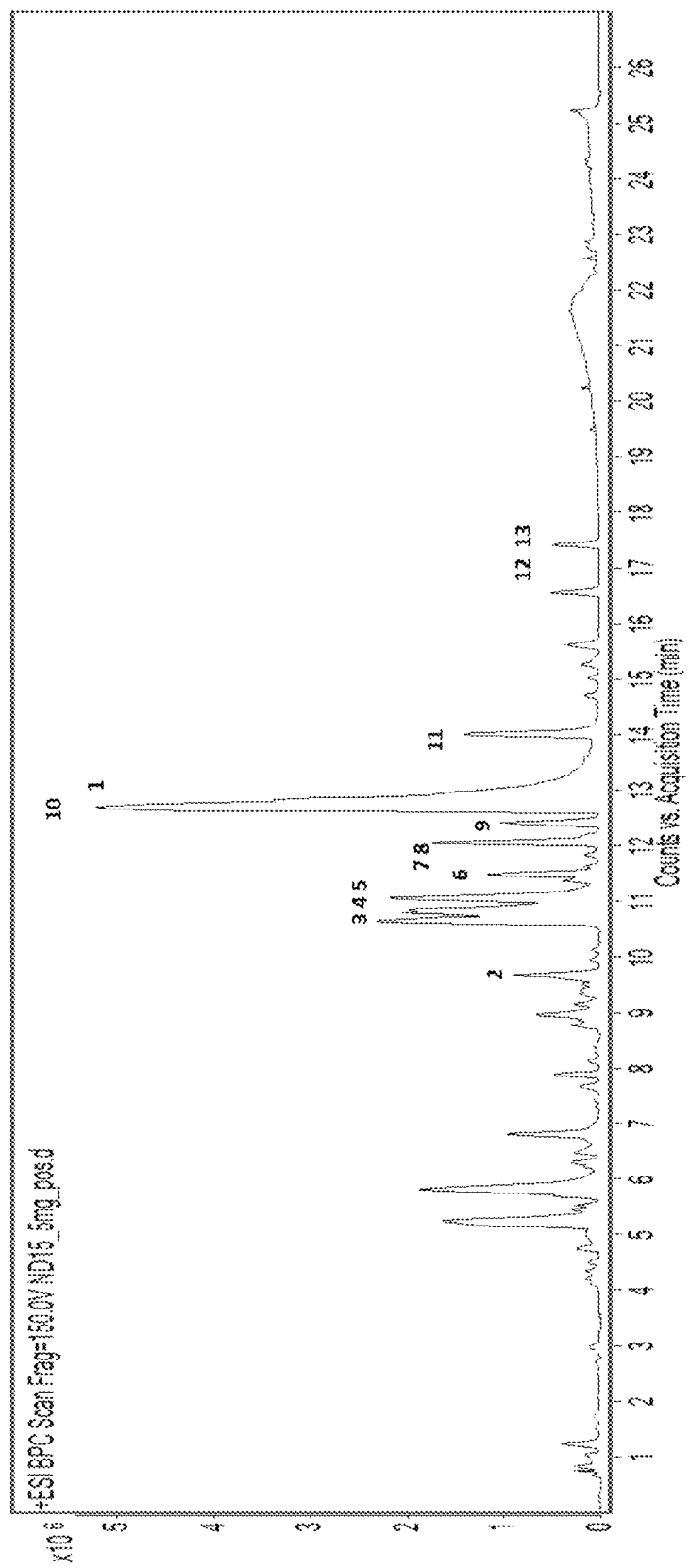
FIG. 1D shows the bioactive components in ND15 determined by LC-ESI-Q/TOF chromatograms.
Figure 1E:
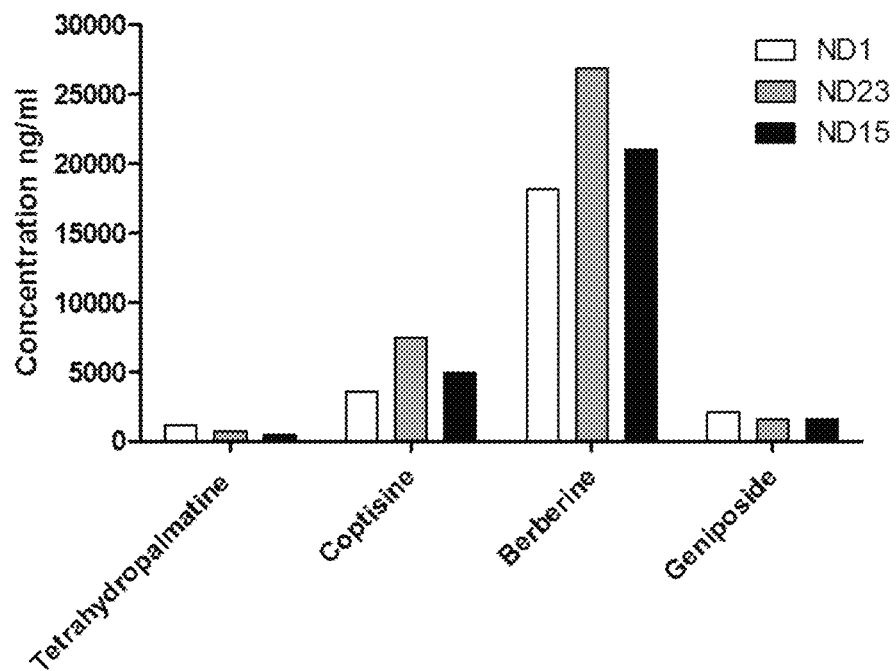
FIG. 1E shows the quantitative analysis for the major components of ND1, ND23 and ND15.
Figure 1F:
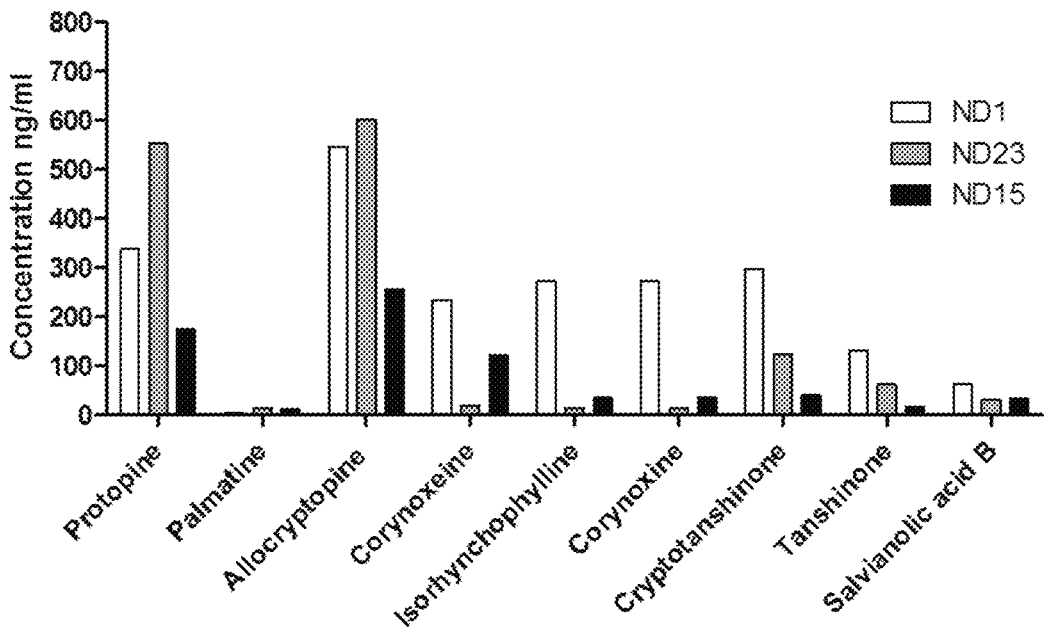
FIG. 1F shows the quantitative analysis for the minor components of ND1, ND23 and ND15.
Figure 2A:
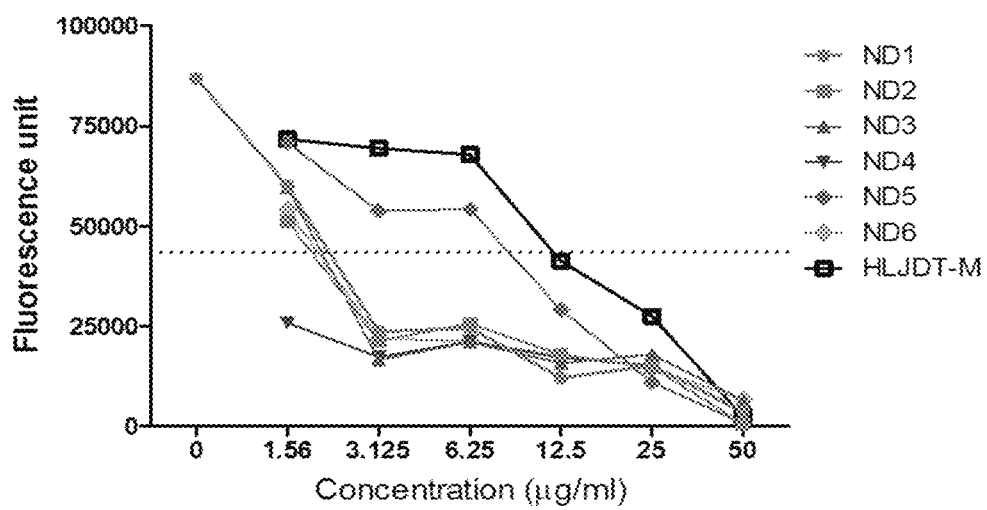
FIG. 2A shows the inhibition of $A\beta_{1-42}$ fibril formation by ND1 to ND6 and HLJDT-M extracts monitored by Thioflavin T (ThT) fluorescence. Each data represents the average of three replicates.
Figure 2B:
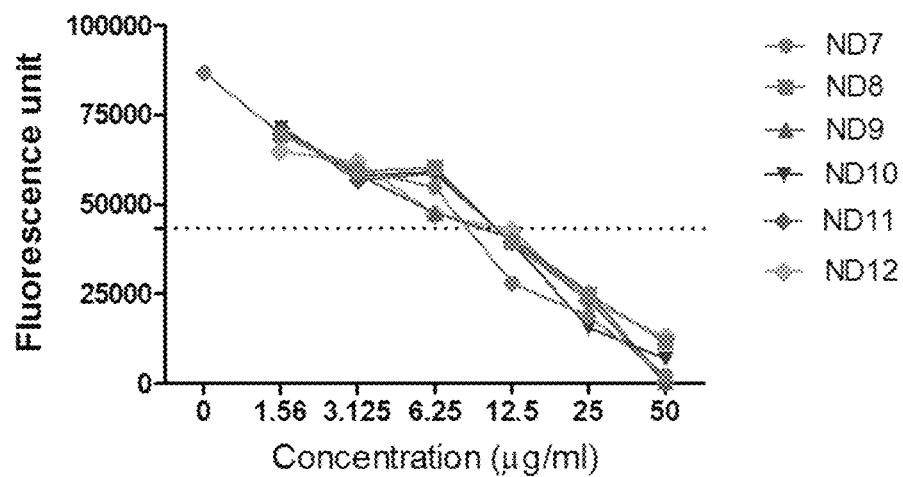
FIG. 2B shows the inhibition of $A\beta_{1-42}$ fibril formation by ND7 to ND12 extracts monitored by Thioflavin T (ThT) fluorescence. Each data represents the average of three replicates.
Figure 2C:
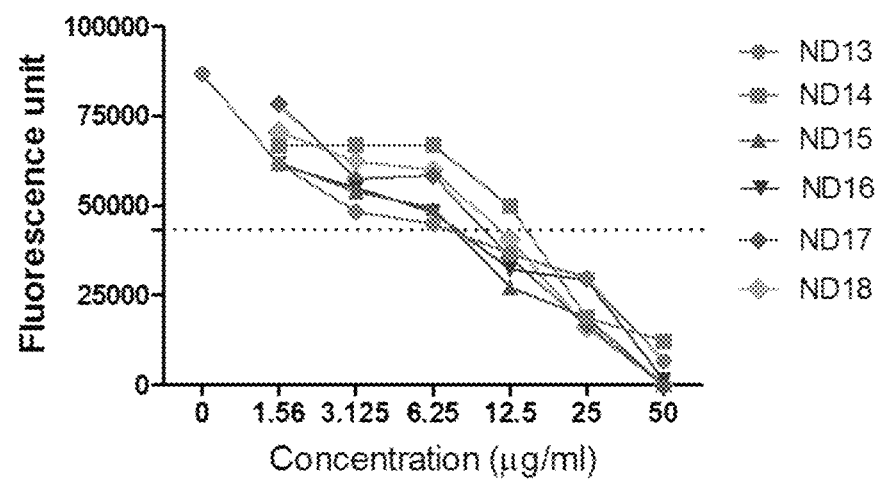
FIG. 2C shows the inhibition of $A\beta_{1-42}$ fibril formation by ND13 to ND18 extracts monitored by Thioflavin T (ThT) fluorescence. Each data represents the average of three replicates.
Figure 2D:
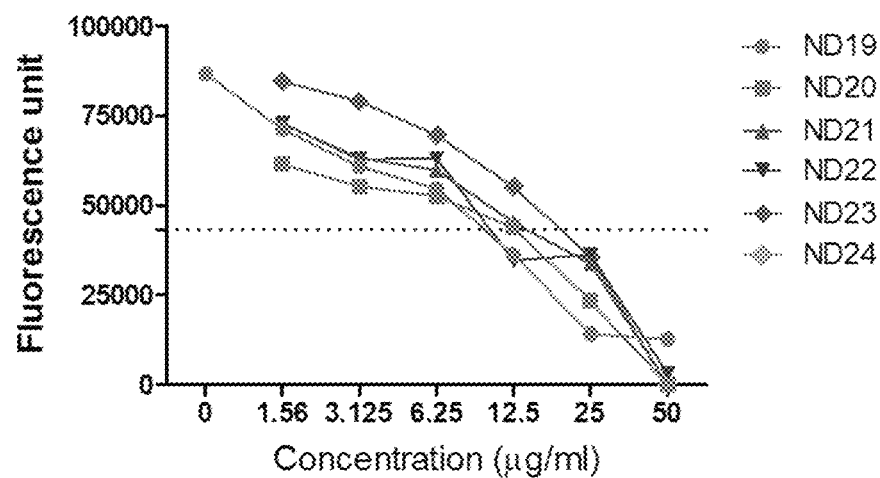
FIG. 2D shows the inhibition of $A\beta_{1-42}$ fibril formation by ND19 to ND24 extracts monitored by Thioflavin T (ThT) fluorescence. Each data represents the average of three replicates.
Figure 3A:
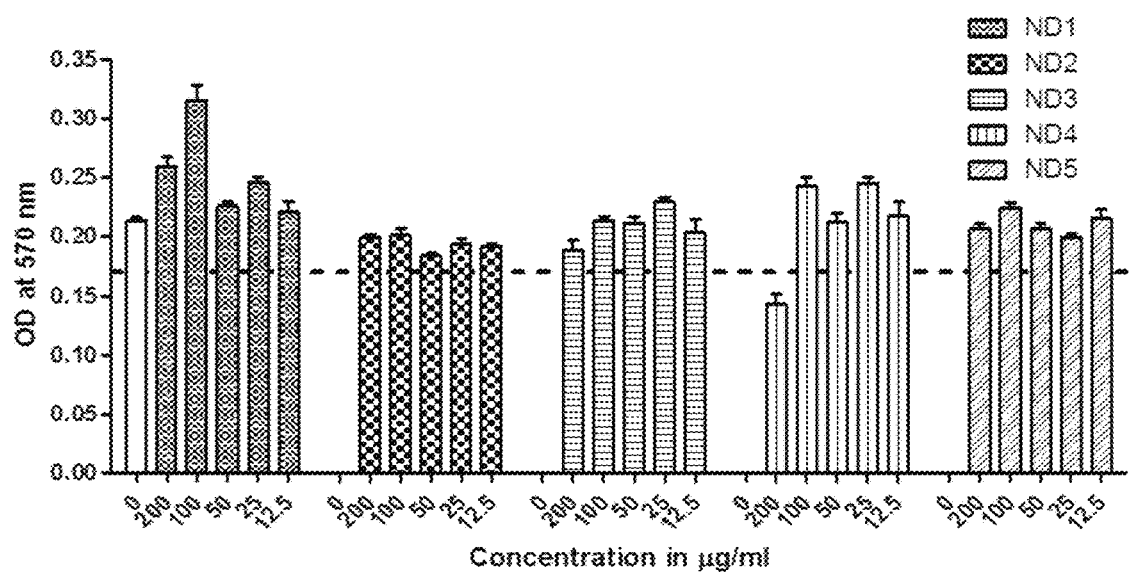
FIG. 3A shows the viability assay on different concentrations of ND1 to ND5 extracts. CHO cells expressing mutant APP V717F i.e. 7PA2 (CHO-APPV717F) cells were treated with ND extracts for 48 h and viability of cells were determined by MTT viability assay.
Figure 3B:
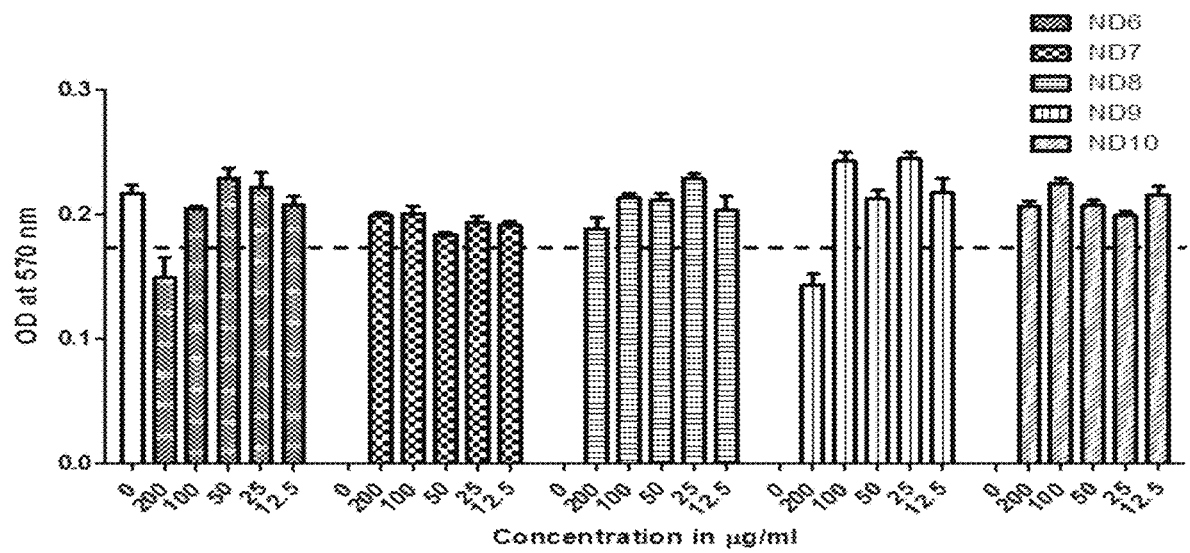
FIG. 3B shows the viability assay on different concentrations of ND6 to ND10 extracts. 7PA2 (CHO-APPV717F) cells were treated with ND extracts for 48 h and viability of cells were determined by MTT viability assay.
Figure 3C:
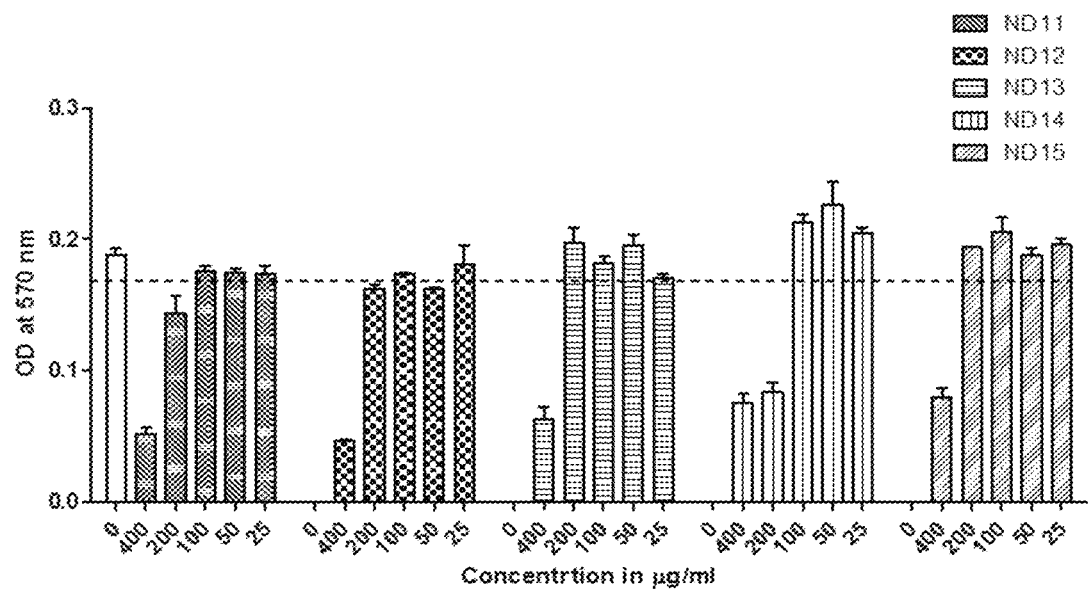
FIG. 3C shows the viability assay on different concentrations of ND11 to ND15 extracts. 7PA2 (CHO-APPV717F) cells were treated with ND extracts for 48 h and viability of cells were determined by MTT viability assay.
Figure 3D:
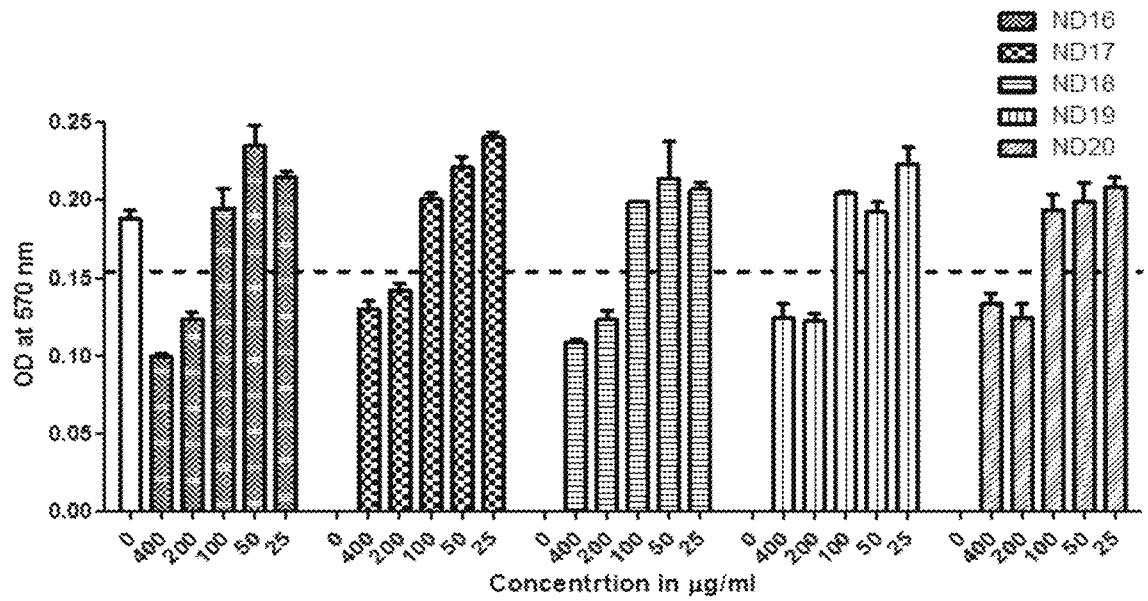
FIG. 3D shows the viability assay on different concentrations of ND16 to ND20 extracts. 7PA2 (CHO-APPV717F) cells were treated with ND extracts for 48 h and viability of cells were determined by MTT viability assay.
Figure 3E:
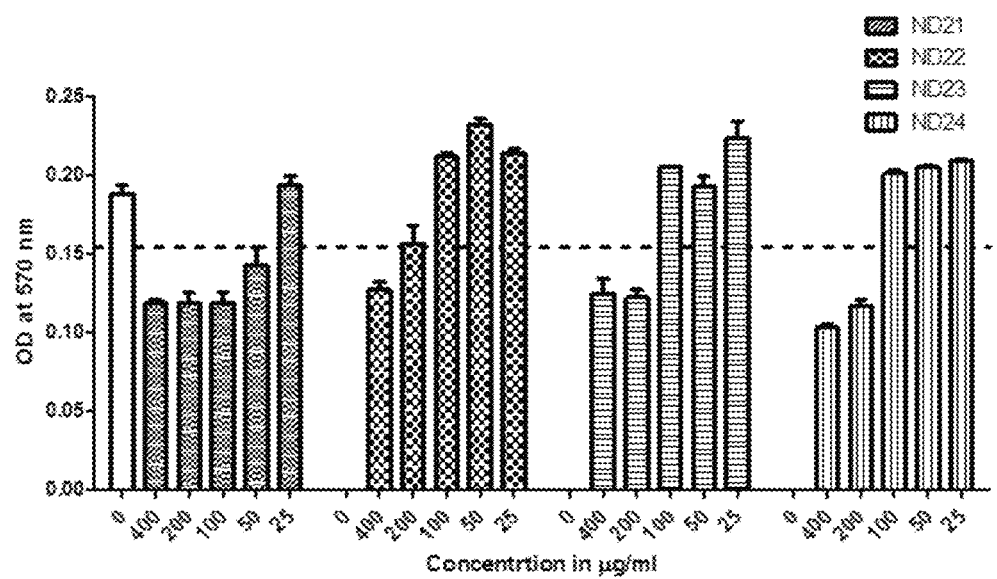
FIG. 3E shows the viability assay on different concentrations of ND21 to ND24 extracts. 7PA2 (CHO-APPV717F) cells were treated with ND extracts for 48 h and viability of cells were determined by MTT viability assay.

Quality Test and Preparation of Extracts:

Initial testing of quality control of individual herb of ND formulation was performed according to the Chinese Pharmacopeia by testing the percentage of key marker of each herb. All 6 herbs of ND (FIG. 1A) were purchased from HKBU Chinese Medicine clinic. Voucher samples of each herb were deposited in the herbarium of the School of Chinese Medicine, Hong Kong Baptist University. The herbs were identified with both Chinese and botanical (Latin binomial) names. Dry Huanglian, Huangbai, Zhizi, Danshen, Gouteng and Yanhusuo are weight according to the specified weight ratio and mixed to obtain the herbal combination. The herbal combination is pulverized into powder. Roots and rhizomes can cut into small pieces prior to being pulverized. The powdered herbal combination is decocted in water and steeped in 70% alcohol (e.g. ethanol) overnight and then is filtered. The decocting and steeping steps may be repeated for several times (e.g. 2 to 3 times). The filtered solution is concentrated in a rotary evaporator under vacuum at approximately 50° C., and then lyophilized under vacuum to obtain the herbal extract of the present invention. The herbal extract can be stored at 4° C. Other extraction method as appreciated by the skilled in the art may be used in obtaining the herbal extract of the present invention. The yield of the herbal extract is approximately 10%-20% by weight of the starting herbal combination. The content of ND1, ND15 and ND23 was analyzed qualitative and quantitatively by LC-MS-Q-TOF analysis (FIG. 1B). The components of ND are namely berberine, geniposide, palmatine, protopine, tetrahydropalmatine, allocryptopine, coptisine, corynoxeine, corynoxine, isorhyncophyline, salvianolic acid B, tanshinone 2A, and cryptotanshinone. The quantitative analysis of the ND1, ND23 and ND15 formulations were assessed and the levels of major and minor bioactive components are given (FIGS. 1C-1F). ND is the combination of 6 herbs namely Huanglian:Huangbai:ZhiZi:Yanhusuo:Danshen:Gouteng, the given ratio is for the preparation of 1 kg herbal formulation of ND. The weight ratio of ND1 of 6 herbs Huanglian:Huangbai:ZhiZi:Yanhusuo:Danshen:Gouteng is 0.83:1.66:4.16:2.91:4.57:6.24 respectively, the weight ratio of ND15 of 6 herbs Huanglian:Huangbai:ZhiZi:Yanhusuo:Danshen:Gouteng is 4.15:3.46:3.46:2.76:6.22:6.22 respectively and the weight ratio of ND23 of 6 herbs Huanglian:Huangbai:ZhiZi:Yanhusuo:Danshen:Gouteng is 3.45:1.92:1.53:2.69:5.76:4.22 respectively. ND dose in mice was calculated based on the $LD_{50}$ and the doses are 1.9 g/kg/day, 3.8 g/kg/day and 7.6 g/kg/day. HUMAN EQUIVALENT DOSE (HED)=Animal Dose (g/kg)×[Animal Km/Human Km]. The correction factor (Km) is estimated by dividing the average body weight (kg) of species to its body surface area ($m^2$). Km factor for human is 37 and Km factor for mouse is 3. ND equivalent dose in humans are 0.154 g/kg/day, 0.308 g/kg/day and 0.617 g/kg/day.

In Vitro Aβ Aggregation Assay

The anti-Aβ aggregation potency of aqueous extract of ND was assessed by the inhibition of $A\beta_{1-42}$ fibrils by using the thioflavin T binding assay. At first, the inventors examined the effects of 24 different extracts of NDs on the formation of Aβ fibrils as described by the inventors. The inventors found that several extracts of ND have potent inhibitory effects on fibril formation of $A\beta_{1-42}$ in concentration-dependent manners; among the screened 24 ND extracts, only 6 isolates in particular; ND1, ND2, ND3, ND4, ND6 and ND15 inhibited Aβ aggregation (FIGS. 2A-2D) most intensively. Extracts from ND1-4 and 6 inhibited the aggregation in a dose-dependent manner at doses between 1.56 and 50 μg/ml. The approximate $IC_{50}$ values of these five extracts were in the range of 2-2.5 μg/ml. However, the $IC_{50}$ value of ND15 was around 7 μg/ml. It has been generally believed that neurological dysfunction appears to be small oligomeric assemblies of Aβ, termed ADDLs (Aβ-derived diffusible ligands), rather than the large insoluble fibrils found in amyloid plaques in the early stages of AD.

MTT Viability Test:

The 24 extracts prepared were tested on 7PA2-CHO cells expressing mutant APP V717F for their potential cytotoxicity. The inventors tested each extract at five different concentrations in 48 wells plate for 48 h. The concentrations from 12.5 to 200 μg/ml were tested in the 7PA2 cells indicated more than 70-80% viability. Results of the viability test are shown in (FIGS. 3A-3E).

Figure 4A:
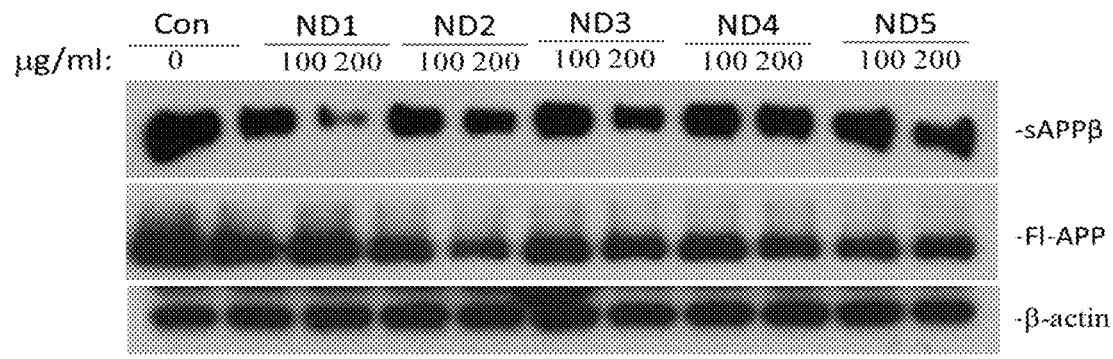
FIG. 4A shows the APP modulation effect of ND extracts in 7PA2 (CHO-APPV717F) cells. The levels of FL-APP, sAPPβ and β-actin were determined by western blot analysis for ND1 to ND5. ND1 dose-dependently decreased the levels of sAPPβ.
Figure 4B:
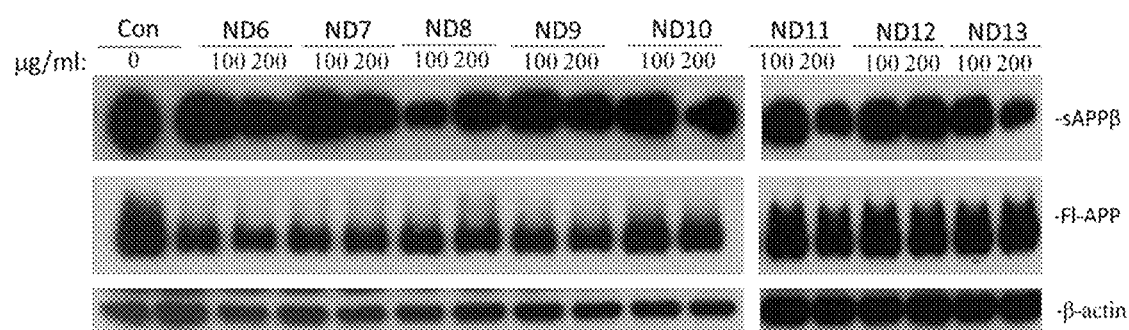
FIG. 4B shows the APP modulation effect of ND extracts in 7PA2 (CHO-APPV717F) cells. The levels of FL-APP, sAPPβ and β-actin were determined by western blot analysis for ND6 to ND13.
Figure 4C:
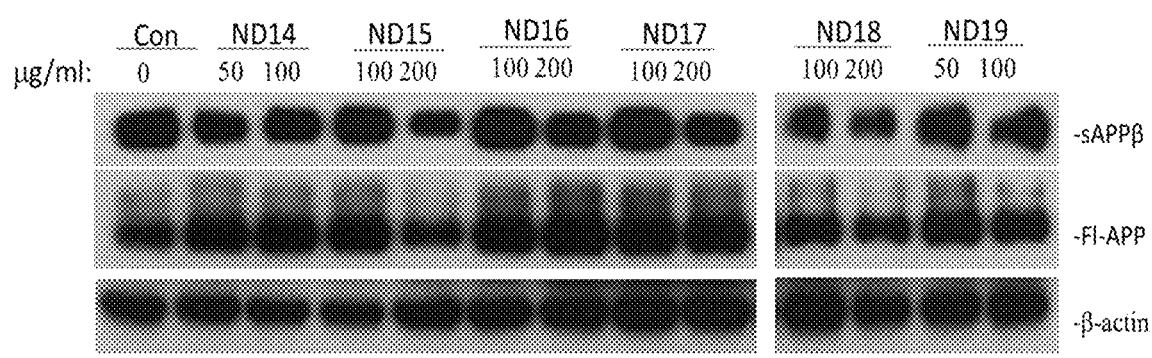
FIG. 4C shows the APP modulation effect of ND extracts in 7PA2 (CHO-APPV717F) cells. The levels of FL-APP, sAPPβ and β-actin were determined by western blot analysis for ND14 to ND19. ND15 dose-dependently decreased the levels of sAPPβ.
Figure 4D:
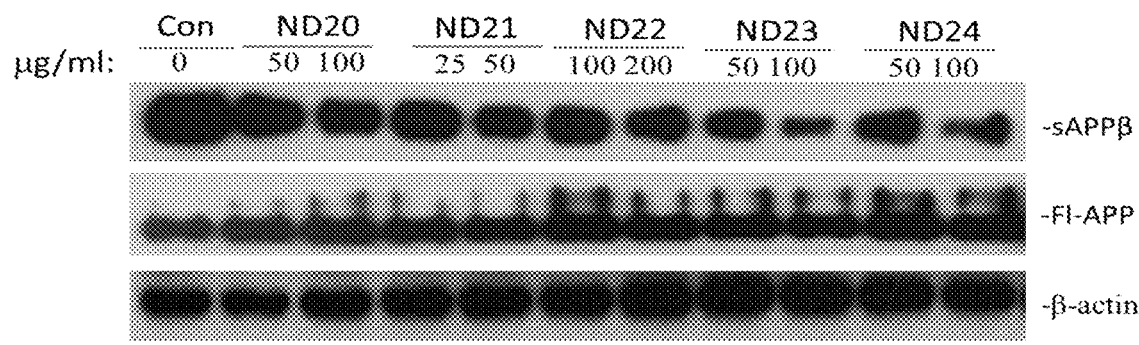
FIG. 4D shows the APP modulation effect of ND extracts in 7PA2 (CHO-APPV717F) cells. The levels of FL-APP, sAPPβ and β-actin were determined by western blot analysis for ND20 to ND24. ND23 dose-dependently decreased the levels of sAPPβ.
Figure 4E:
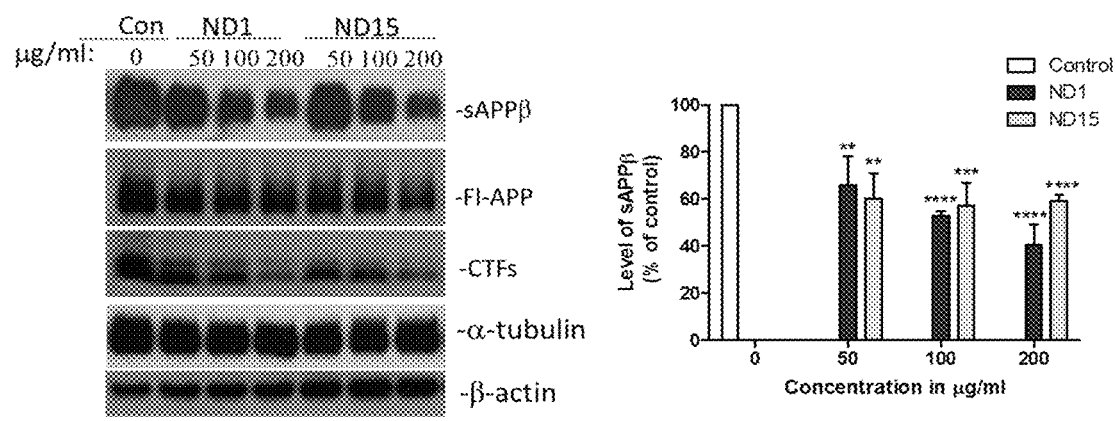
FIG. 4E shows the quantification of ND1 and ND15 dose-dependently decreased the levels of sAPPβ and CTFs, the data are presented as the mean±SD, $P \leq 0.05$, *$P \leq 0.001$.
Figure 5A:
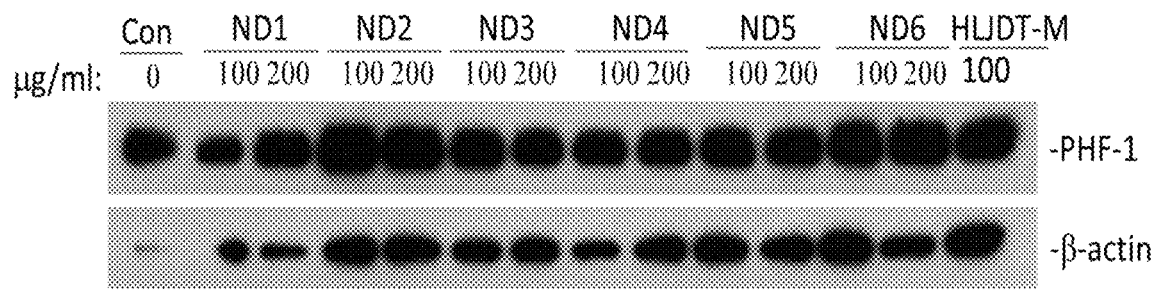
FIG. 5A shows the effect of ND1 to ND6 extracts on the levels of PHF-1 Tau protein in SH-SY5Y cells stably expressing P301L mutant.
Figure 5B:
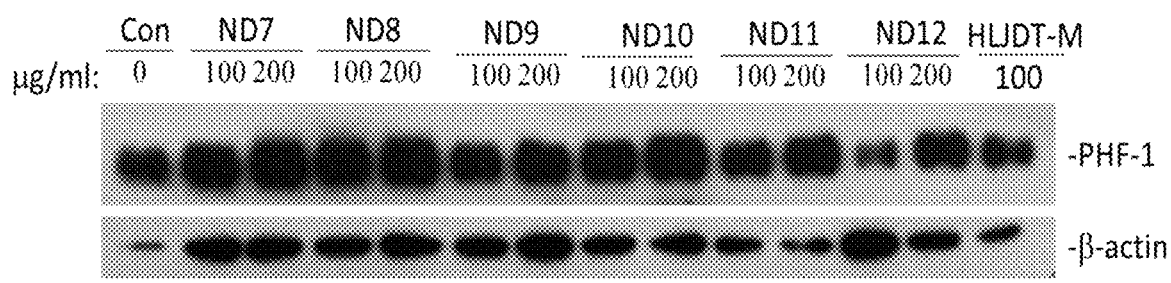
FIG. 5B shows the effect of ND7 to ND12 extracts on the levels of PHF-1 Tau protein in SH-SY5Y cells stably expressing P301L mutant.
Figure 5C:
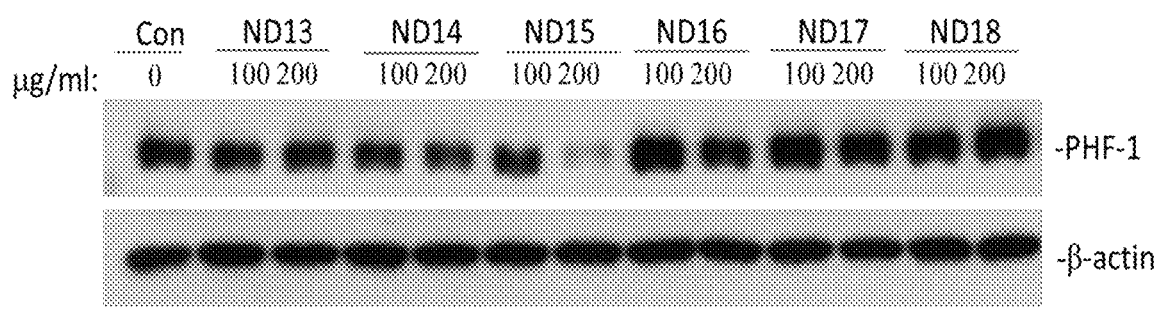
FIG. 5C shows the effect of ND13 to ND18 extracts on the levels of PHF-1 Tau protein in SH-SY5Y cells stably expressing P301L mutant. Among the screened extracts, only ND15 (200 μg/ml) reduced the level of PHF1 in a dose dependent manner.
Figure 5D:
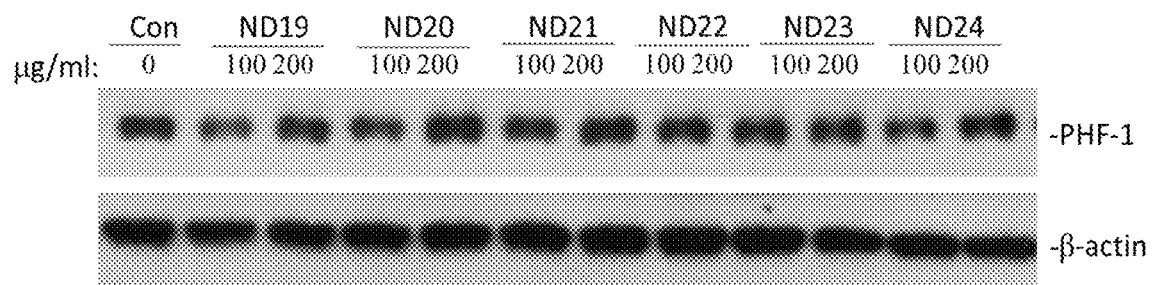
FIG. 5D shows the effect of ND19 to ND24 extracts on the levels of PHF-1 Tau protein in SH-SY5Y cells stably expressing P301L mutant.

APP Modulation Assay:

For APP modulation assay, $0.15 \times 10^6$ 7PA2 cells/well was seeded onto 12-well plates 24 h prior to treatment with extracts. For initial screening, cells were treated with two different doses of ND (100 and 200 μg/mL or 50 and 100 μg/mL final concentration) for 48 h then the extracellular media were collected for the detection of sAPPβ and then cells were harvested to observe the FL-APP, CTFs and β-actin through western blot analysis. As shown in the immunoblots (FIGS. 4A-4D), ND1 and ND15 extracts decreased sAPPβ in a dose-dependent manner without affecting the FL-APP. To further confirm sAPPβ reducing effect of ND1 and ND15, the inventors have repeated the APP modulation assay three times. ND1 and ND15 dose-dependently decreased the levels of sAPPβ and CTFs (FIG. 4E).

Tau Assay:

The inventors then compared the anti-tau activity of 24 different ND extracts in SH-SY5Y cells stably expressing Tau mutant P301L with an aberrant increase in phospho-Tau and insoluble total Tau at molecular weight of 70 kDa. SH-SY5Y-P301L cells were treated with two different concentrations of NDs for 48 h (FIGS. 5A-5D). The inventors have already performed the viability assay on different concentration of NDs and the non-toxic concentrations were used for initial screening of the NDs for Tau-reducing activity. Among the screened extracts, ND15 and ND1 reduced the levels of insoluble phospho-Tau (PHF-1).

Figure 6A:
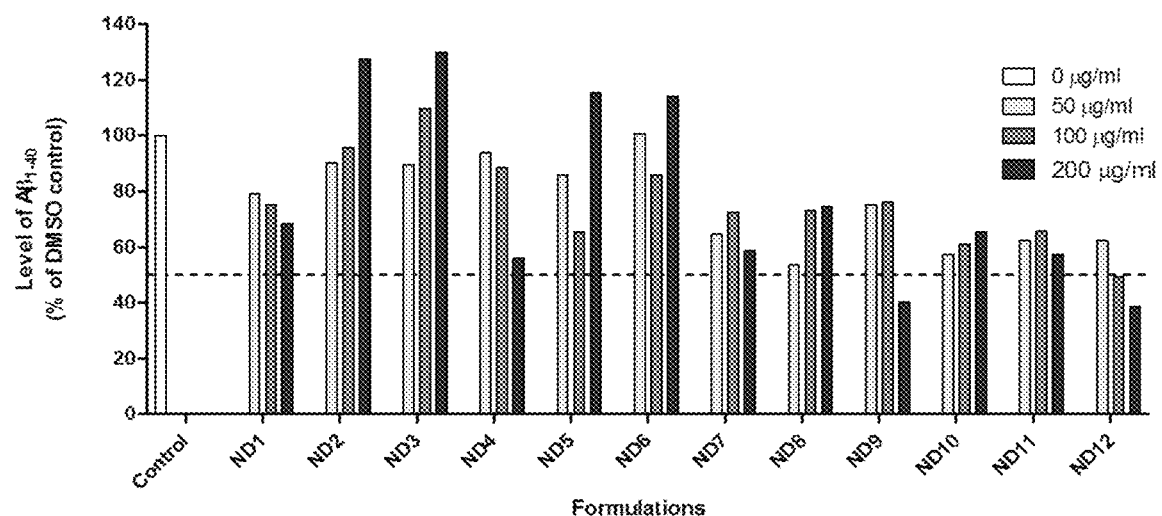
FIG. 6A shows the effect of ND1 to ND12 extracts on the levels of $A\beta_{1-40}$ by double sandwich ELISA. The ND1 extract decreased $A\beta_{1-40}$ levels in a dose-dependent manner.
Figure 6B:
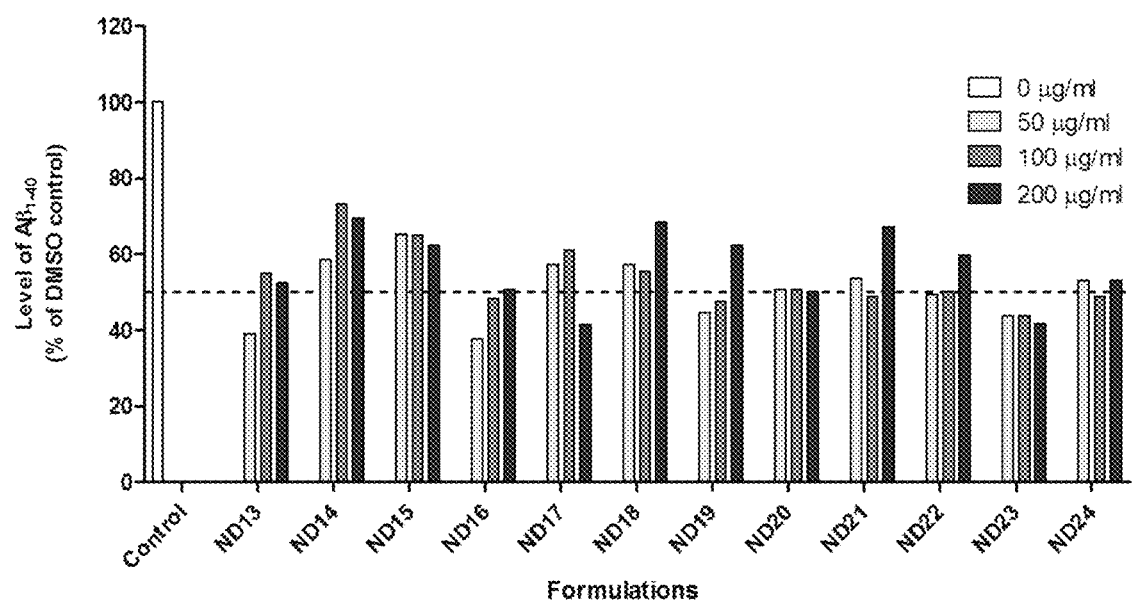
FIG. 6B shows the effect of ND13 to ND24 extracts on the levels of $A\beta_{1-40}$ by double sandwich ELISA. The ND15 and ND23 extract decreased $A\beta_{1-40}$ level in a dose-dependent manner.
Figure 6C:
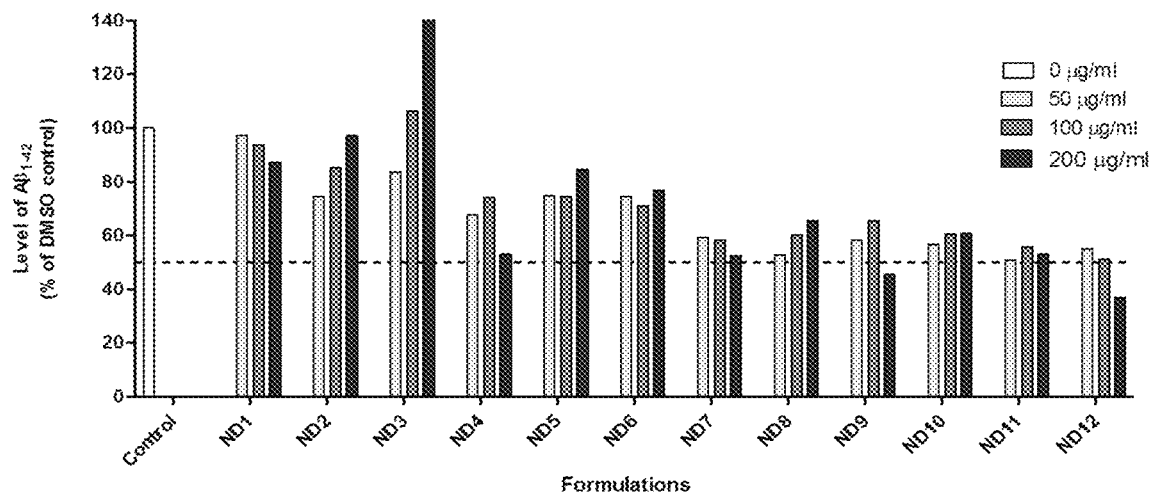
FIG. 6C shows the effect of ND1 to ND12 different ND extracts on the level of $A\beta_{1-42}$ by double sandwich ELISA. The ND1 extract decreased $A\beta_{1-42}$ level in a dose-dependent manner.
Figure 6D:
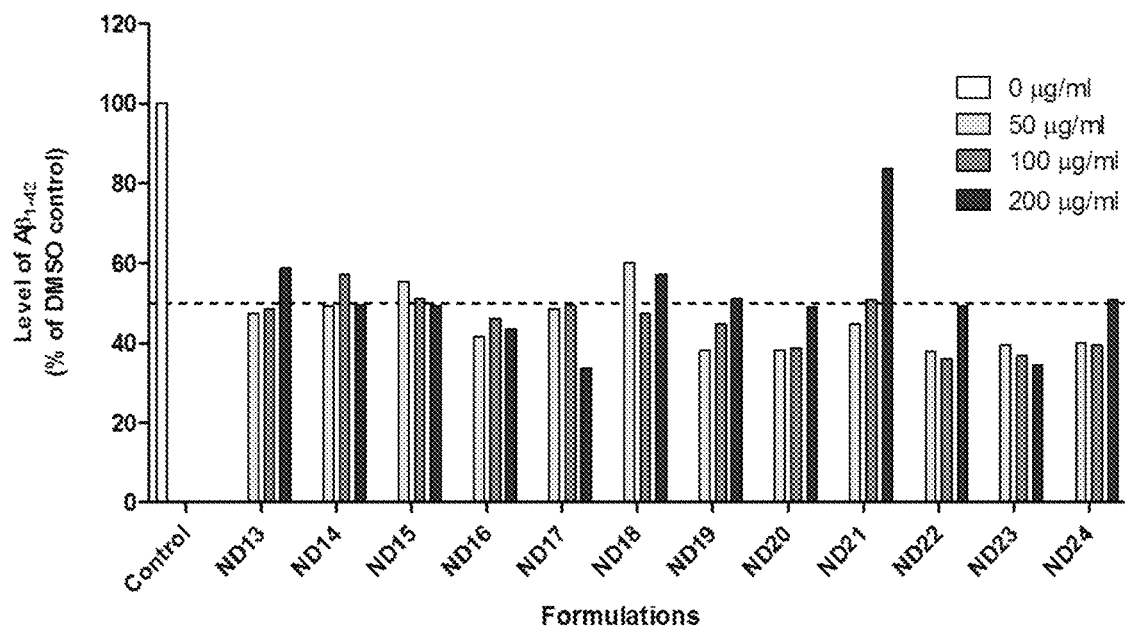
FIG. 6D shows the effect of ND13 to ND24 different ND extracts on the level of $A\beta_{1-42}$ by double sandwich ELISA. The ND15 and ND23 extract decreased $A\beta_{1-42}$ level in a dose-dependent manner.

Analysis $A\beta_{1-40}$ and $A\beta_{1-42}$ Levels by ELISA Assay:

For $A\beta_{1-40}$ and $A\beta_{1-42}$ ELISA assay, $0.15 \times 10^6$ 7PA2 cells/well was seeded onto 12-well plates 24 h prior to treatment with extracts. For initial screening, cells were treated with three different doses of ND (50,100 and 200 μg/mL final concentration) for 48 h then the extracellular media were collected for the detection of $A\beta_{1-40}$ and $A\beta_{1-42}$ to observe the levels through double sandwich ELISA analysis. As shown in the results the ND1, ND7, ND12, ND15 and ND23 extracts decreased the levels of $A\beta_{1-40}$ (FIGS. 6A-6B). To further confirm $A\beta_{1-42}$ levels reducing effect of ND1, ND7, ND12, ND15 and ND23 (FIGS. 6C-6D) were assessed by double sandwich ELISA. Among all the extracts tested in ELISA only ND1, ND15 and ND23 extracts consistently decreased the levels of $A\beta_{1-40}$ and $A\beta_{1-42}$ levels in a dose-dependent manner.

Conclusion of In Vitro Assays:

Since ND1, ND23 and ND15 consistently showed anti-Aβ aggregation, anti-sAPPβ, anti-Aβ and anti-Tau activities; the inventors selected ND1, ND23 and ND15 for in vivo studies in the transgenic mice models 5XFAD and 3XTg-AD.

Figure 7A:
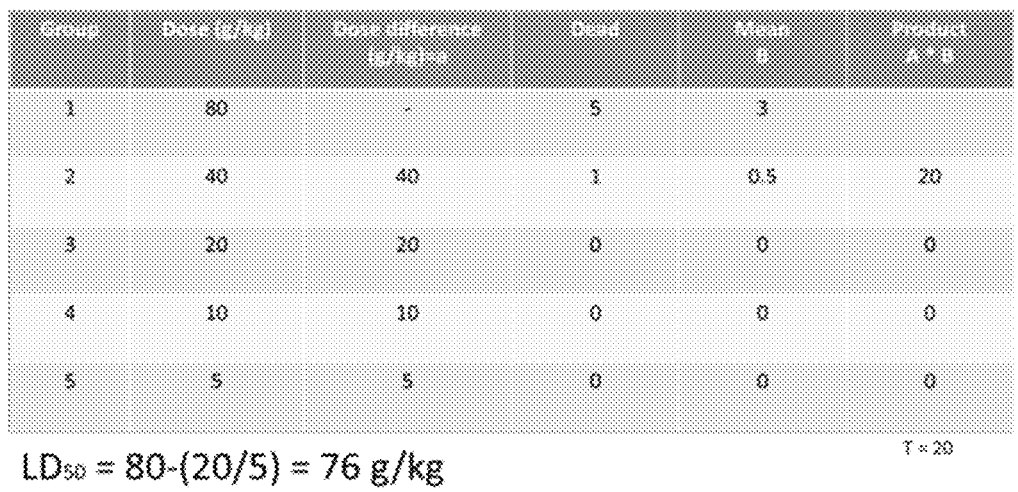
FIG. 7A shows the $LD_{50}$ of ND1 in wild type C57BL/6 mice.
Figure 7B:
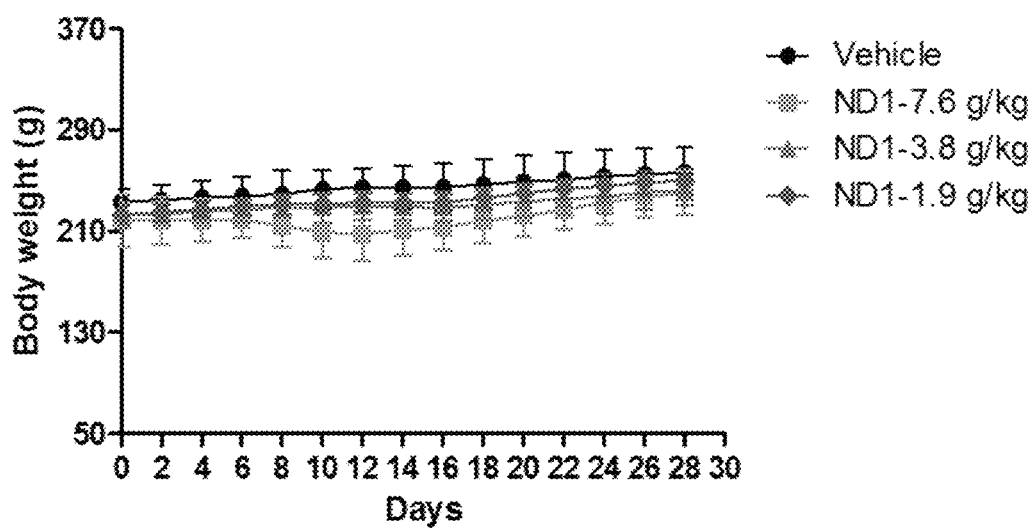
FIG. 7B shows the body weight of wild type C57BL/6 mice for the ND1 sub-chronic toxicity.
Figure 7C:
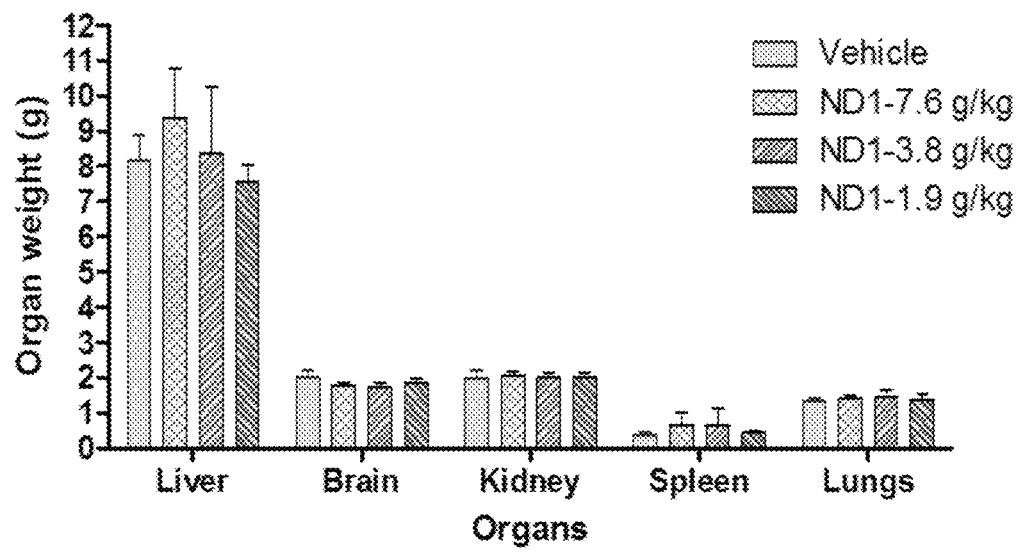
FIG. 7C shows the organ weight of wild type C57BL/6 mice for ND1 sub-chronic toxicity.
Figure 7D:
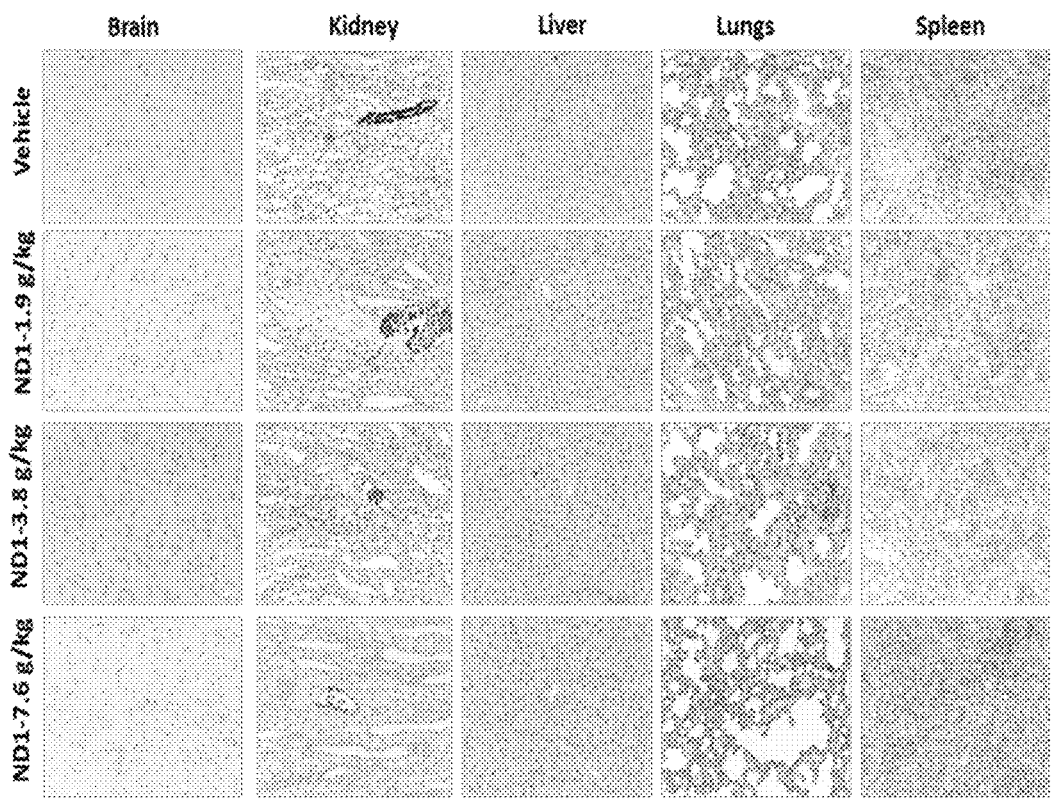
FIG. 7D shows the histopathological observations of wild type C57BL/6 mice for ND1 sub-chronic toxicity.
Figures 10A, 10B:
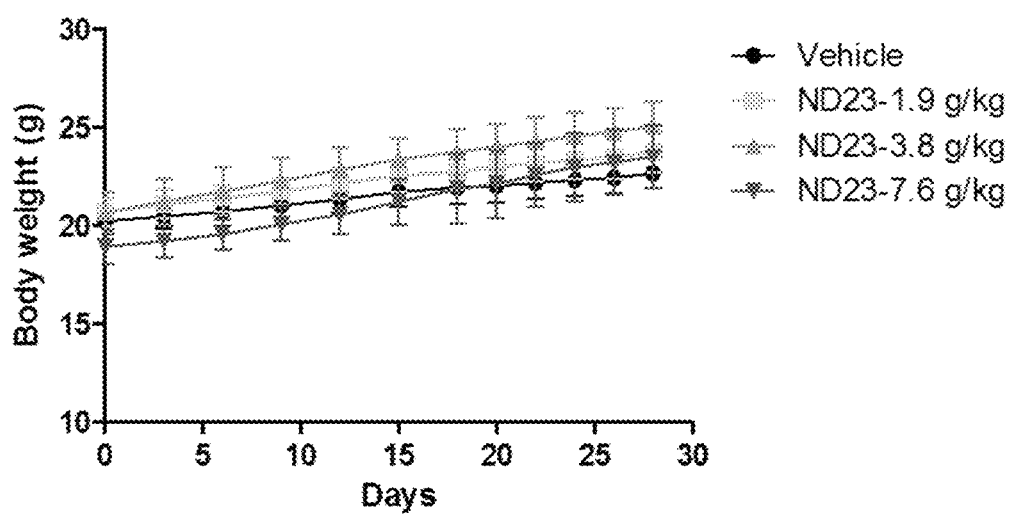
FIG. 10A shows the $LD_{50}$ of ND23 in wild type C57BL/6 mice.
FIG. 10B shows the body weight of wild type C57BL/6 mice for the ND23 sub-chronic toxicity.
Figure 10C:
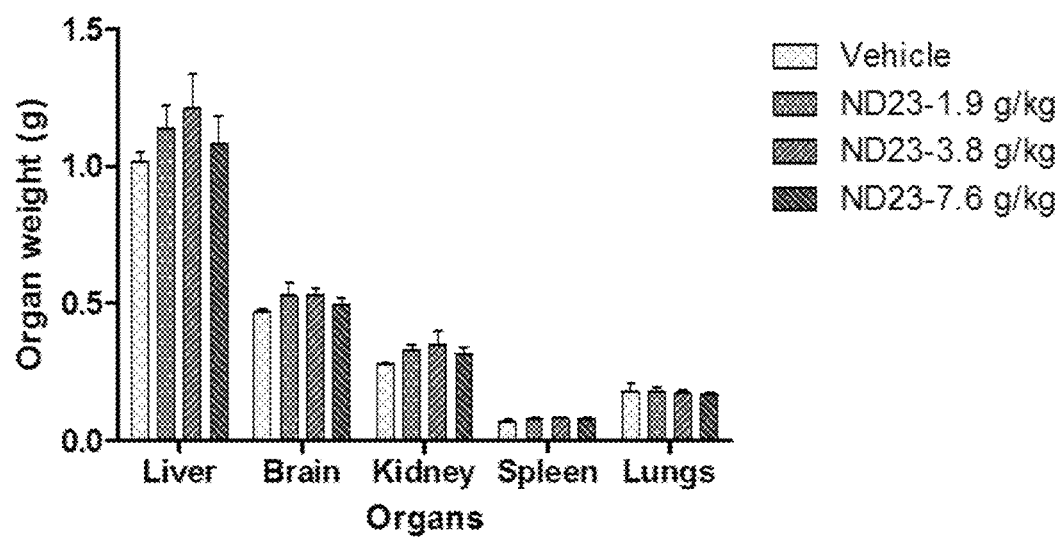
FIG. 10C shows the organ weight of wild type C57BL/6 mice for ND23 sub-chronic toxicity.
Figure 10D:
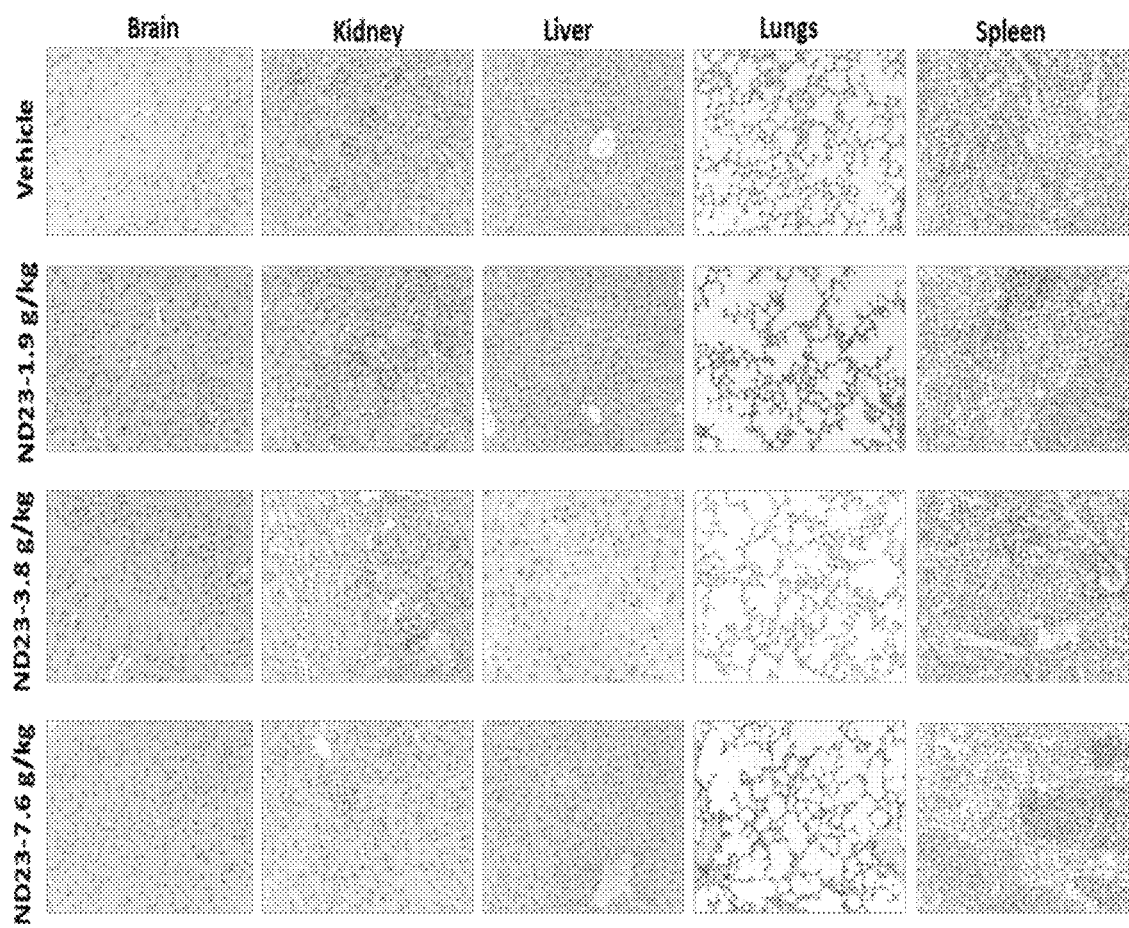
FIG. 10D shows histopathological observations of wild type C57BL/6 mice for ND23 sub-chronic toxicity.
Figures 13A, 13B:
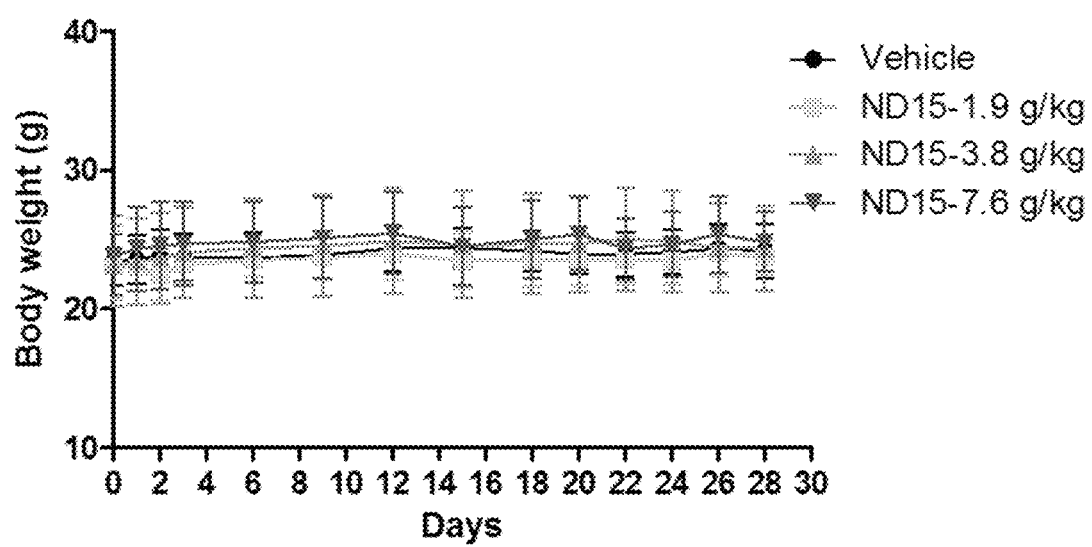
FIG. 13A shows the $LD_{50}$ of ND15 in wild type C57BL/6 mice.
FIG. 13B shows the body weight of wild type C57BL/6 mice for the ND15 sub-chronic toxicity.
Figure 13C:
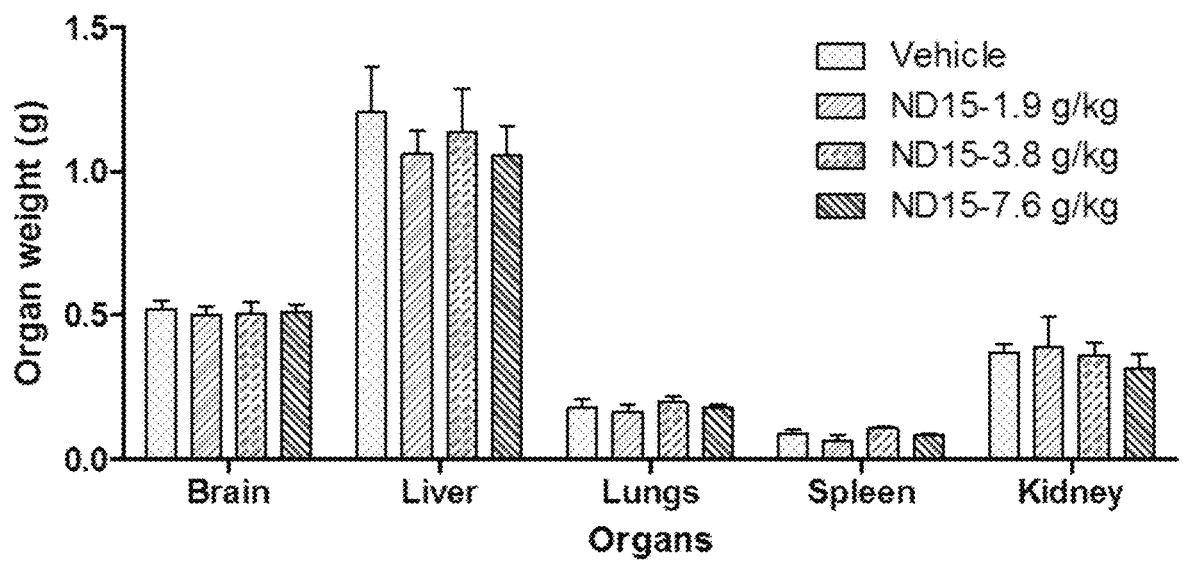
FIG. 13C shows the organ weight of wild type C57BL/6 mice for ND15 sub-chronic toxicity.
Figure 13D:
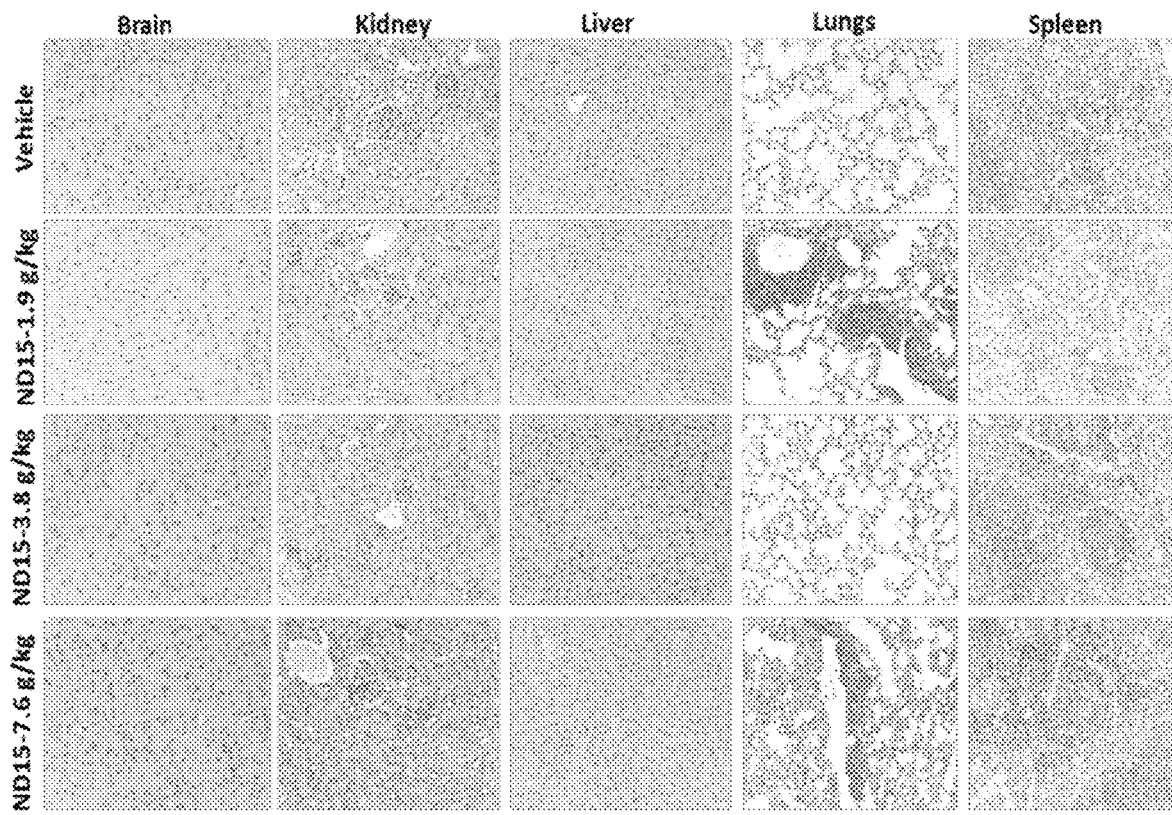
FIG. 13D shows histopathological observations of wild type C57BL/6 mice for ND15 sub-chronic toxicity.

Acute and Sub-Chronic Toxicity of ND1, ND23 and ND15 in Wild Type C57BL/6 Mice:

In the preliminary experiments, the inventors performed acute toxicity to investigate the toxicity of ND1, ND23 and ND15 in wild type C57BL/6 mice. The $LD_{50}$ of ND1 was around 76 g/kg (FIG. 7A) in wild type C57BL/6 mice. The $LD_{50}$ of ND23 and ND15 was around 80 g/kg (FIGS. 10A, 13A) in wild type C57BL/6 mice. Further the inventors carried out the sub-chronic toxicity of ND1, ND23, and ND15 (1.9 g/kg/day, 3.8 g/kg/day, 7.6 g/kg/day) in wild type C57BL/6 mice. ND1, ND23 and ND15 did not influence the animal body weight during the course of treatment (FIGS. 7B, 10B, 13B). At the end of 28 days the animals were euthanized and the weight of the organs were recorded and compared with the vehicle and treatment groups (FIGS. 7C, 10C, 13C). The tissues of brain, liver, kidneys, lungs and spleen from each mouse in the sub-chronic toxicity study were tested for histopathological examination. Gross lesions were examined by staining with hematoxylin and eosin (HE). The histopathological observations and gross necropsy of each animal organ were observed (FIGS. 7D, 10D, 13D) for ND1, ND23 and ND15 sub-chronic toxicity.

Figure 8A:
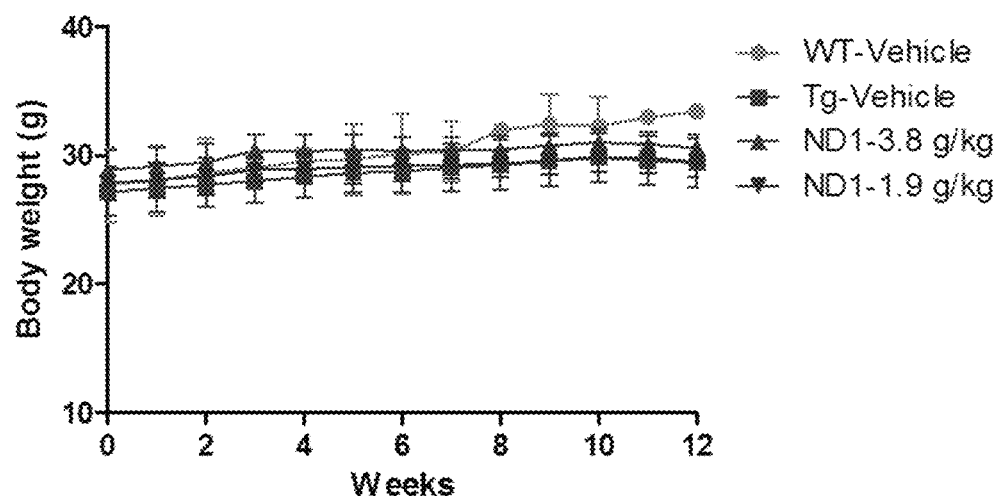
FIG. 8A shows ND1 does not influence the body weight in 5XFAD male mice.
Figure 8B:
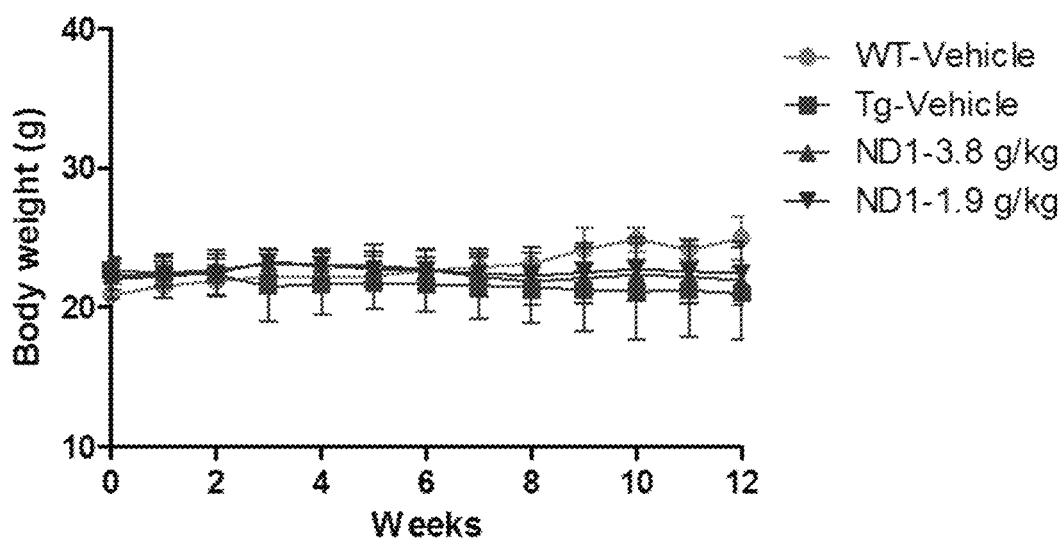
FIG. 8B shows ND1 does not influence the body weight in 5XFAD female mice.
Figure 8C:
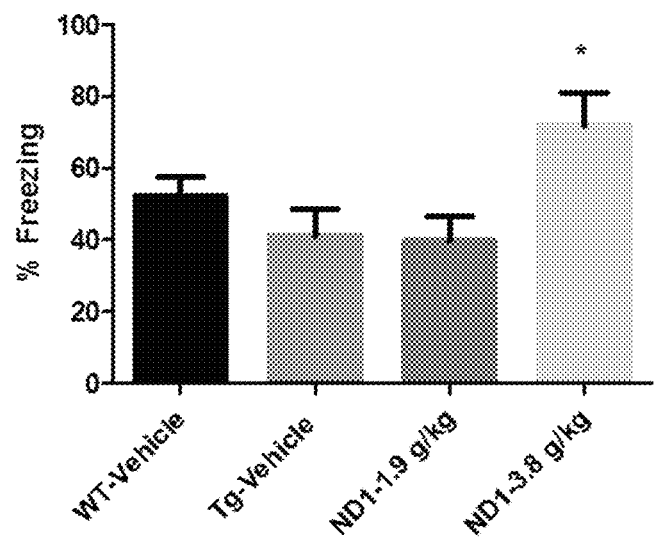
FIG. 8C shows ND1 ameliorates hippocampal and amygdala-dependent memory deficit in 5XFAD mice by contextual fear conditioning.
Figure 8D:
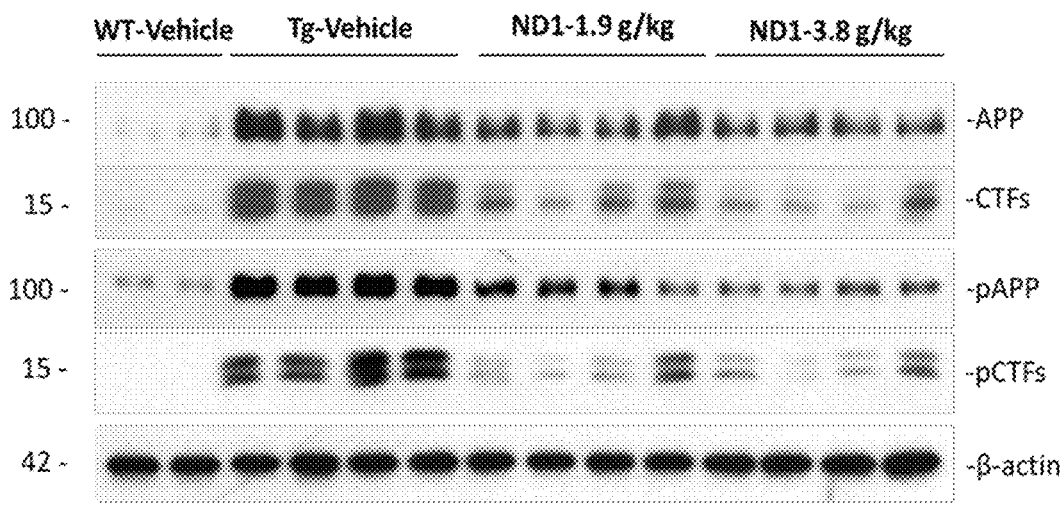
FIG. 8D shows ND1 significantly and dose-dependently reduced the levels of APP, CTFs, pAPP and pCTFs in 5XFAD mice by the western blot analysis.
Figure 8E:
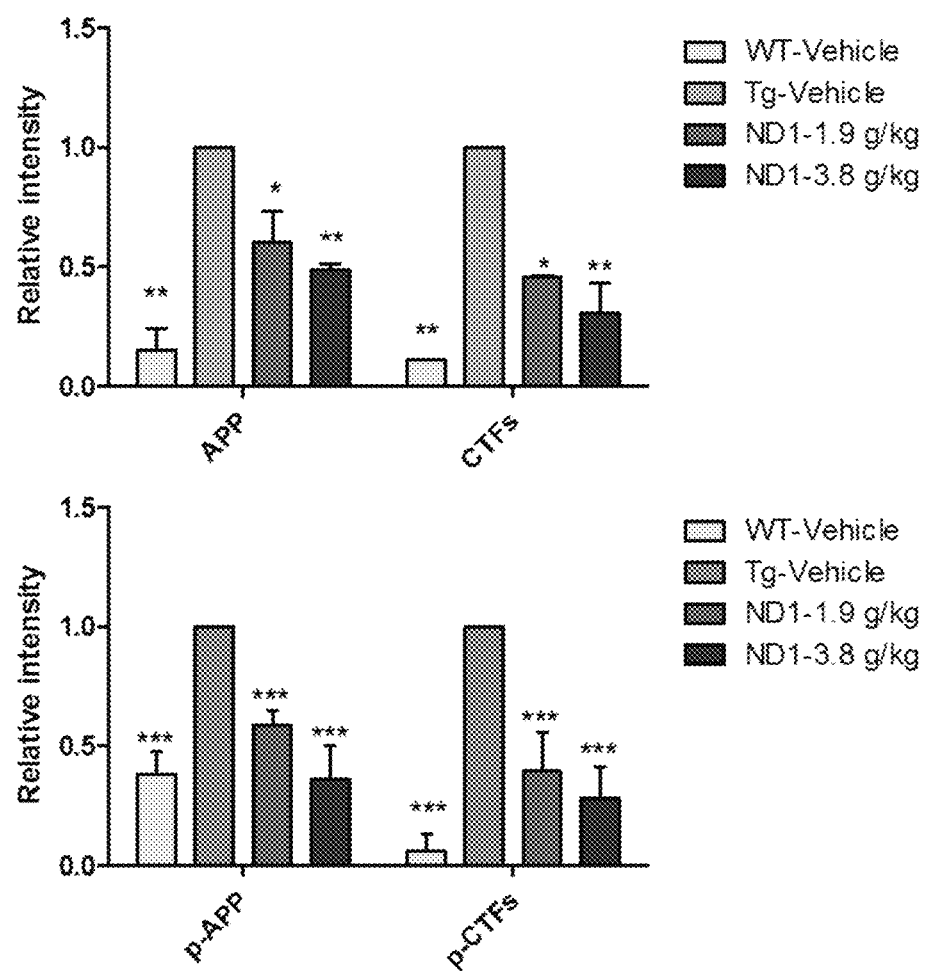
FIG. 8E shows the quantification of APP, CTFs, pAPP and pCTFs in 5XFAD mice by the western blot analysis, the data are presented as the mean±SD.
Figure 8F:
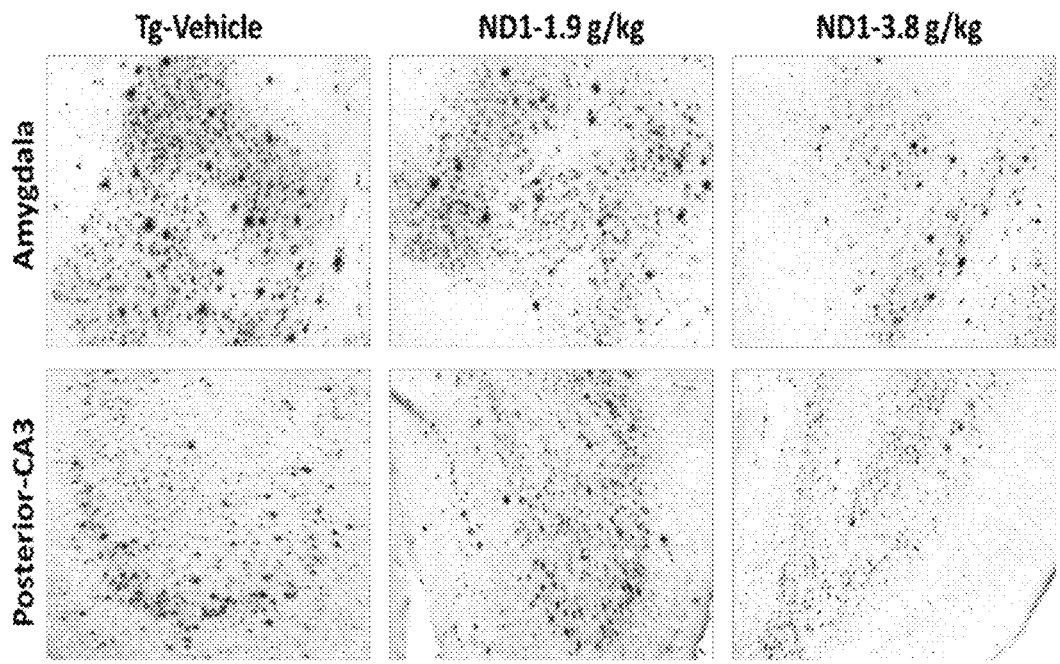
FIG. 8F shows ND1 reduces hippocampal Aβ-plaque burden in the brain of 5XFAD mice.
Figure 8G:
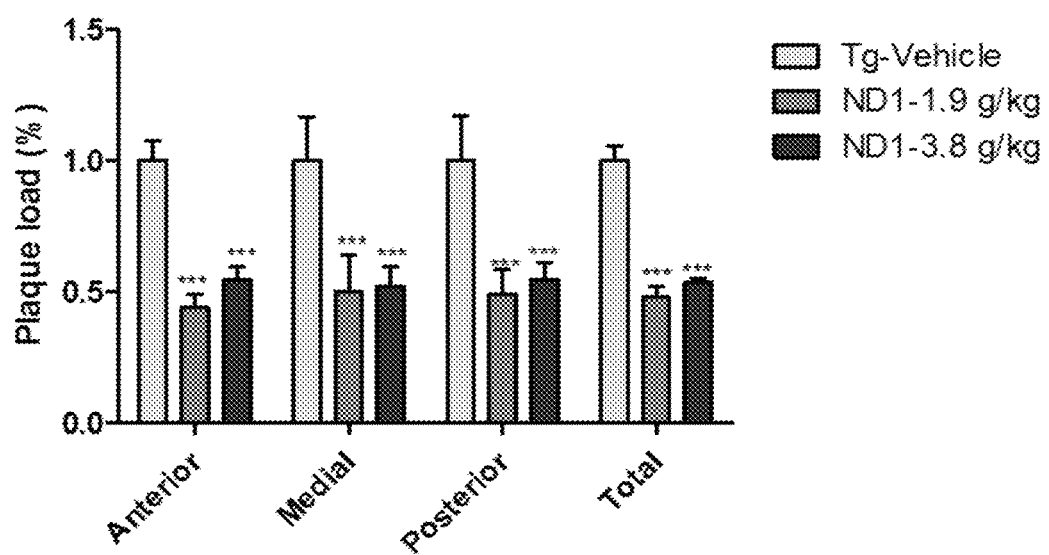
FIG. 8G shows the quantification of hippocampal Aβ-plaque burden in the brain of 5XFAD mice, the data are presented as the mean±SD.
Figure 8H:
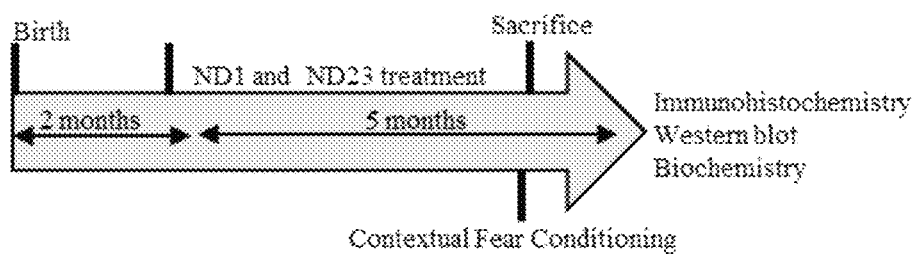
Figure 11A:
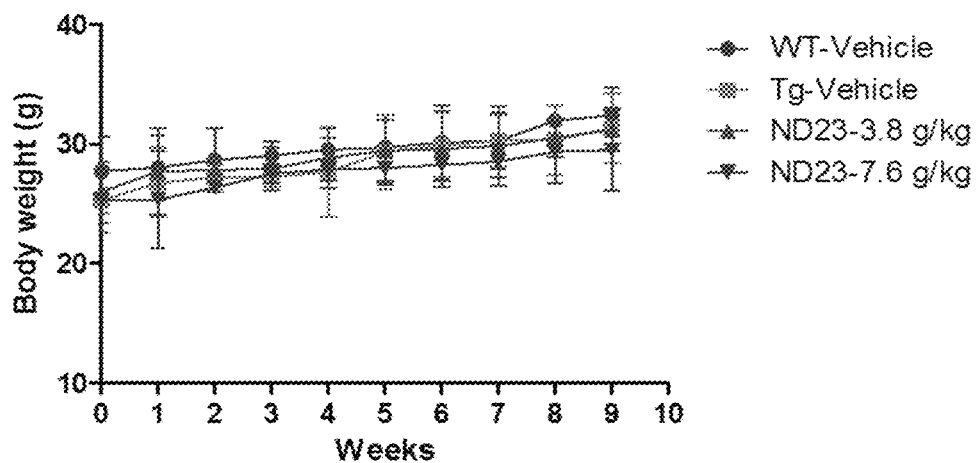
FIG. 11A shows ND23 does not influence the body weight in 5XFAD male mice.
Figure 11B:
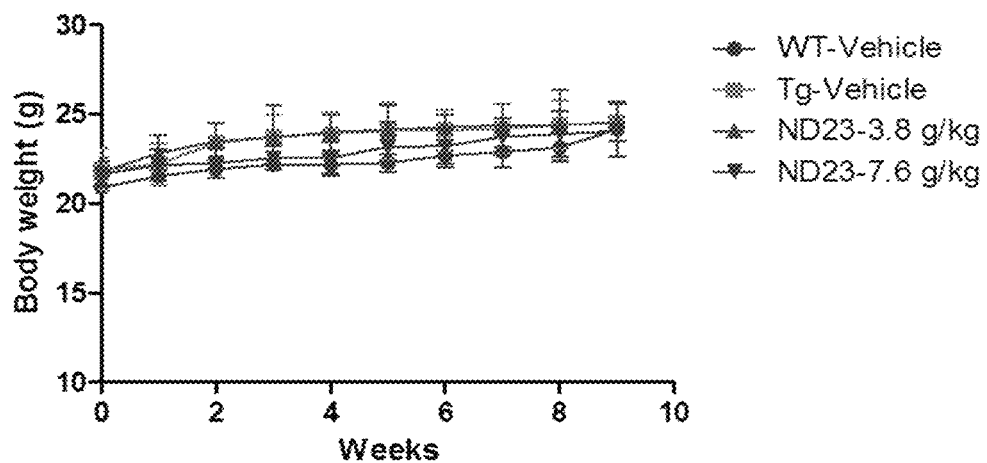
FIG. 11B shows ND23 does not influence the body weight in 5XFAD female mice.
Figure 11C:
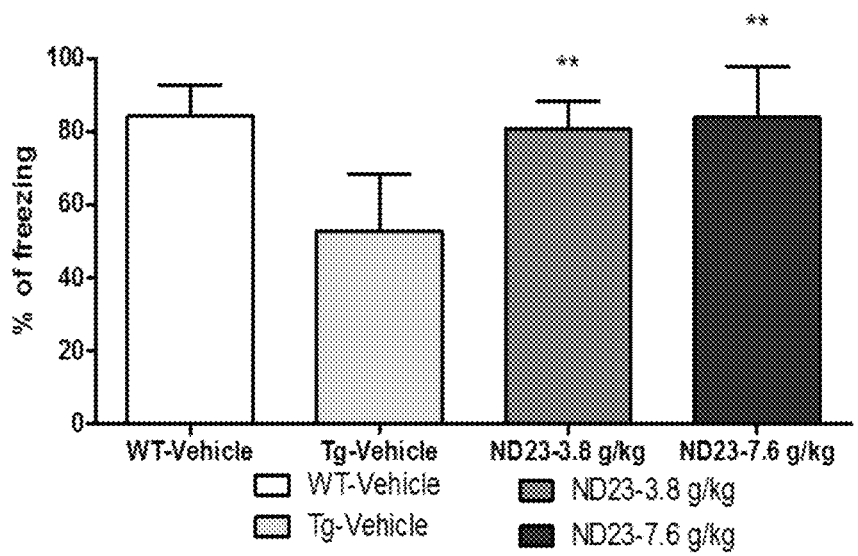
FIG. 11C shows ND23 ameliorates hippocampal and amygdala-dependent memory deficit in 5XFAD mice by contextual fear conditioning.
Figure 11D:
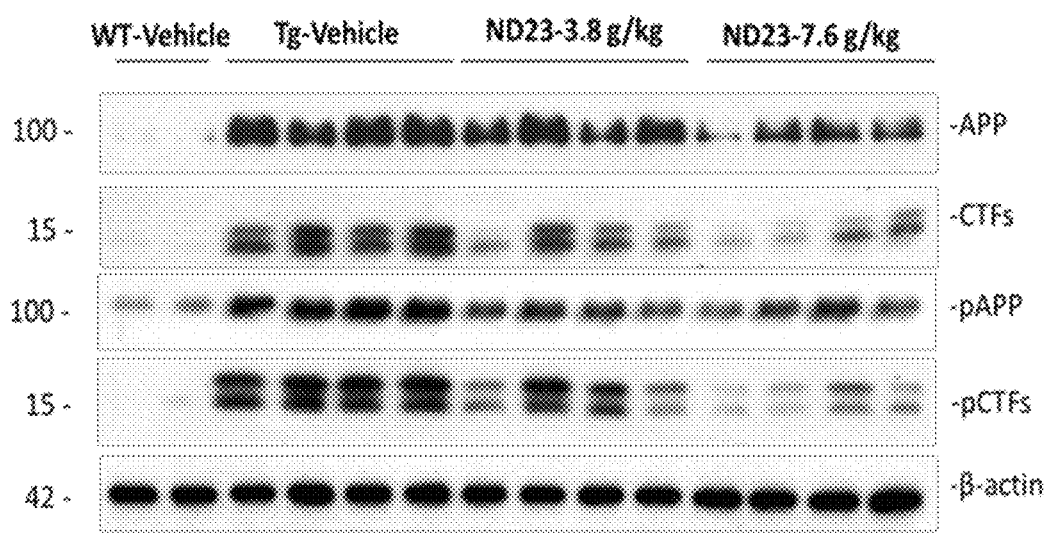
FIG. 11D shows ND23 significantly and dose-dependently reduced the levels of APP, CTFs, pAPP and pCTFs in the brain of 5XFAD mice by the western blot analysis.
Figure 11E:
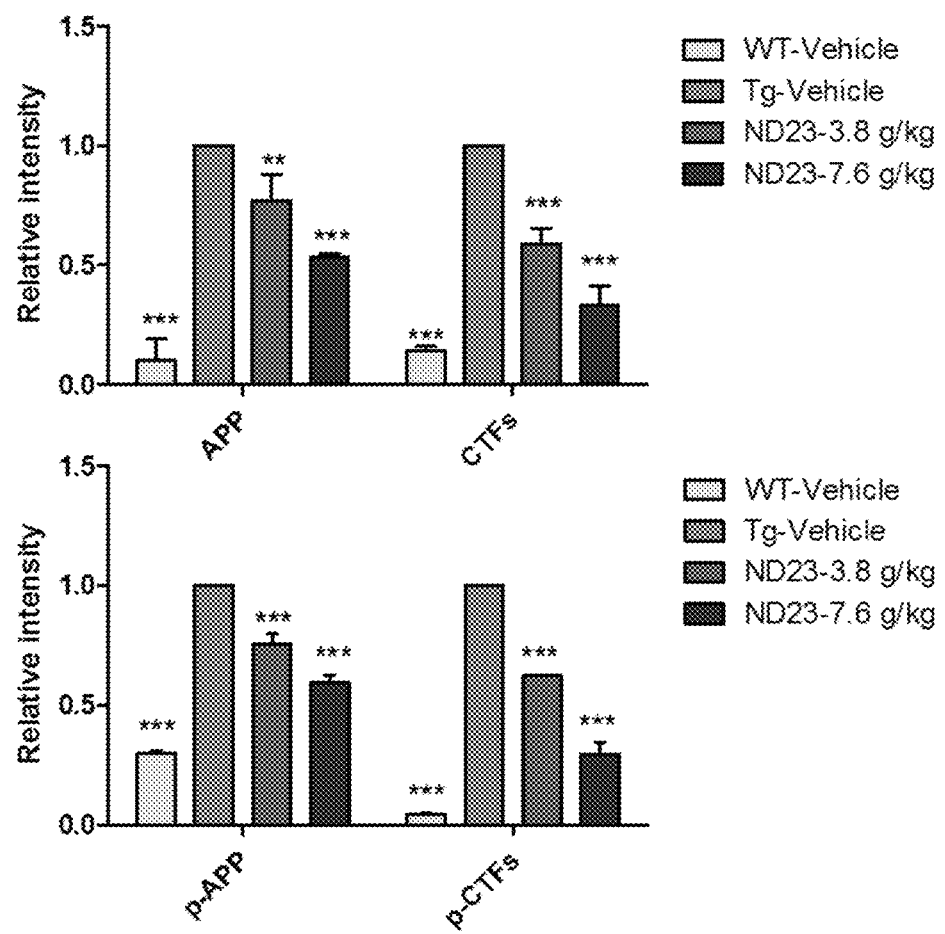
FIG. 11E shows the quantification of APP, CTFs, pAPP and pCTFs in the brain of 5XFAD mice by the western blot analysis. The data are presented as the mean±SD.
Figure 11F:
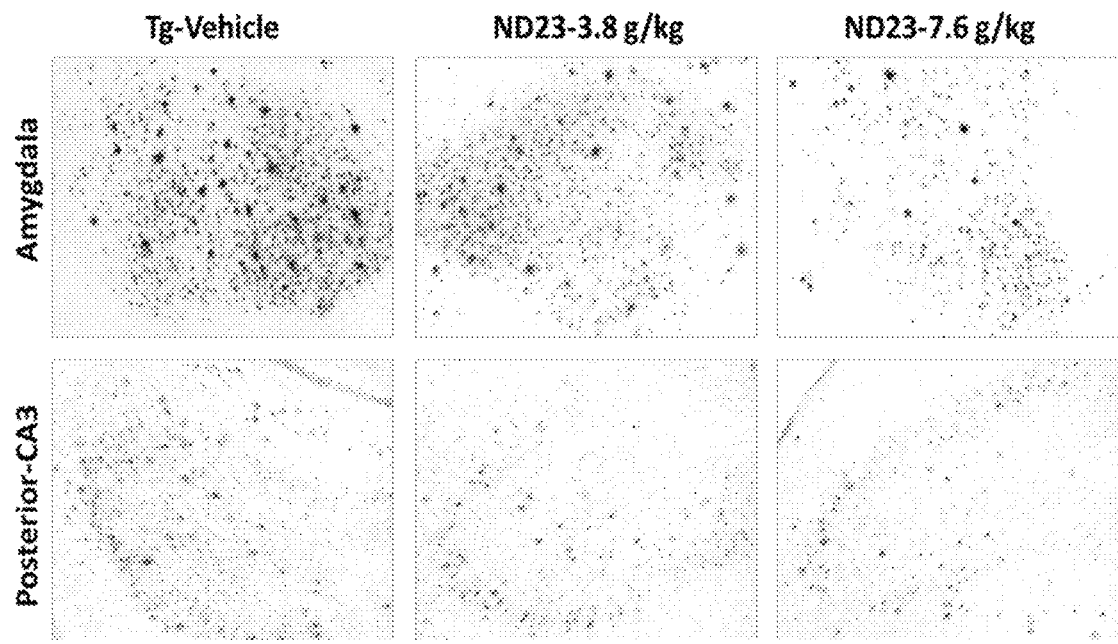
FIG. 11F shows ND23 reduces hippocampal Aβ-plaque burden in the brain of 5XFAD mice.
Figure 11G:
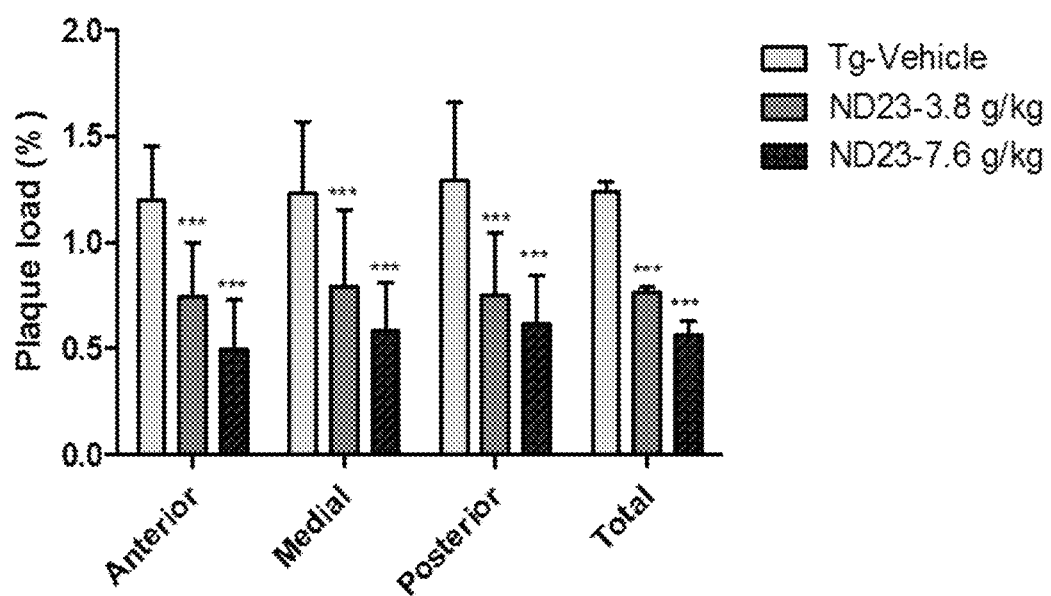
FIG. 11G shows the quantification of hippocampal Aβ-plaque burden in the brain of 5XFAD mice, the data are presented as the mean±SD.

Anti-AD Effect of ND1 and ND23 in 5XFAD Mouse Model:

The inventors further investigated Anti-AD effect and bioactivity of ND1 and ND23 in vivo to test the long-term effect of ND1 and ND23 on the Aβ reduction. The inventors carried out studies in 5X Familial Alzheimer's disease (5XFAD) mouse model because this model showed early aggressive Aβ accumulation. The inventors orally administered ND1 and ND23 as a food admixture in 2-month old 5XFAD mice with ND1 at a concentration of 1.9 g/kg and 3.8 g/kg per day and ND23 at a concentration of 3.8 g/kg and 7.6 g/kg per day until 5-months old (FIG. 8H). During the course of treatment, ND1 and ND23 did not influence both the male and female body weight (FIGS. 8A-8B, 11A-11B). At the end of 5 months of age, the hippocampal and amygdala-dependent memory deficit were tested by contextual fear conditioning. ND1 and ND23 ameliorates hippocampal and amygdala-dependent memory deficit in 5XFAD mice, ND1 and ND23 treated animals significantly froze more than vehicle-treated 5XFAD mice in freezing behavior and the auditory cue test (FIGS. 8C, 11C). Further the inventors performed the western blot analysis with the brain homogenate to detect SDS fraction of APP, CTFs, pAPP and pCTFs. The treatment with ND1 and ND23 significantly and dose-dependently reduced the levels of APP, CTFs, pAPP and pCTFs in the SDS fraction and such is confirmed by quantification of immunoblot by densitometric analysis (FIGS. 8D-8E, 11D-11E). To further confirm the Aβ-plaque pathology, the inventors performed immunohistochemistry in the 30 μm brain slices at different regions namely anterior, medial and posterior. The levels of intraneuronal Aβ plaques and the extracellular Aβ plaques were quantified in amygdala, CA1, CA2, CA3 and cortex regions. ND1 and ND23 reduced hippocampal Aβ-plaque burden in the 5XFAD mice brain (FIGS. 8F-8G, 11F-11G). These in vivo data confirm that use of ND1 and ND23 to reduce Aβ pathology and reverse cognitive dysfunction in AD.

Figure 9A:
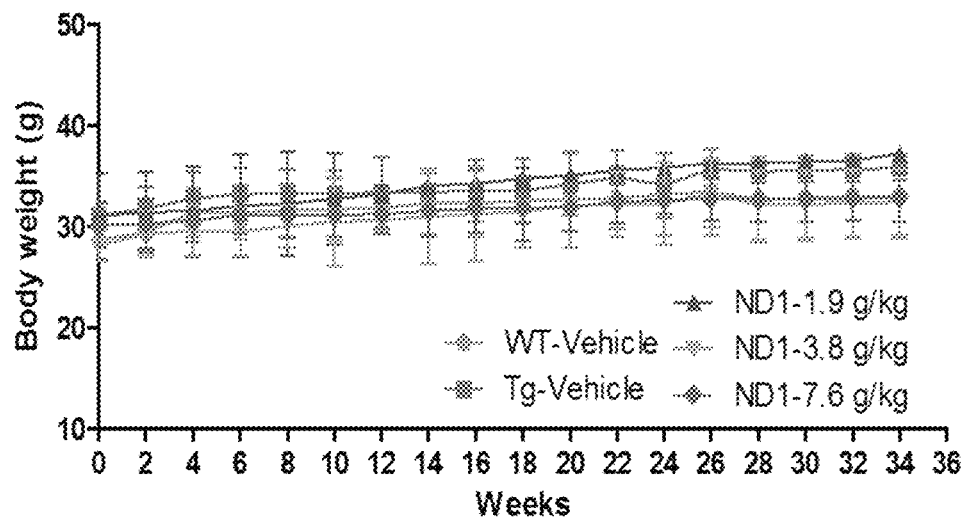
FIG. 9A shows ND1 does not influence the body weight in 3XTg-AD male mice.
Figure 9B:
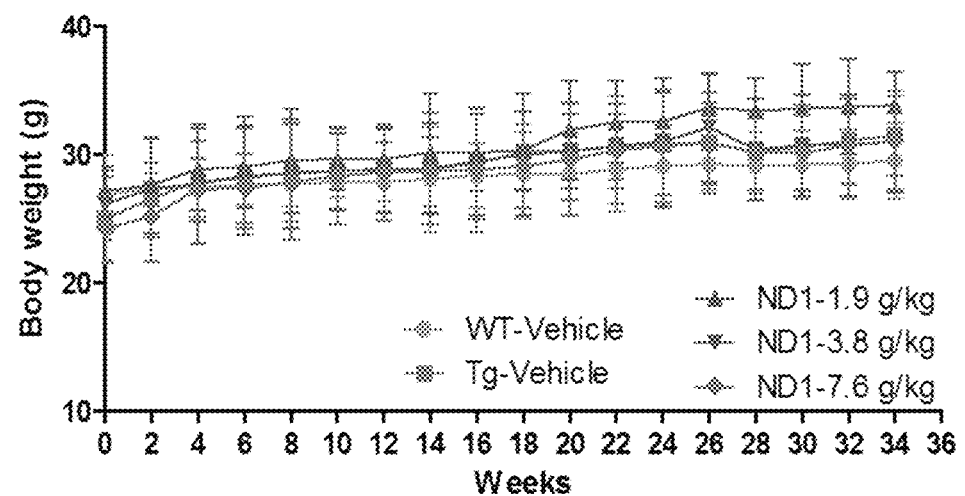
FIG. 9B shows ND1 does not influence the body weight in 3XTg-AD female mice.
Figure 9C:
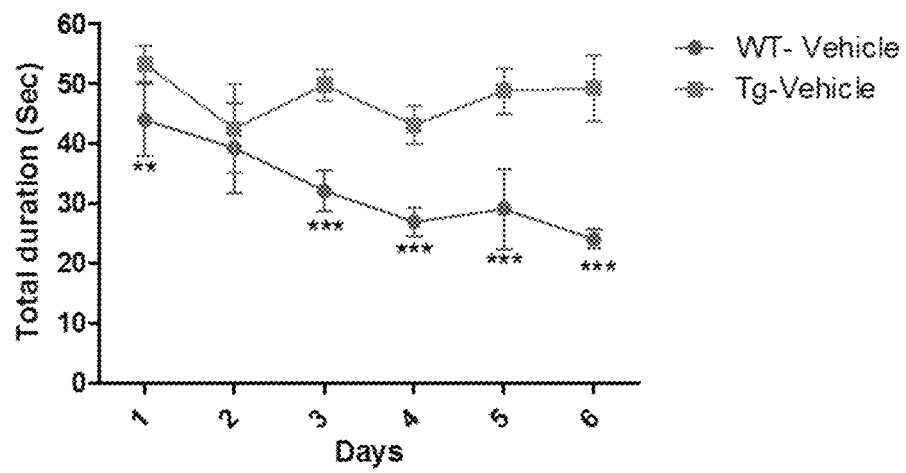
FIG. 9C shows the memory of wild type vehicle and Tg-vehicle groups during learning in Morris water maze experiment.
Figure 9D:
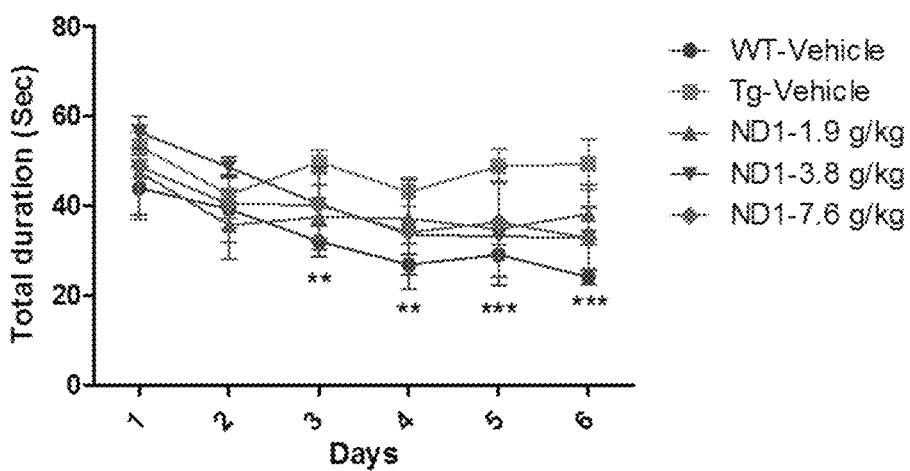
FIG. 9D shows ND1 ameliorates hippocampal-dependent memory deficit in 3XTg-AD mice during learning.
Figure 9E:
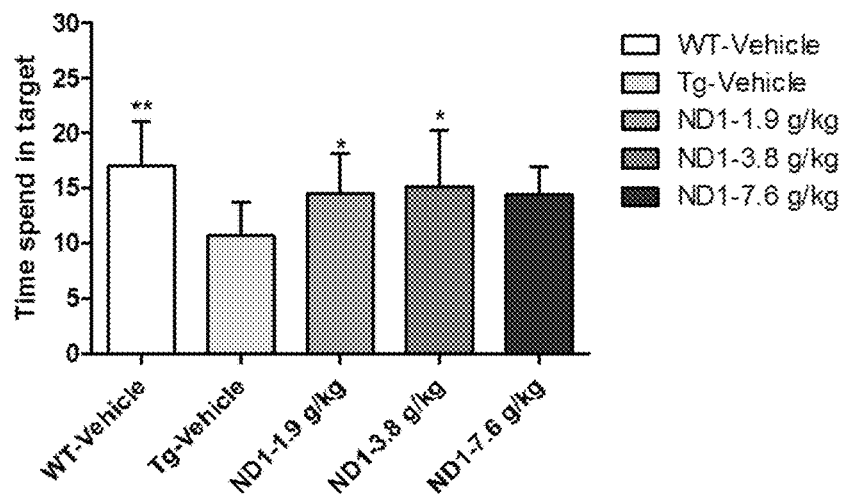
FIG. 9E shows the quantification of ND1 treated Tg group spent longer time in probing the platform in the target quadrant than the Tg-vehicle treated group in probe trial. The data are presented as the mean±SD.
Figure 9F:
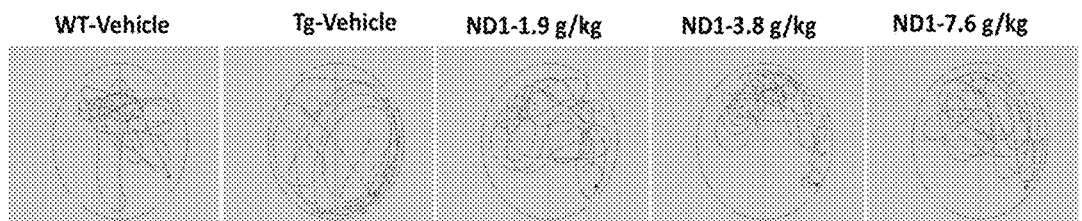
FIG. 9F shows the picture portraying memory retention of ND1 treated Tg group and the Tg-vehicle treated group in probe trial.
Figure 9G:
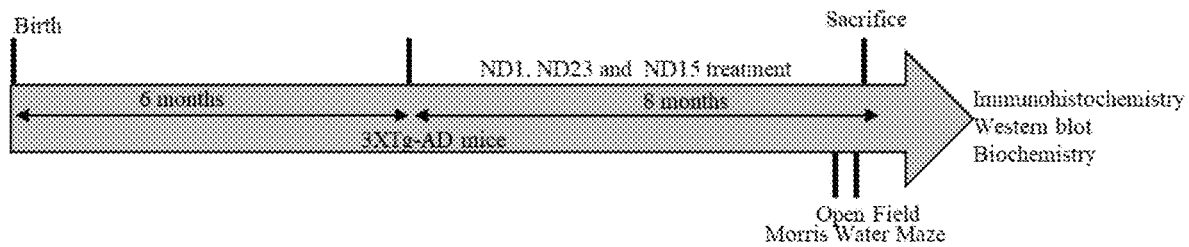
FIG. 9G shows the time line for ND treatment and behavior experiments schedule in 3XTg-AD mice.

Effect of ND1, ND23 and ND15 Treatment on Memory Deficit in 3XTg-AD Mouse Model:

The inventors further confirmed the role ND1, ND23 and ND15 on 3XTg-AD mice in the acquisition of spatial memory and learning. To evaluate the long-term effect of ND1, ND23 and ND15 on the amelioration of cognitive deficits, the inventors used 3X transgenic (3XTg)-AD mouse model because this model showed the late onset of symptom as similar as human. The inventors orally administered food admixture in 6-month old 3XTg-AD mice with ND1, ND23 and ND15 (1.9 g/kg/day, 3.8 g/kg/day, 7.6 g/kg/day) for 8 months (FIG. 9G). During the course of treatment ND1, ND23 and ND15 did not influence both the male and female animal body weight (FIGS. 9A-9B, 12A-12B, 14A-14B).

Figure 12A:
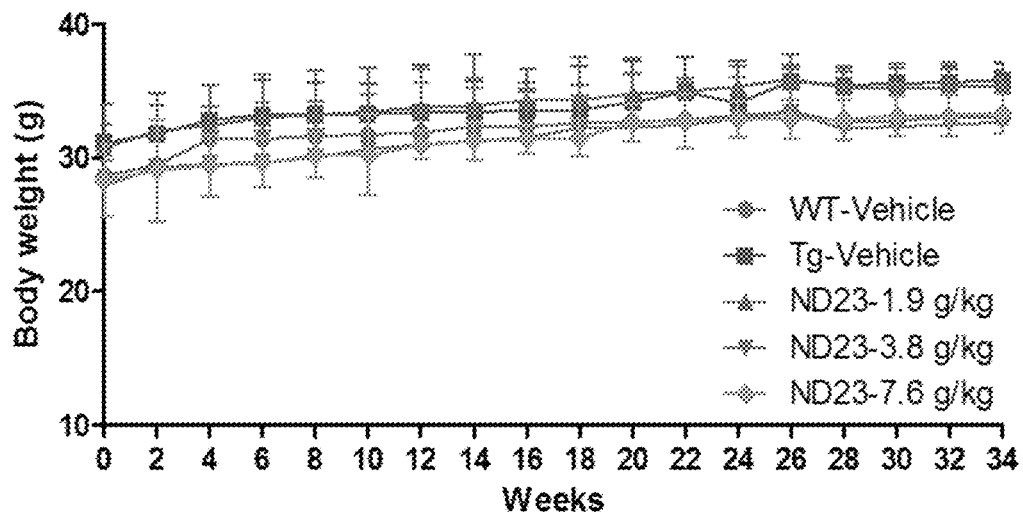
FIG. 12A shows ND23 does not influence the body weight in 3XTg-AD male mice.
Figure 12B:
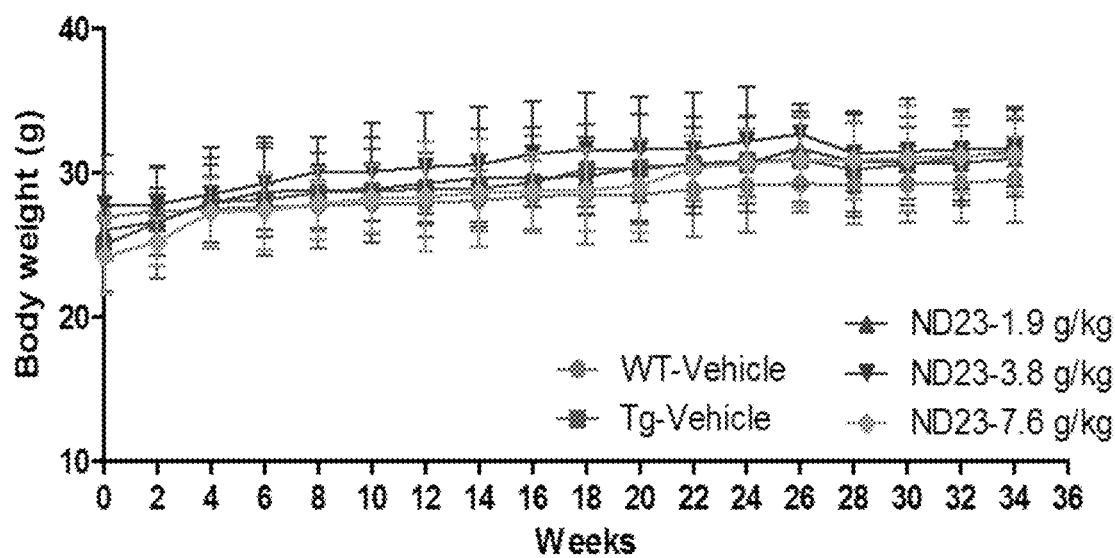
FIG. 12B shows ND23 does not influence the body weight in 3XTg-AD female mice.
Figure 12C:
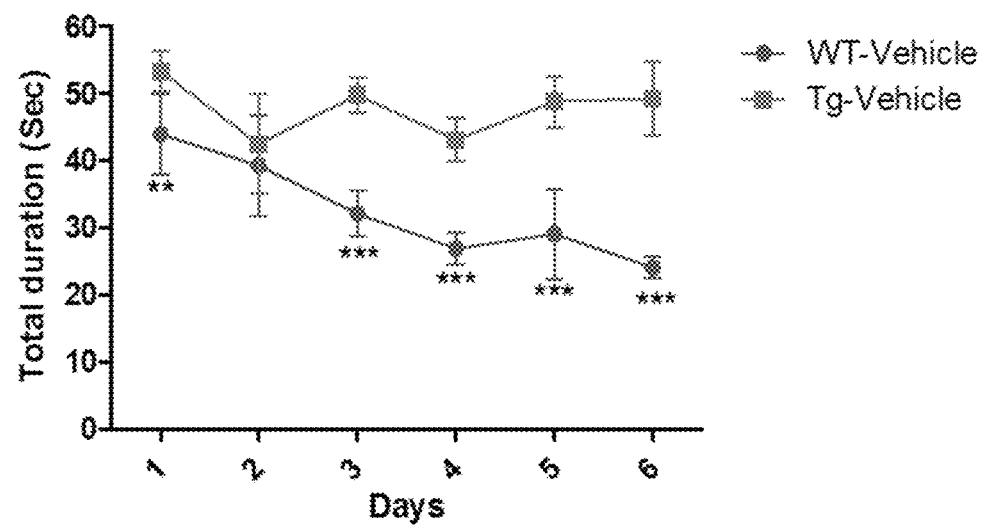
FIG. 12C shows the memory of wild type vehicle and Tg-vehicle groups during learning in the Morris water maze experiment.
Figure 12D:
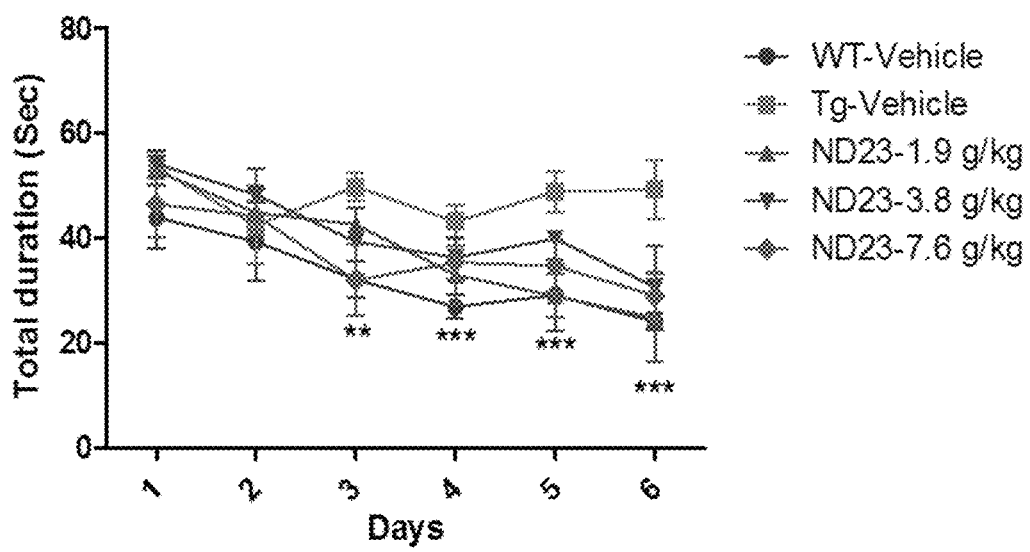
FIG. 12D shows ND23 ameliorates hippocampal-dependent memory deficit in 3XTg-AD mice during learning.
Figure 12E:
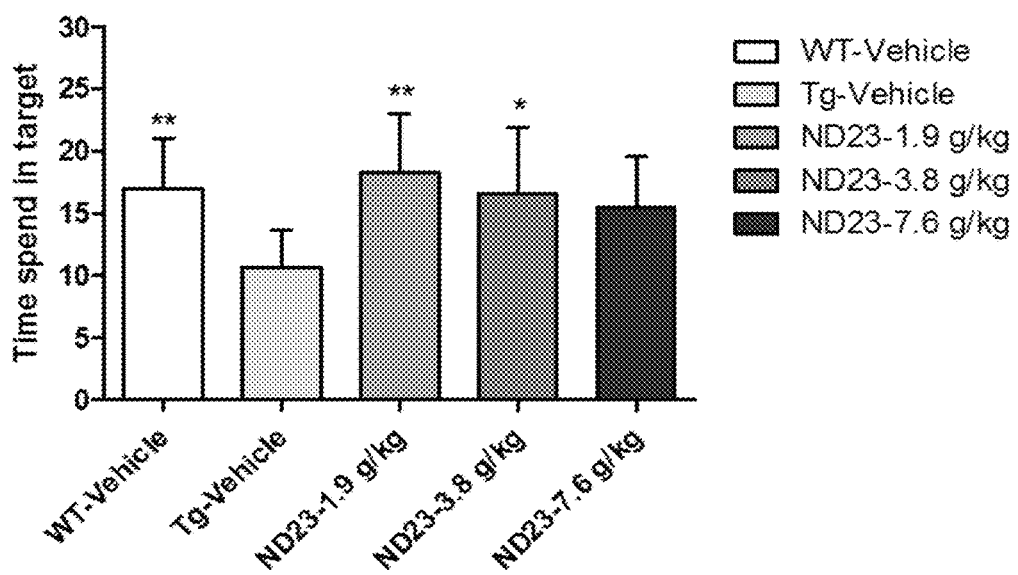
FIG. 12E shows the quantification of ND23 treated Tg group spent longer time in probing the platform in the target quadrant than the Tg-vehicle treated group in probe trial, the data are presented as the mean±SD.
Figure 12F:
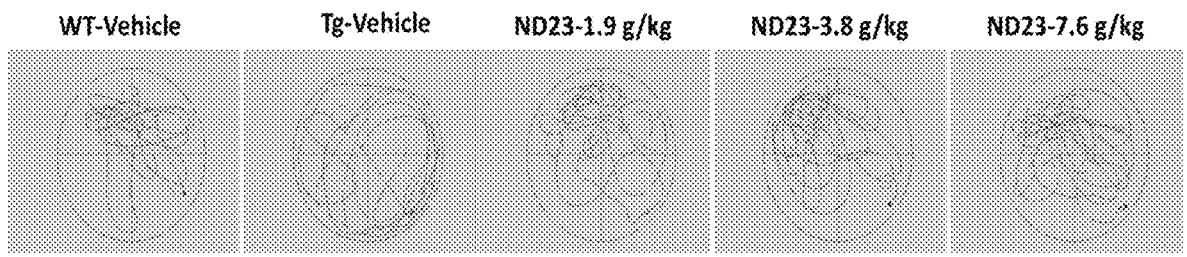
FIG. 12F shows the picture portraying memory retention of ND23 treated Tg group and the Tg-vehicle treated group in probe trial.
Figure 14A:
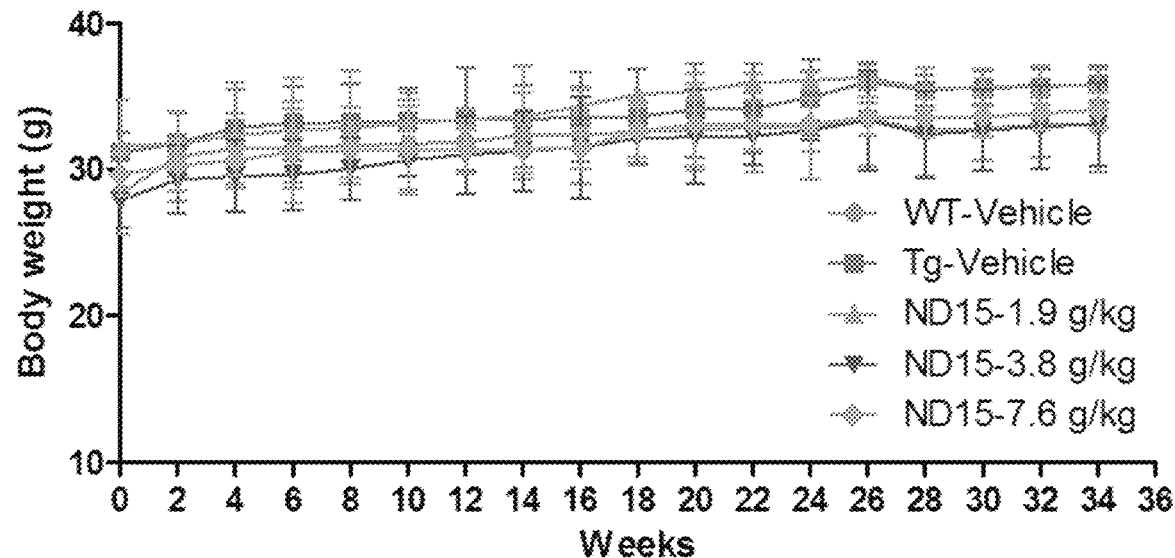
FIG. 14A shows ND15 does not influence the body weight in 3XTg-AD male mice.
Figure 14B:
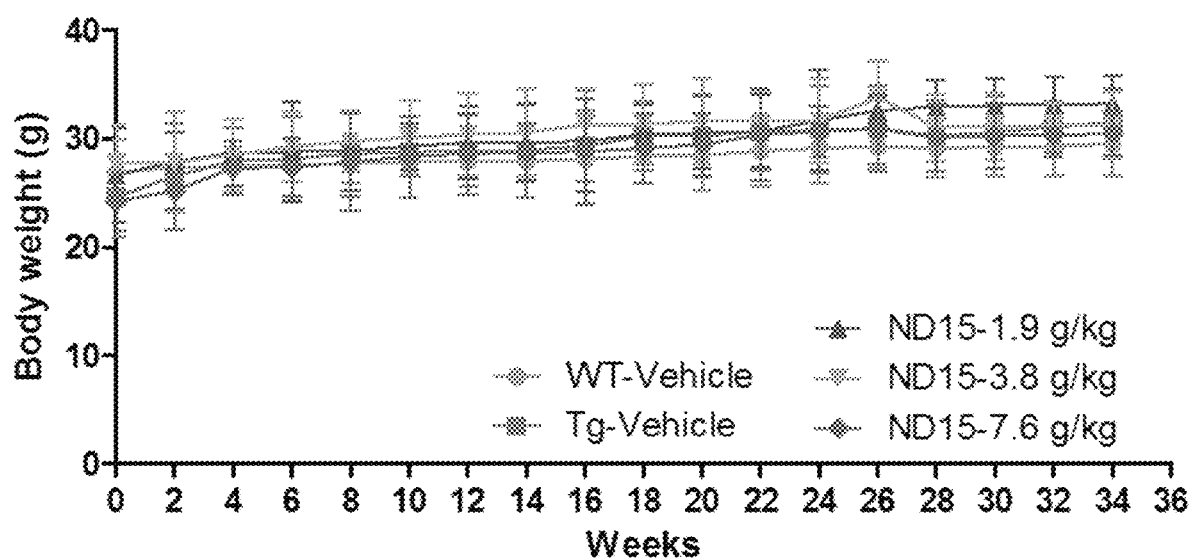
FIG. 14B shows ND15 does not influence the body weight in 3XTg-AD female mice.
Figure 14C:
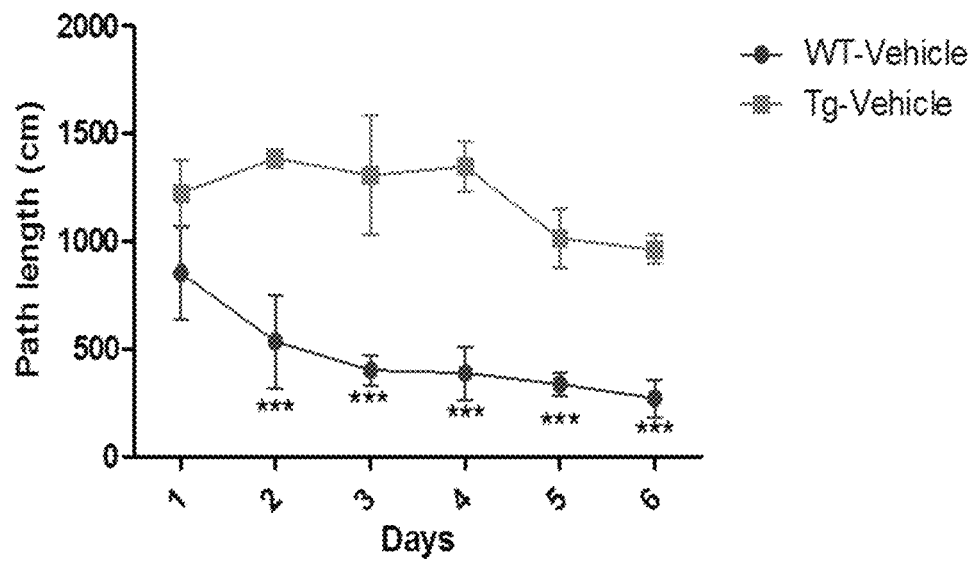
FIG. 14C shows the memory of wild type vehicle and Tg-vehicle groups during learning in the Morris water maze experiment.
Figure 14D:
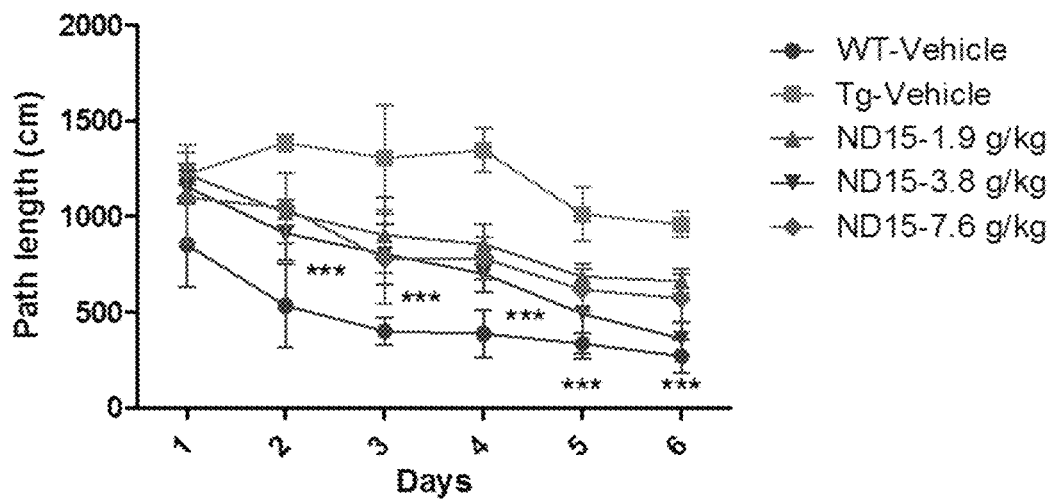
FIG. 14D shows ND15 ameliorates hippocampal-dependent memory deficit in 3XTg-AD mice during learning.
Figure 14E:
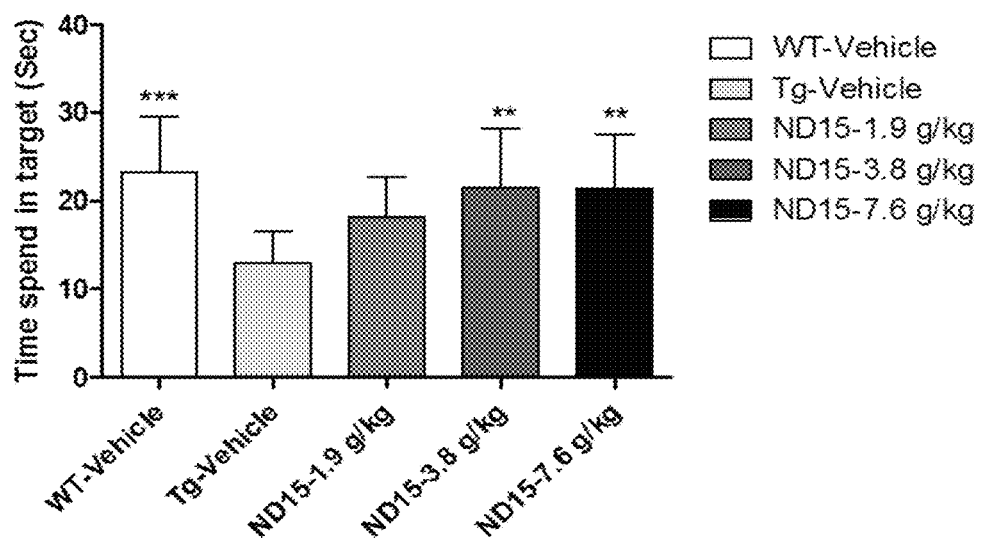
FIG. 14E shows the quantification of ND15 treated Tg group spent longer time in probing the platform in the target quadrant than the Tg-vehicle treated group, the data are presented as the mean±SD.
Figure 14F:
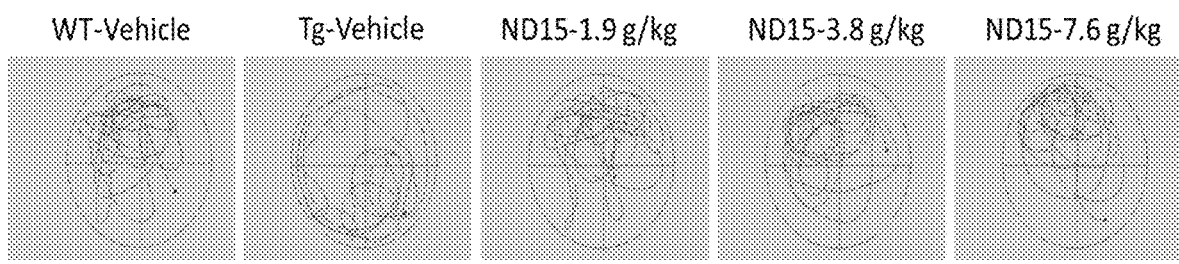
FIG. 14F shows the picture portraying memory retention of ND15 treated Tg group and the Tg-vehicle treated group in probe trial.

Further to evaluate the long-term effect of ND1, ND23 and ND15 on the amelioration of cognitive deficits in 3XTg-AD mice, the inventors performed Morris water maze experiment. Acquisition of spatial memory, learning and memory retention were evaluated in the ND1, ND23 and ND15 treated 3XTg-AD mice, the acquisition of data during a 6 days-training in the Morris water maze was to analyze the escape latencies of the ND1, ND23 and ND15 treated 3XTg-AD mice during the training period. All groups learned to locate the platform during 6 days of training, as indicated by decreasing escape latencies as training progressed, the escape latencies of ND1, ND23 and ND15 treated groups during 6 day training exhibited significantly shorter travel distance than those of transgenic (Tg) vehicle group (FIG. 9D, 12D, 14D). Further in the acquisition phase of learning, the wild type (WT) groups exhibited significantly shorter travel distance in training than those of Tg placebo group (FIGS. 9C, 12C, 14C). To test the memory retention in ND1, ND23, ND15 treated and Tg-vehicle treatment groups, the inventors executed a probe trial 24 hours after the 6th day training. On the probe trial day ND1, ND23 and ND15 treated group (FIG. 9E, 12E, 14E) spent longer time in probing the platform in the target quadrant than the Tg-vehicle treated group (FIG. 9F, 12F, 14F). Further the inventors conclude that memory retention and learning improved in ND1, ND23 and ND15 treatment groups of 3XTg-AD mice compared to the Tg-Vehicle.

Quantification of Pharmacokinetics of ND1, ND23, ND15 in ICR Mice

Figure 15A:
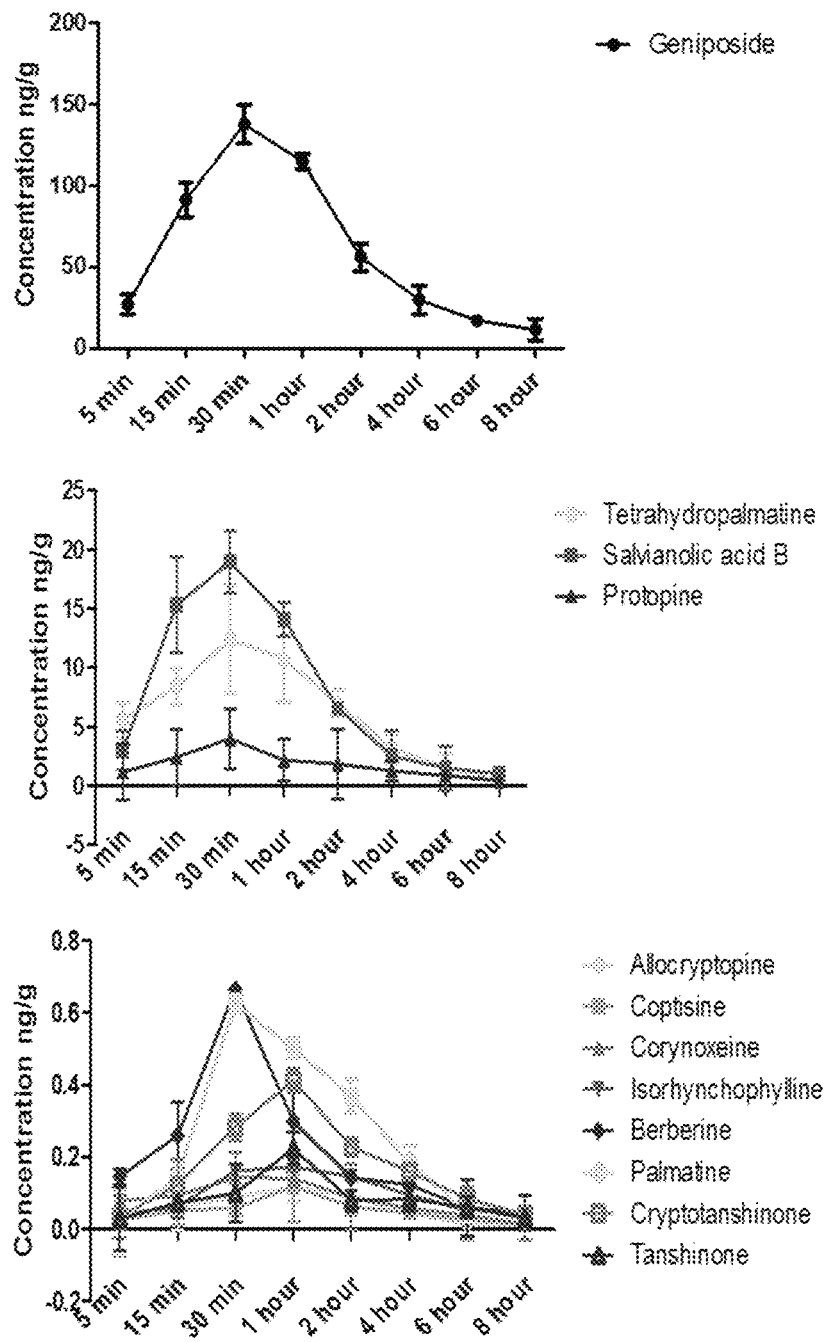
FIG. 15A shows the pharmacokinetic quantitative analysis of ND1 brain permeable bioactive components in ICR mice by LC MS.
Figure 15B:
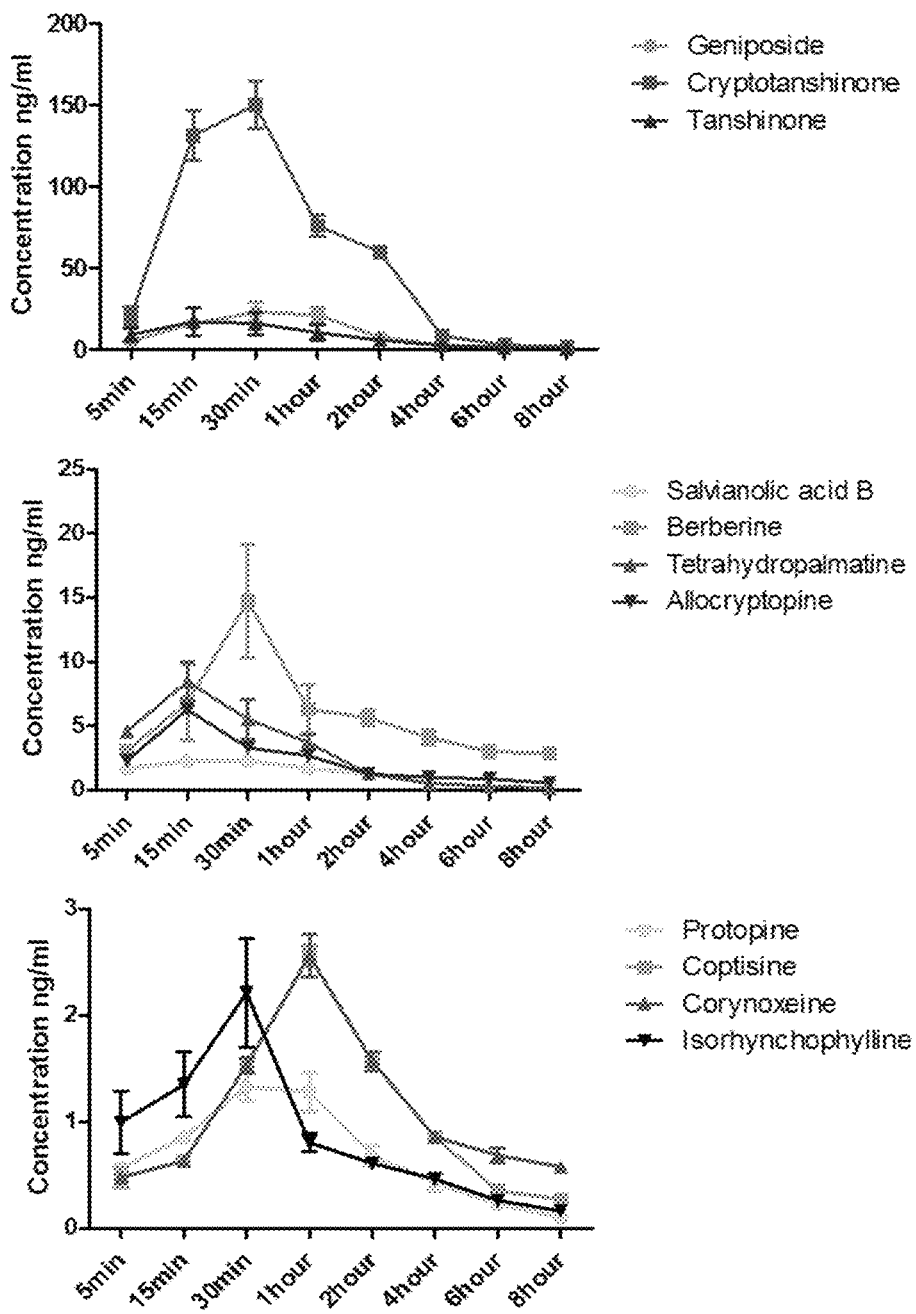
FIG. 15B shows the pharmacokinetic quantitative analysis of ND1 bioactive components in plasma of ICR mice by LC MS.
Figure 16A:
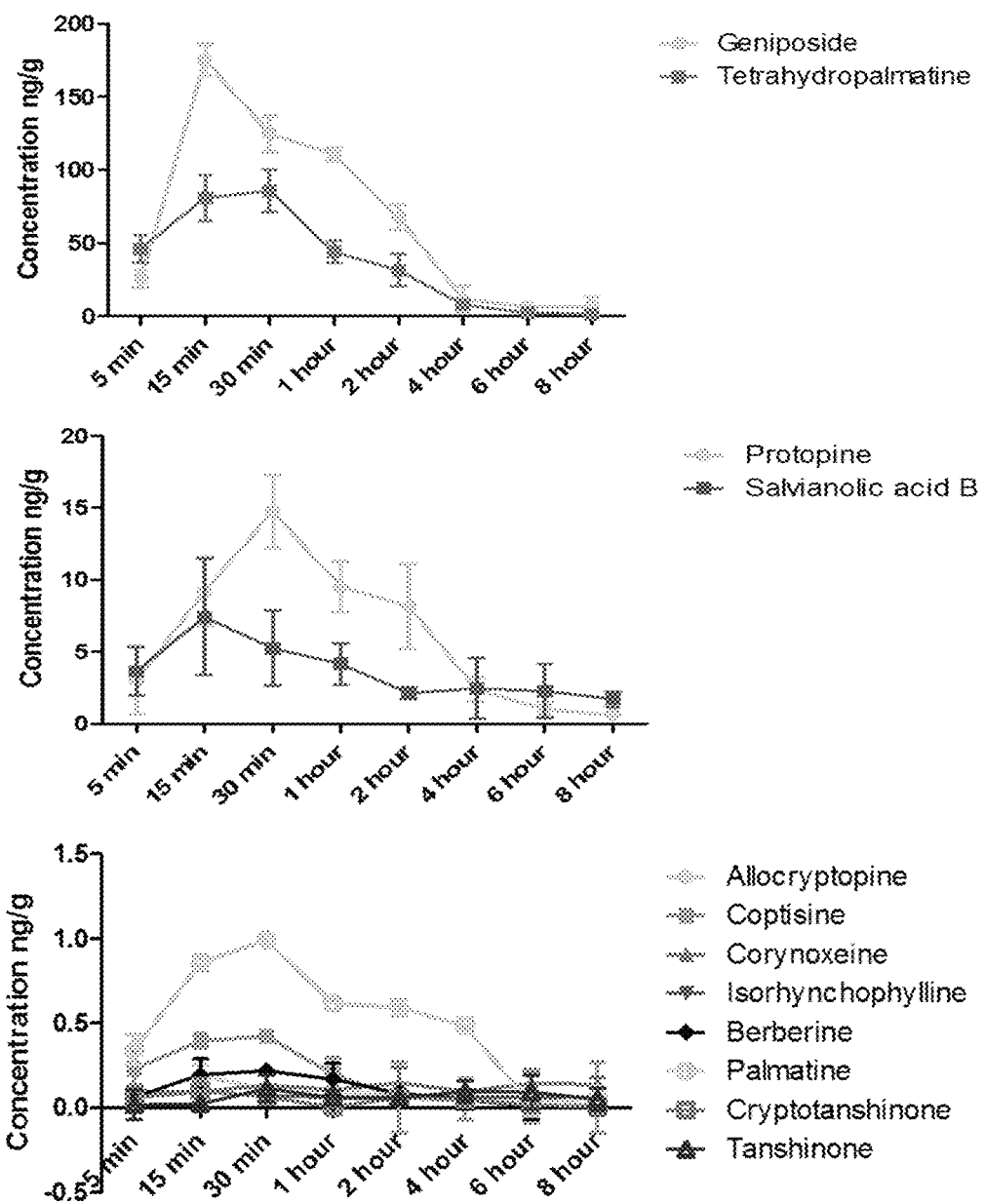
FIG. 16A shows the pharmacokinetic quantitative analysis of ND23 brain permeable bioactive components in ICR mice by LC MS.
Figure 16B:
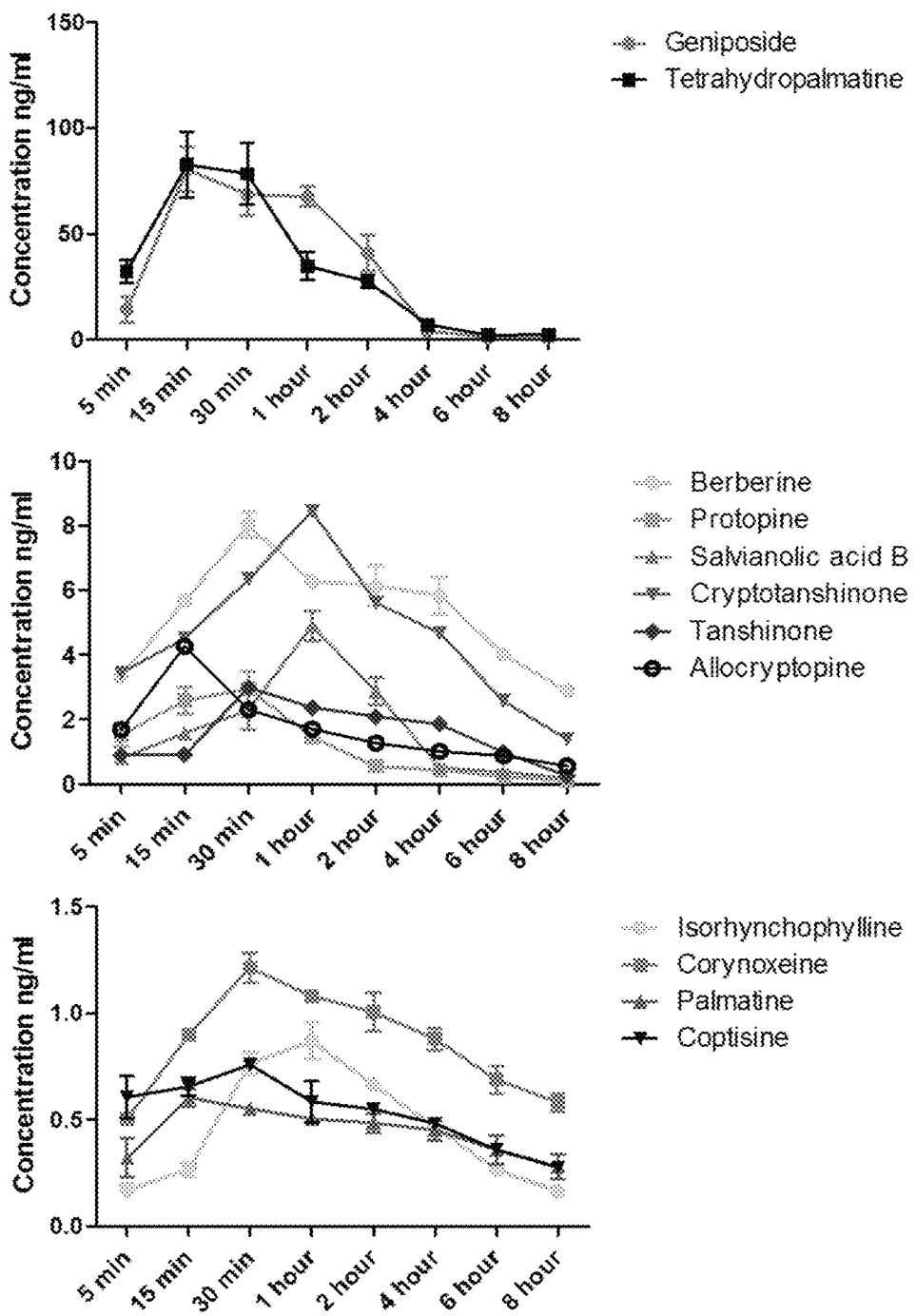
FIG. 16B shows the pharmacokinetic quantitative analysis of ND23 bioactive components in plasma of ICR mice by LC MS.
Figure 17A:
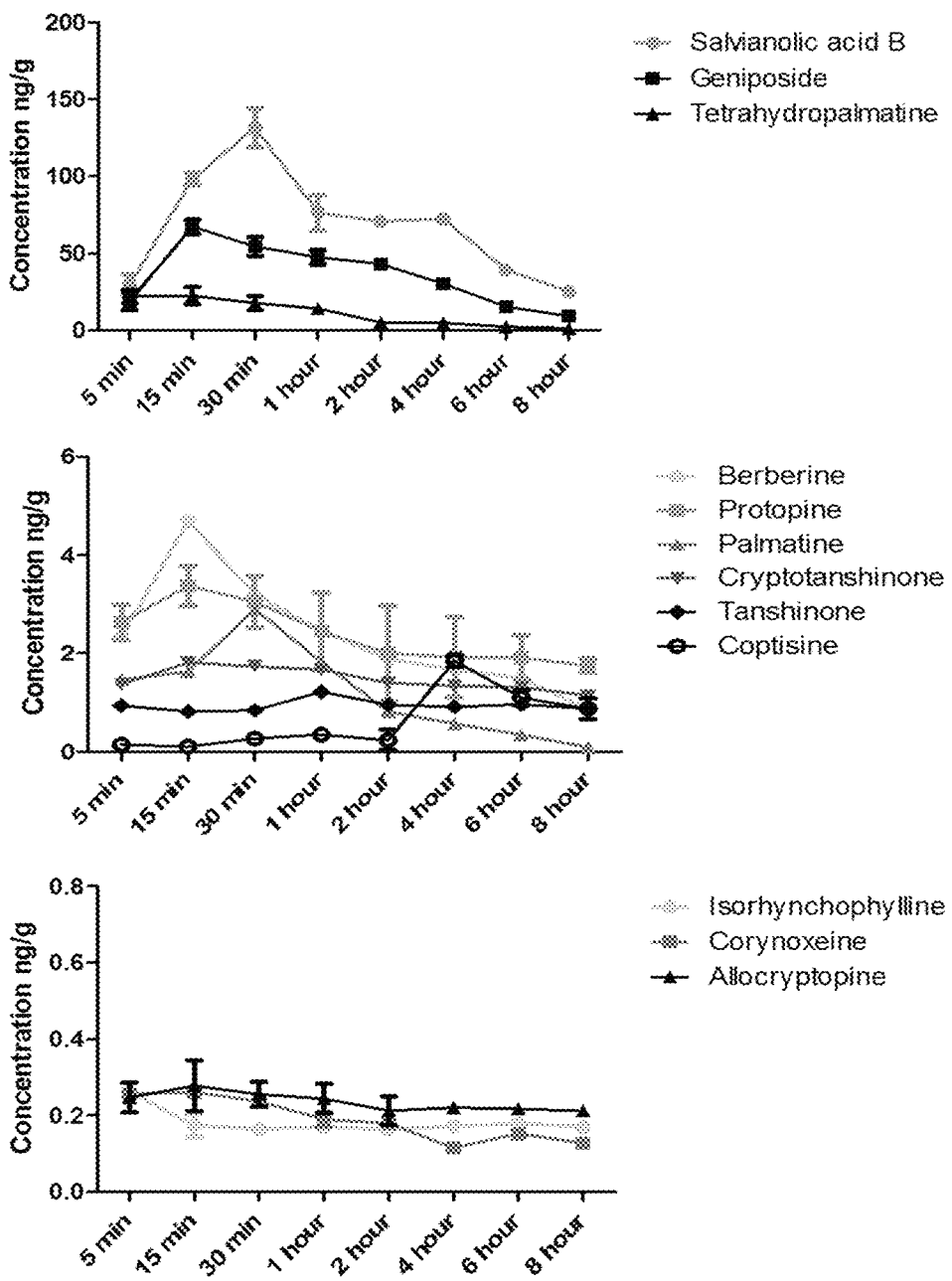
FIG. 17A shows the pharmacokinetic quantitative analysis of ND15 brain permeable bioactive components in ICR mice by LC MS.
Figure 17B:
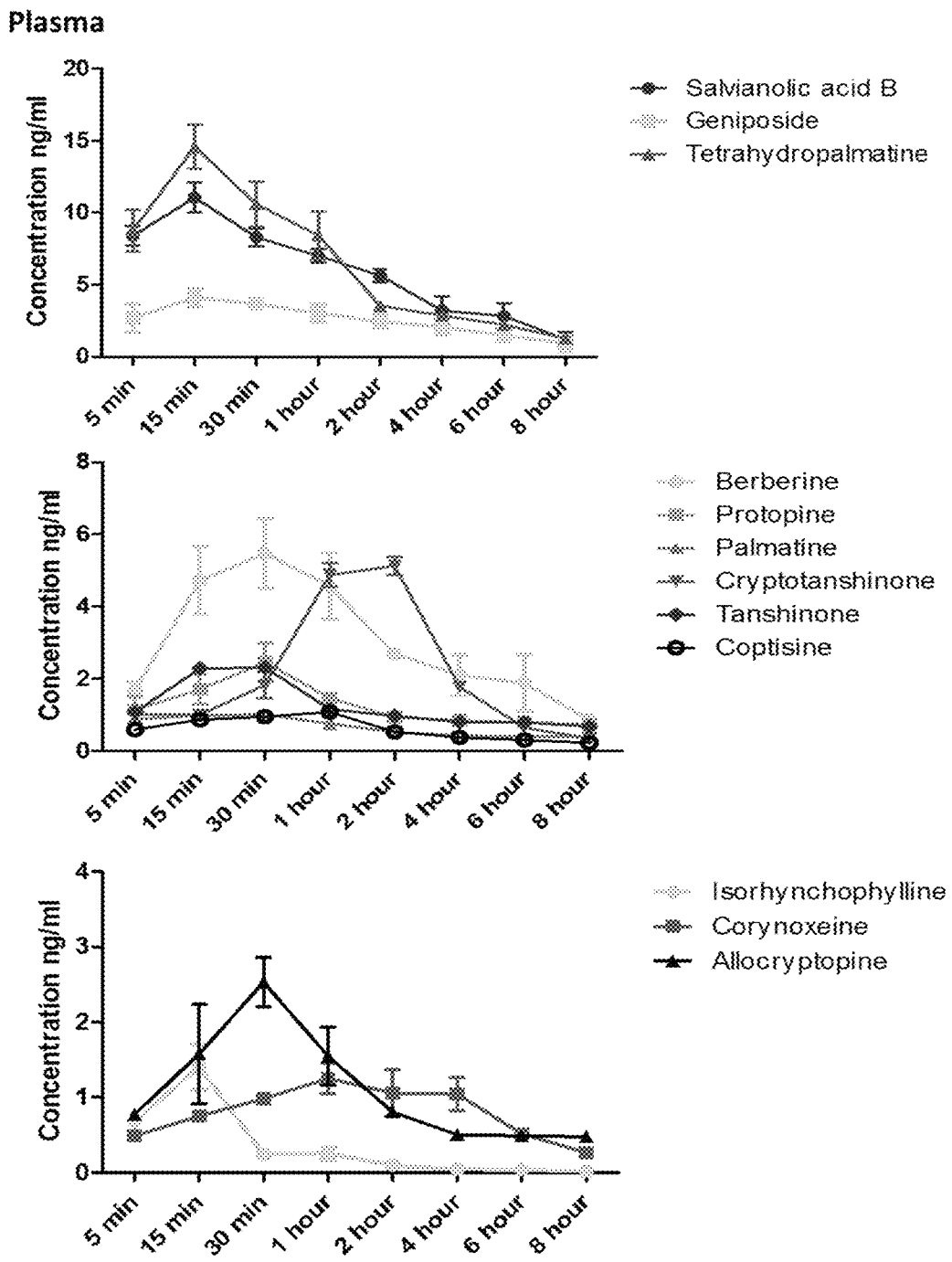
FIG. 17B shows the pharmacokinetic quantitative analysis of ND15 bioactive components in plasma of ICR mice by LC MS.
Figure 18A:
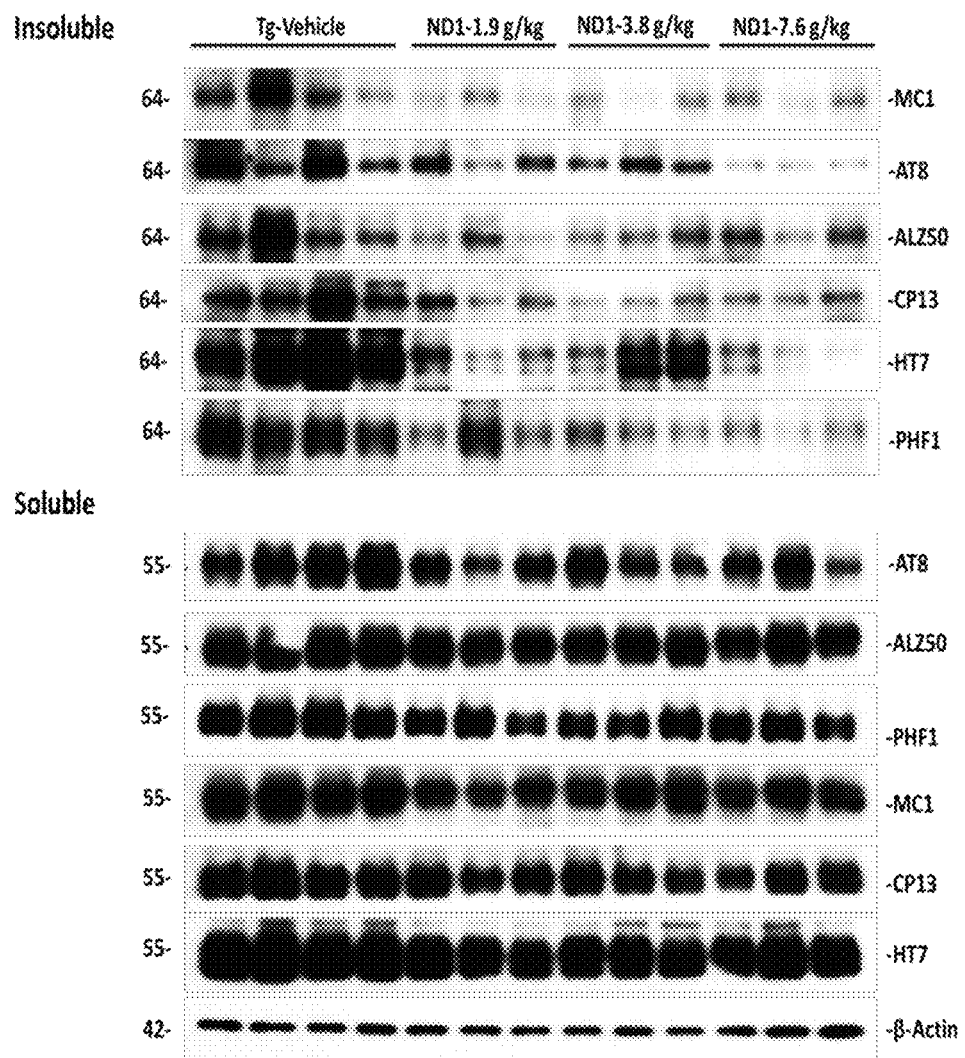
FIG. 18A shows ND1 reduced the levels of insoluble phosphorylated, misfolded and total tau in 3XTg-AD mice by western blot.
Figure 18B:
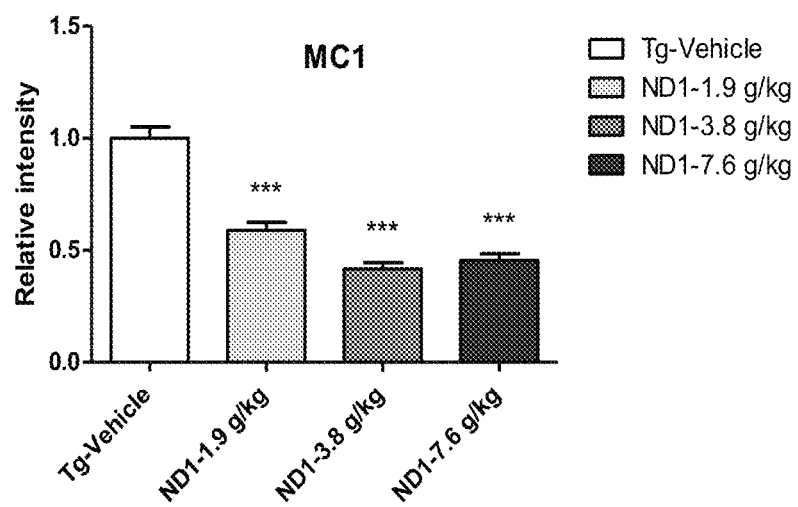
FIG. 18B shows the quantitative analysis of the ND1 treated 3XTg-AD animal's insoluble tau levels are detected using MC1 antibodies.
Figure 18C:
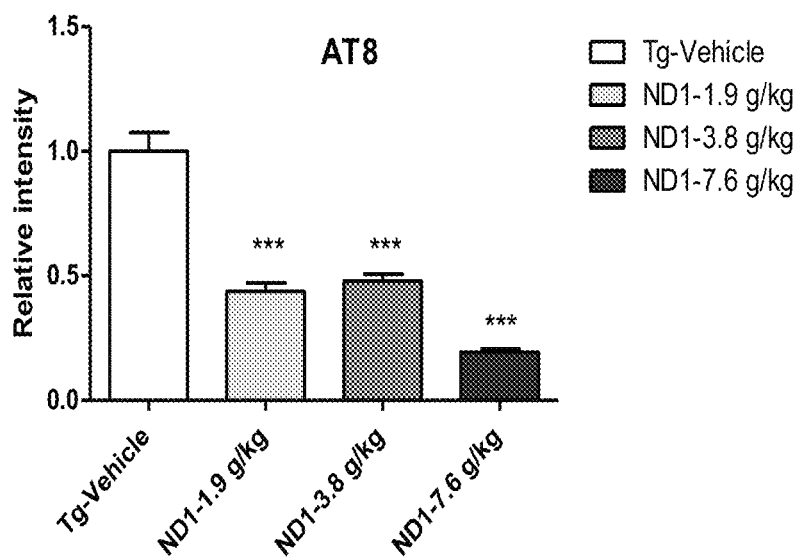
FIG. 18C shows the quantitative analysis of the ND1 treated 3XTg-AD animal's insoluble tau levels are detected using AT8 antibodies.
Figure 18D:
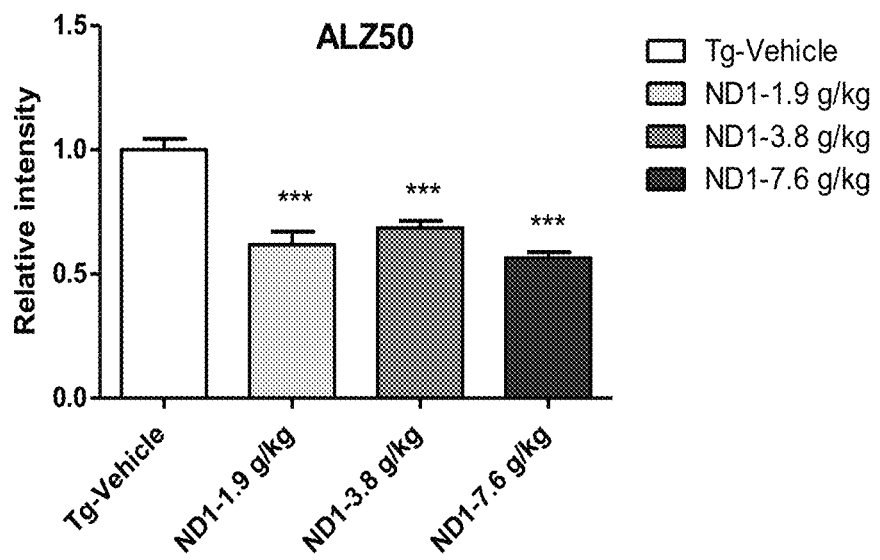
FIG. 18D shows the quantitative analysis of the ND1 treated 3XTg-AD animal's insoluble tau levels are detected using ALZ50 antibodies.
Figure 18E:
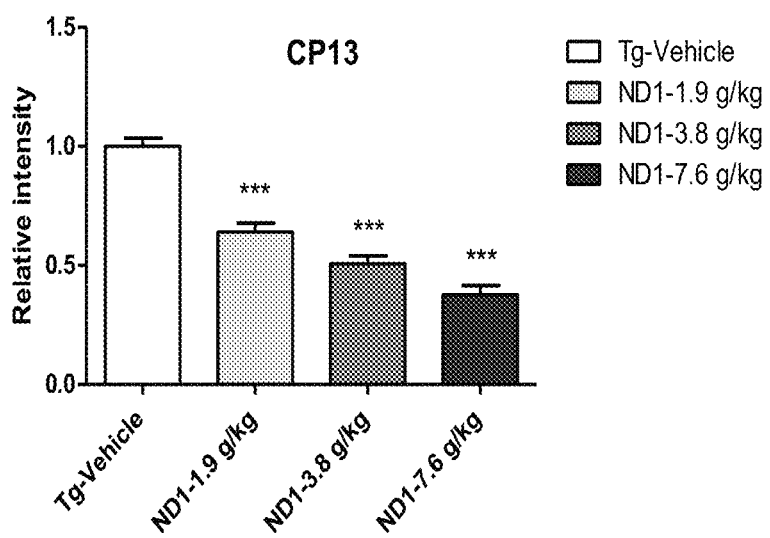
FIG. 18E shows the quantitative analysis of the ND1 treated 3XTg-AD animal's insoluble tau levels are detected using CP13 antibodies.
Figure 18F:
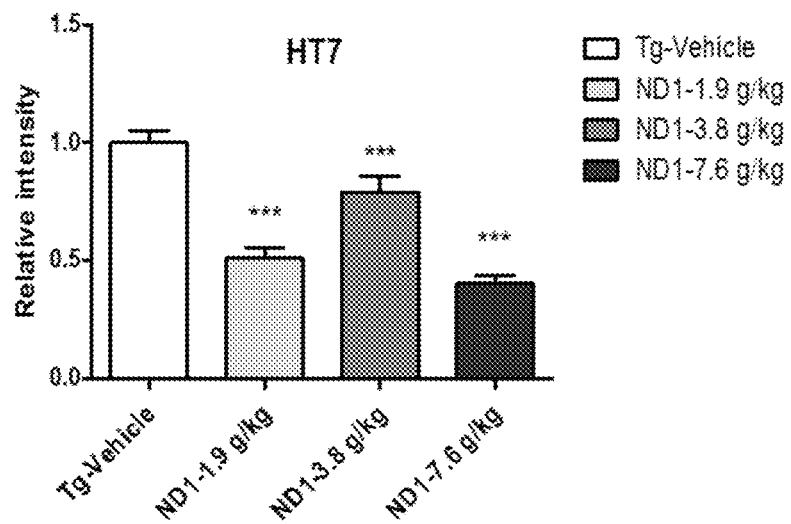
FIG. 18F shows the quantitative analysis of the ND1 treated 3XTg-AD animal's insoluble tau levels are detected using HT7 antibodies.
Figure 18G:
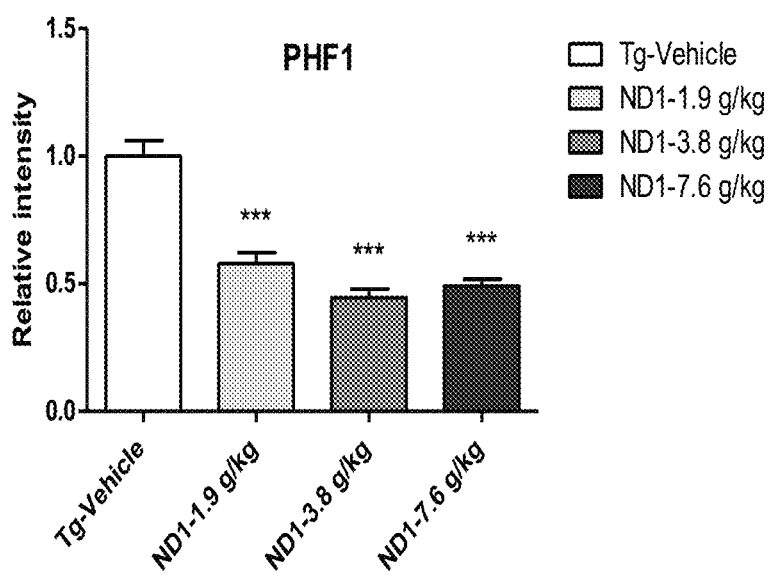
FIG. 18G shows the quantitative analysis of the ND1 treated 3XTg-AD animal's insoluble tau levels are detected using PHF1 antibodies.
Figure 19A:
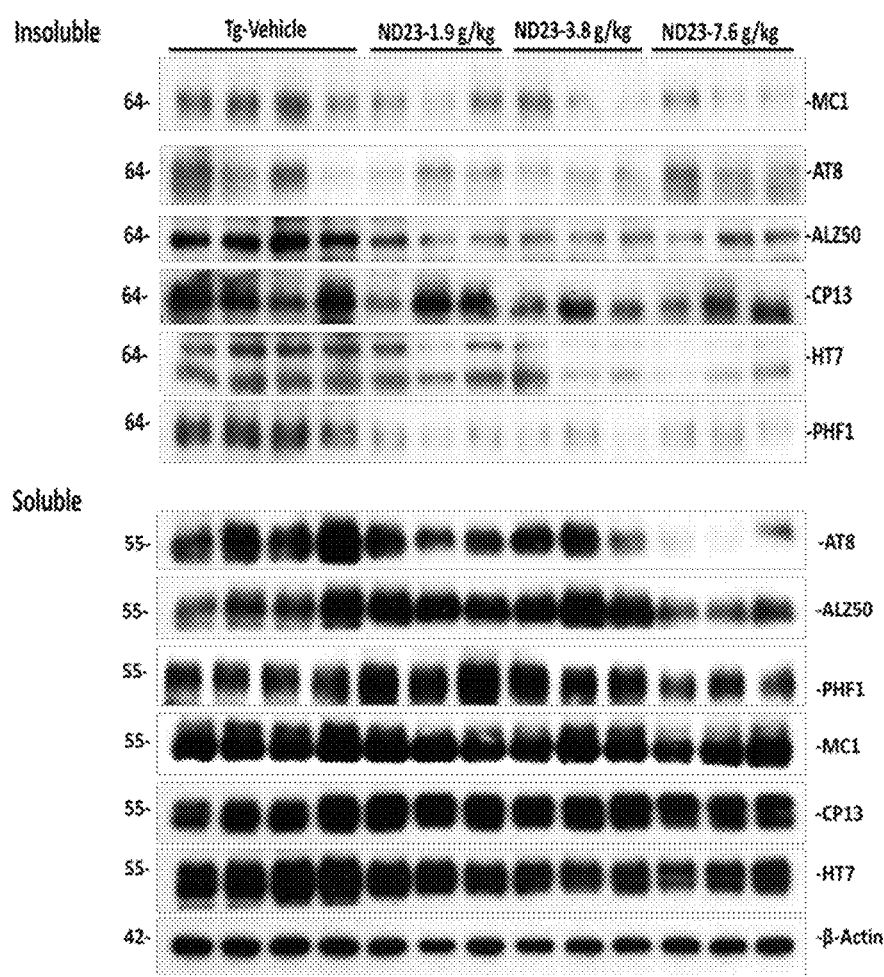
FIG. 19A shows ND23 reduced the levels of insoluble phosphorylated, misfolded and total tau in 3XTg-AD mice by western blot.
Figure 19B:
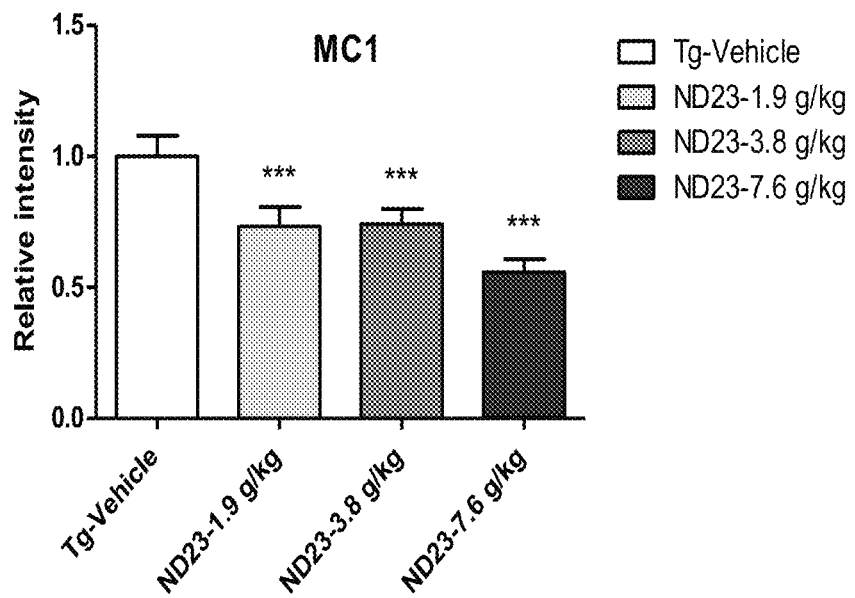
FIG. 19B shows the quantitative analysis of the ND23 treated 3XTg-AD animal's insoluble tau levels are detected using MC1 antibodies.
Figure 19C:
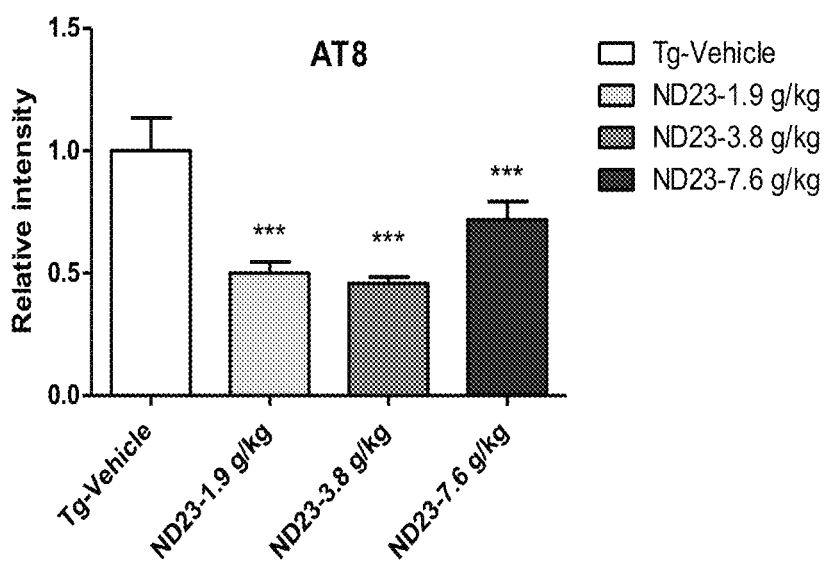
FIG. 19C shows the quantitative analysis of the ND23 treated 3XTg-AD animal's insoluble tau levels are detected using AT8 antibodies.
Figure 19D:
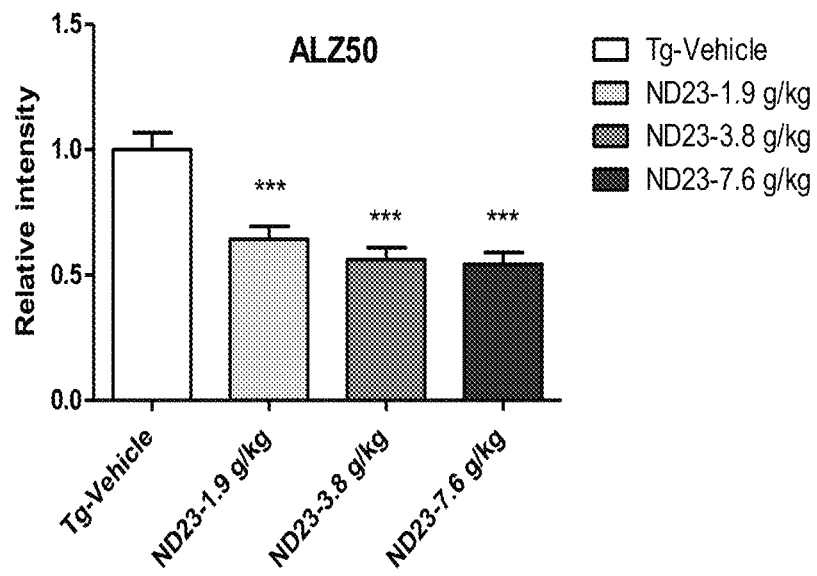
FIG. 19D shows the quantitative analysis of the ND23 treated 3XTg-AD animal's insoluble tau levels are detected using ALZ50 antibodies.
Figure 19E:
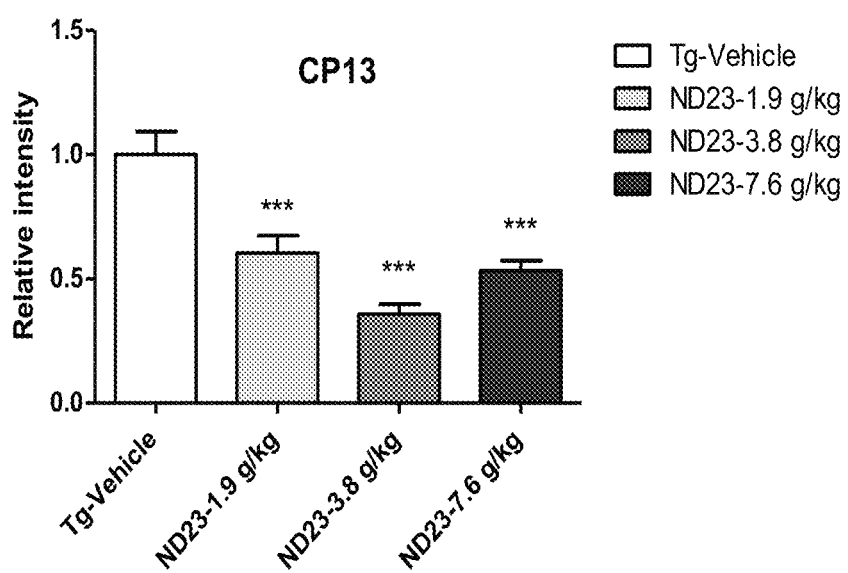
FIG. 19E shows the quantitative analysis of the ND23 treated 3XTg-AD animal's insoluble tau levels are detected using CP13 antibodies.
Figure 19F:
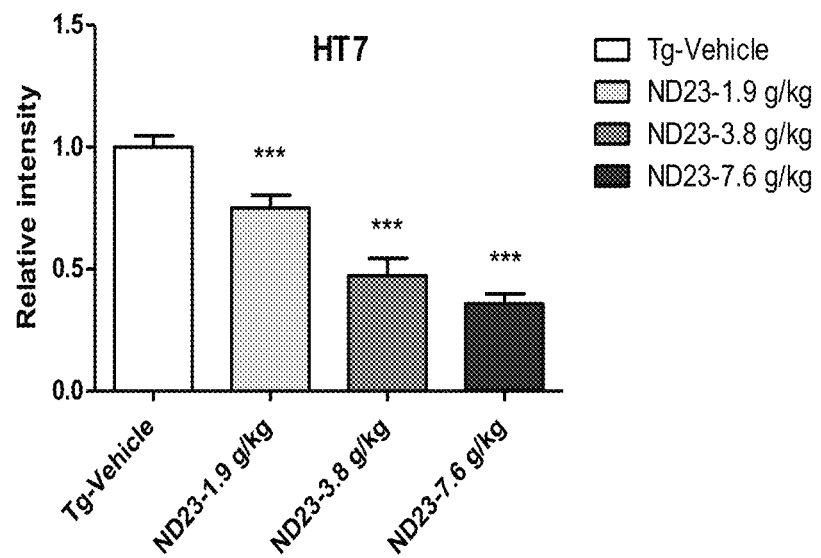
FIG. 19F shows the quantitative analysis of the ND23 treated 3XTg-AD animal's insoluble tau levels are detected using HT7 antibodies.
Figure 19G:
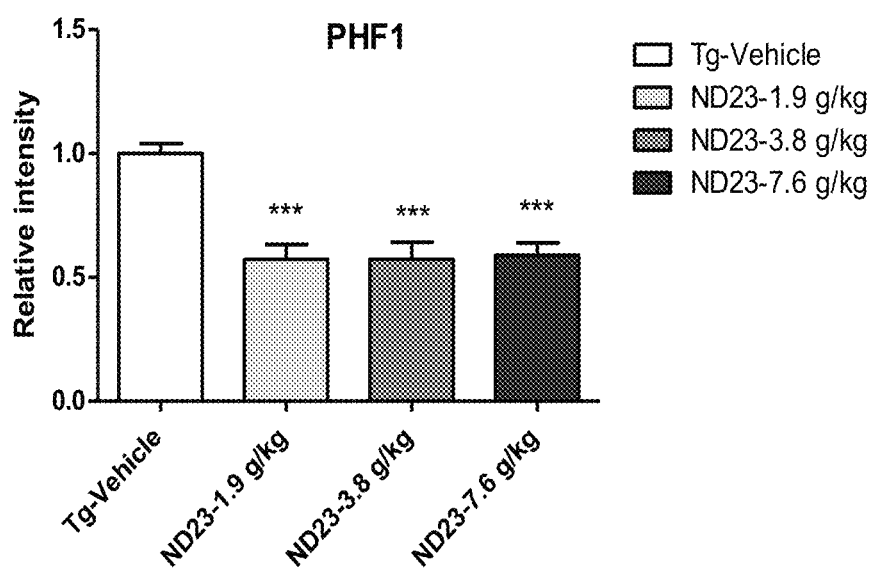
FIG. 19G shows the quantitative analysis of the ND23 treated 3XTg-AD animal's insoluble tau levels are detected using PHF1 antibodies
Figure 20A:
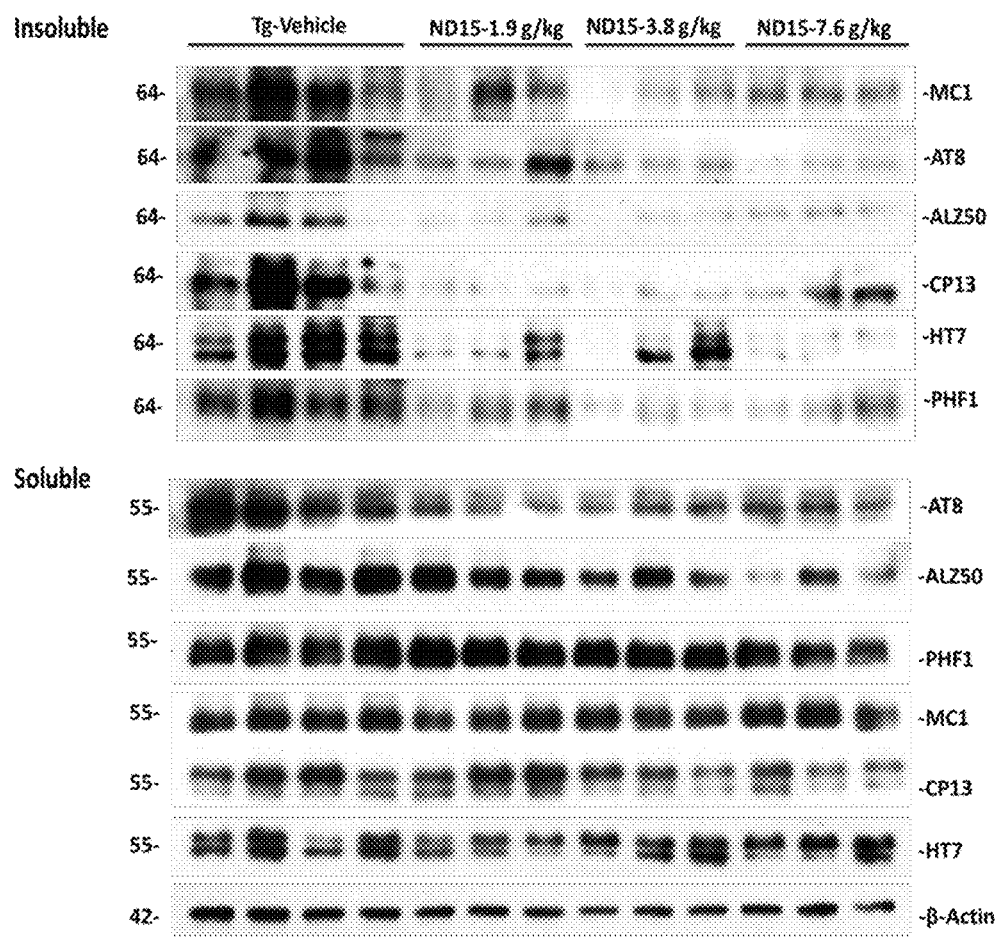
FIG. 20A shows ND15 reduced the levels of insoluble phosphorylated, misfolded and total tau in 3XTg-AD mice by western blot.
Figure 20B:
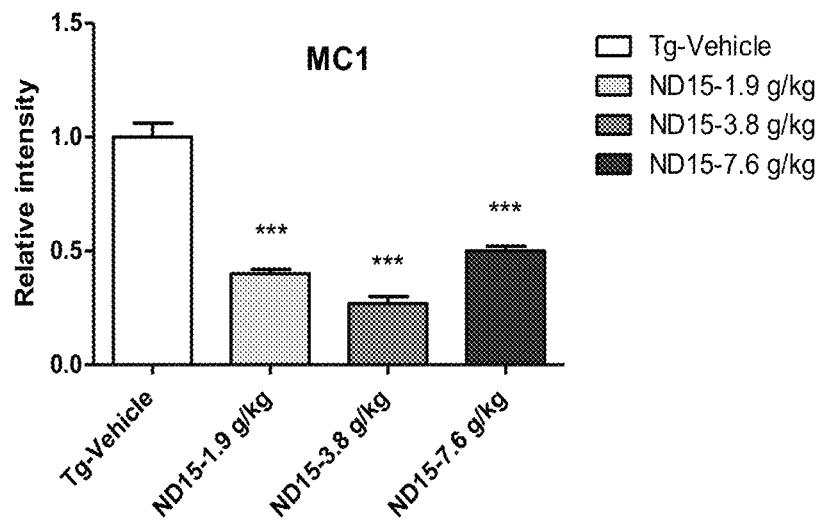
FIG. 20B shows the quantitative analysis of the ND15 treated 3XTg-AD animal's insoluble tau levels are detected by MC1 antibodies.
Figure 20C:
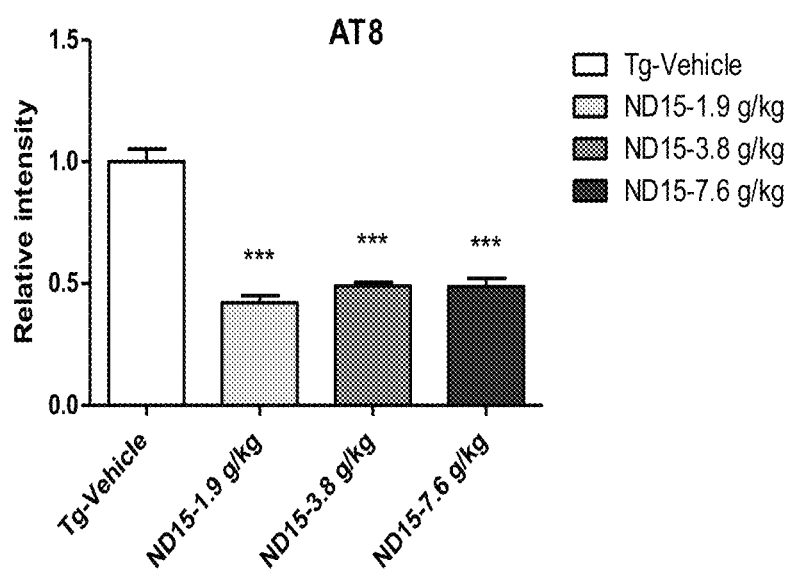
FIG. 20C shows the quantitative analysis of the ND15 treated 3XTg-AD animal's insoluble tau levels are detected by AT8 antibodies.
Figure 20D:
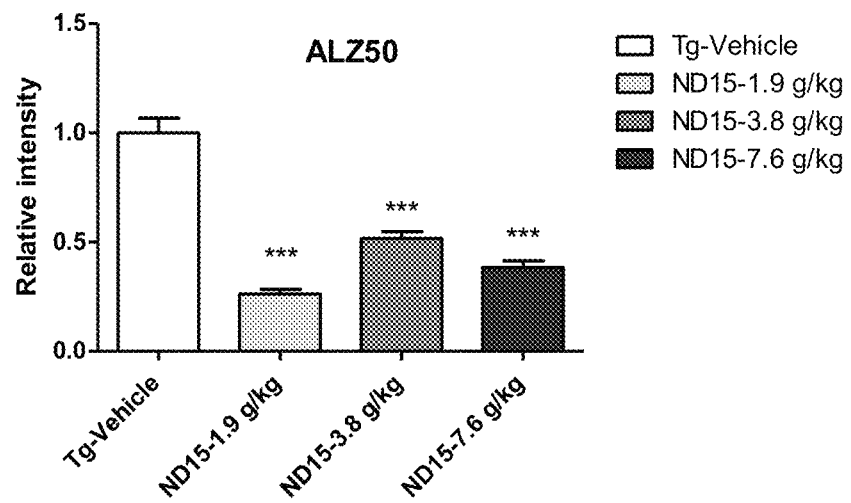
FIG. 20D shows the quantitative analysis of the ND15 treated 3XTg-AD animal's insoluble tau levels are detected by ALZ50 antibodies.
Figure 20E:
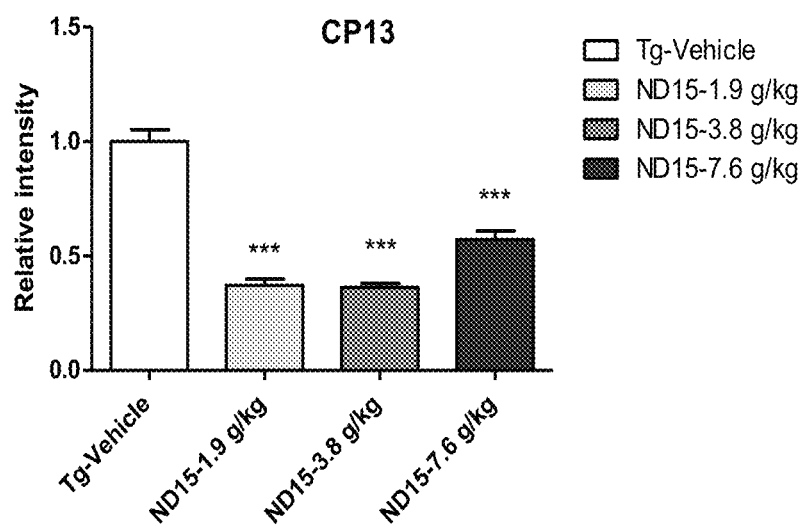
FIG. 20E shows the quantitative analysis of the ND15 treated 3XTg-AD animal's insoluble tau levels are detected by CP13 antibodies.
Figure 20F:
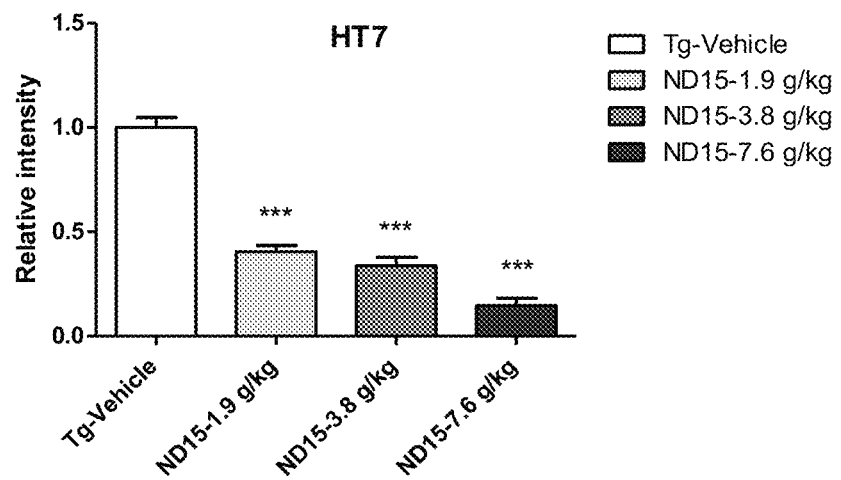
FIG. 20F shows the quantitative analysis of the ND15 treated 3XTg-AD animal's insoluble tau levels are detected by HT7 antibodies.
Figure 20G:
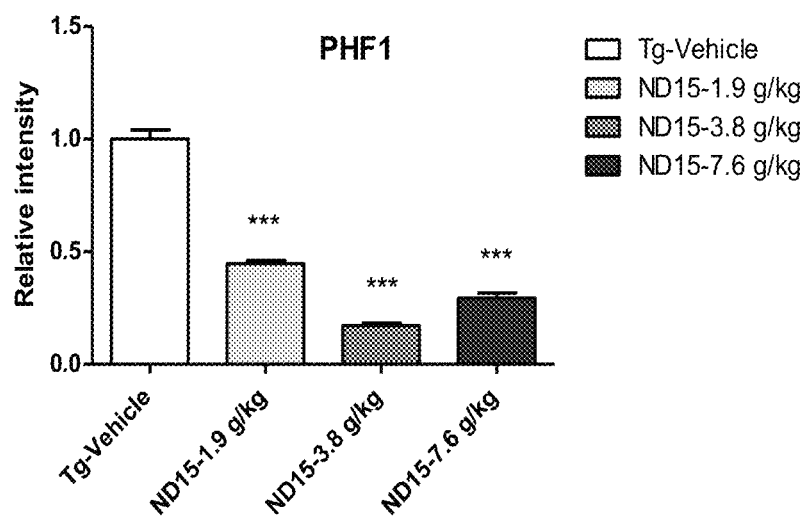
FIG. 20G shows the quantitative analysis of the ND15 treated 3XTg-AD animal's insoluble tau levels are detected by PHF1 antibodies.

To confirm the brain permeability of the active components in these formulas, the inventors carried out the pharmacokinetics experiment in ICR mice for the selected formulas ND1, ND23 and ND15. The inventors performed pharmacokinetics for 8 different time points in both brain and plasma. ICR mice were used in this study to evaluate the brain permeability of the active components in the selected formulas. Each group consists of 3-4 mice. Every mice used in the study were starved overnight and dosed with respective drug orally at 7.6 g/kg for all the time points. The brain and plasma were collected and extracted for the analysis in the LCMS triple quad system. The quantification of 11 active components of the ND formula was done in both brain and plasma. The quantified results of the active components are given in the FIGS. 15-17. The inventors quantified the main bioactive components of ND1 and we analyzed the quantities of the 11 key bioactive small molecules in the brain and plasma of ICR mice (FIGS. 15A-15B). There were some major and minor brain permeable active components present in ND1 extract. The main bioactive components of ND23 were analyzed in the brain and plasma of ICR mice (FIGS. 16A-16B). There were some major and minor brain permeable active components present in ND23 extract and were quantified by pharmacokinetics. Pharmacokinetics of bioactive components of ND15 was analyzed in the brain and plasma of ICR mice (FIGS. 17A-17B). There were some major and minor brain permeable active components present in ND15 extract and were quantified by LC MS triple quad.

ND1, ND23 and ND15 Reduces the Level of Insoluble Phosphorylated, Misfolded and Total Tau in 3Xtg-AD Mice:

In the inventors' preliminary experiments, the inventors performed in vitro studies and found three formulas out of 24 formulas which showed anti-Aβ and anti-Tau activities in in vitro studies. The inventors selected ND1, ND23 and ND15 for in vivo studies in 3XTg mice. The insoluble Tau in the 3XTg mice brain was separated by the differential separation. The soluble and insoluble Tau fraction from 3XTg-AD mice was extracted. The brain sample was first extracted with RIPA buffer. The resulting RIPA fraction was further extracted with 1% Sarkosyl detergent and ultra-centrifuged at 100,000×g for 1 h. The resulting supernatant and pellet were designated as soluble and insoluble tau, respectively. Phosphorylated tau species in both the soluble and insoluble fraction were detected by AT8, CP13, PHF-1 antibody. The misfolded confirmation tau and total tau were detected using MC1, Alz50 and HT7 antibodies. The herbal extract of the present invention is orally administered to 6-months old 3XTg-AD mouse for 8 months. There were no significant differences in phosphorylated, misfolded and total tau in the soluble fraction of ND1, ND23 and ND15-treated groups (1.9, 3.8, 7.6 g/kg/day). However, the phosphorylated, misfolded and total tau were significantly reduced in the Sarkosyl-insoluble fraction of ND1, ND23 and ND15-treated groups but not in the vehicle-treated group (FIGS. 18A-18G), (FIGS. 19A-19G) (FIGS. 20A-20G). Notably, these effects are concomitant with a large reduction of insoluble tau levels confirming the use of ND1, ND23 and ND15 to reduce abnormal Tau aggregation in 3XTg mice.

Figure 21A:
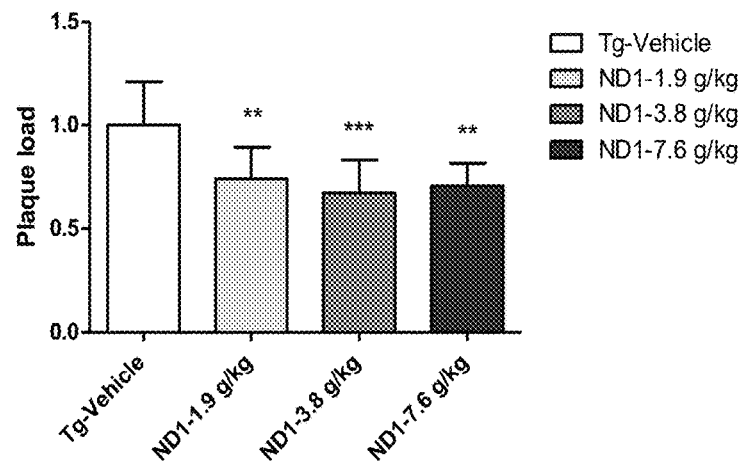
FIG. 21A shows the quantitative analysis of the ND1 treated 3XTg-AD animal's Aβ-plaque load.
Figure 21B:
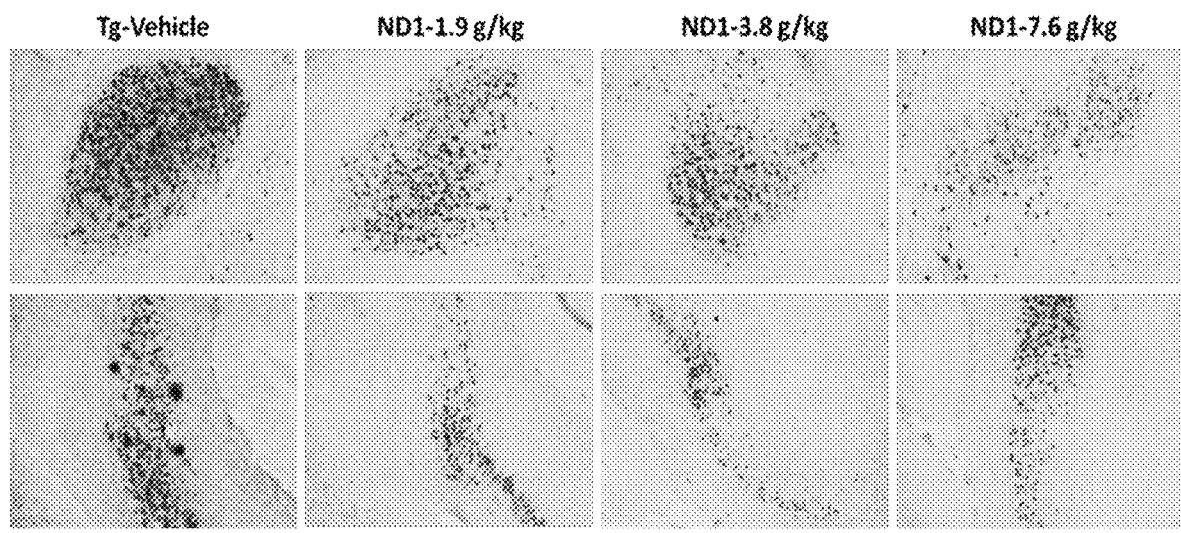
FIG. 21B shows ND1 reduces hippocampal Aβ-plaque burden in 3XTg-AD mice by immunohistochemistry.
Figure 22A:
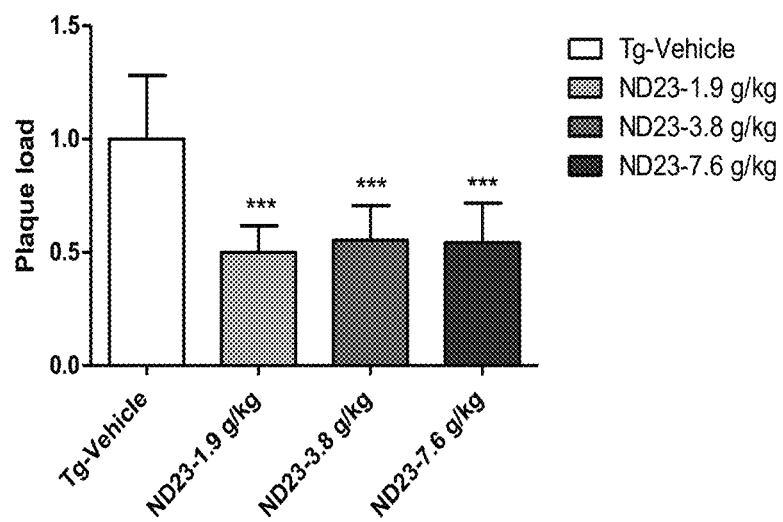
FIG. 22A shows the quantitative analysis of the ND23 treated 3XTg-AD animal's Aβ-plaque load.
Figure 22B:
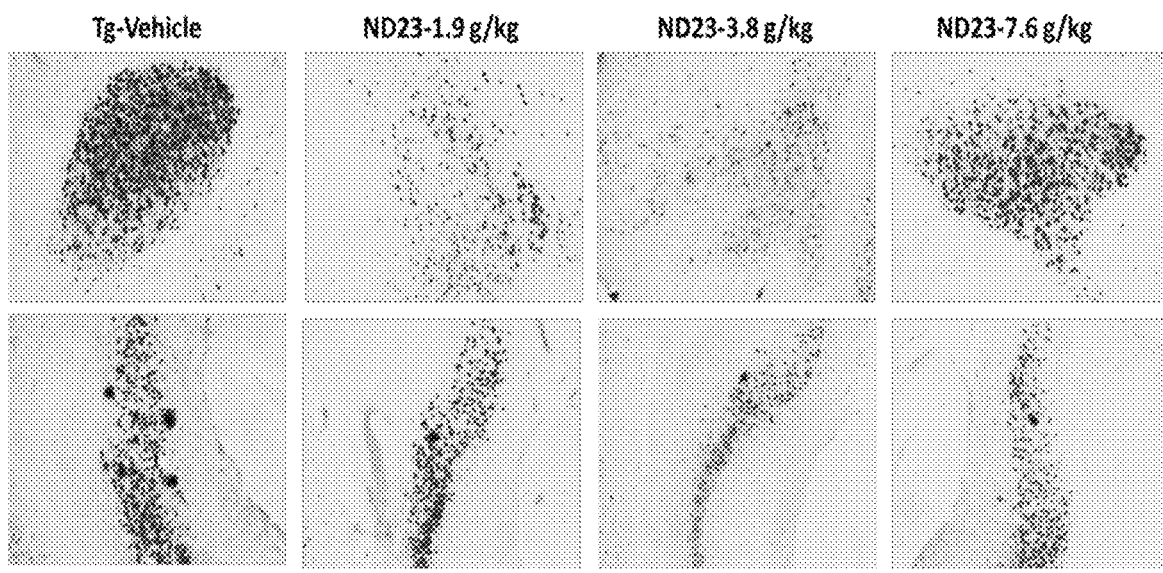
FIG. 22B shows ND23 reduces hippocampal Aβ-plaque burden in 3XTg-AD mice by immunohistochemistry.
Figure 23A:
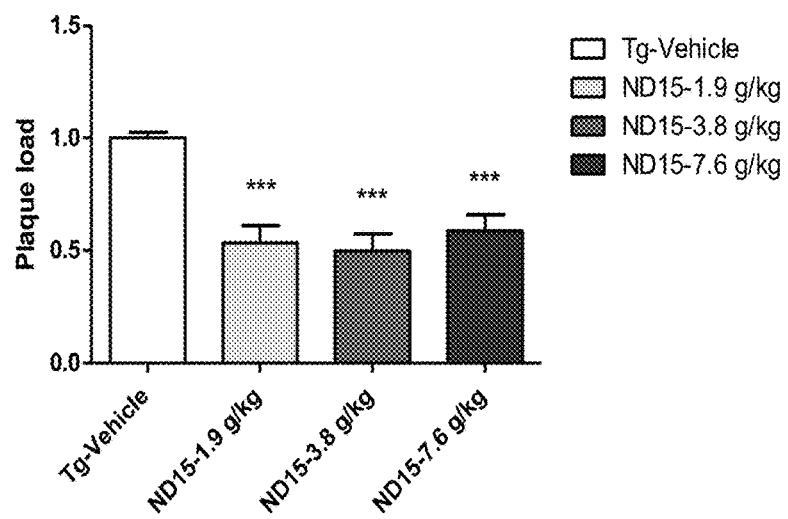
FIG. 23A shows the quantitative analysis of the ND15 treated 3XTg-AD animal's Aβ-plaque load.
Figure 23B:
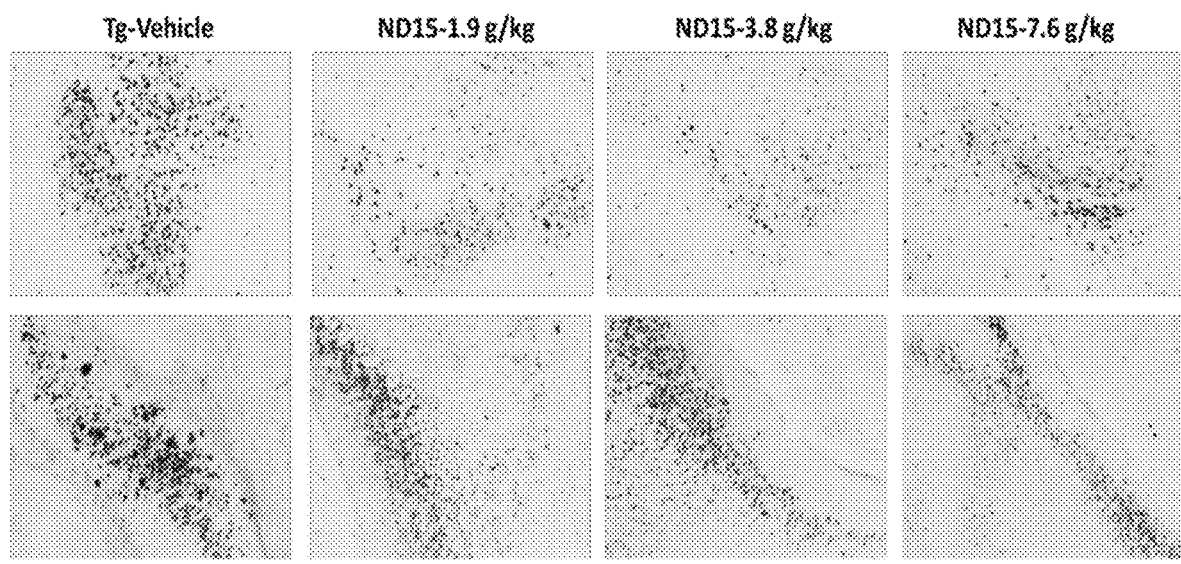
FIG. 23B shows ND15 reduces hippocampal Aβ-plaque burden in 3XTg-AD mice by immunohistochemistry.

ND1, ND23 and ND15 Reduces the Level of Aβ Plaque Load in 3Xtg-AD Mice:

The inventors further investigated Anti-AD effect and bioactivity of ND1, ND23 and ND15 in vivo to test the long-term effect of ND1, ND23 and ND15 (1.9, 3.8, 7.6 g/kg/day) on the Aβ reduction; the inventors carried out studies in 3XTg-AD mouse model. The herbal extract of the present invention is orally administered to 6-months old 3XTg-AD mouse for 8 months. To further confirm the Aβ-plaque pathology, the inventors performed immunohistochemistry in the 30 μm brain slices at different regions namely anterior, medial and posterior. ND1, ND23 and ND15 reduces hippocampal Aβ-plaque burden in brain significantly and dose-dependently compared to the Tg-Vehicle group. These in vivo data confirm the use of ND1, ND23 and ND15 to reduce Tau pathology and Aβ pathology in 3XTg-AD mouse model. ND1, ND23 and ND15 reduces hippocampal Aβ-plaque burden of brain in dose dependent manner and the quantification of the 4G8 positive Aβ-plaque was assessed by Image J software (FIGS. 21A-21B), (FIGS. 22A-22B) (FIGS. 23A-23B).

Figure 24A:
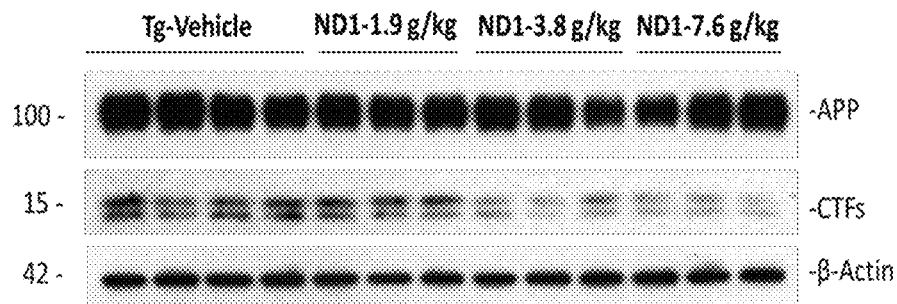
FIG. 24A shows ND1 reduced the levels of CTFs in brain homogenates of 3XTg-AD mice by western blot
Figure 24B:
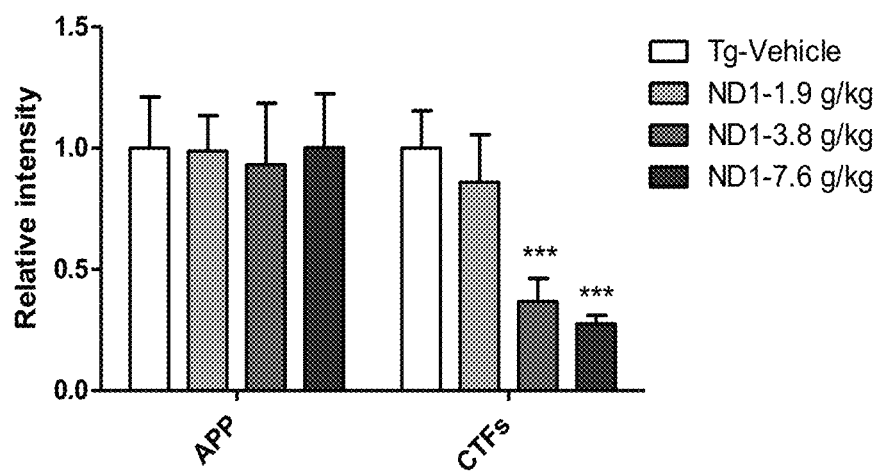
FIG. 24B shows the quantitative analysis of the ND1 treated 3XTg-AD animal's APP and CTFs levels.
Figure 25A:
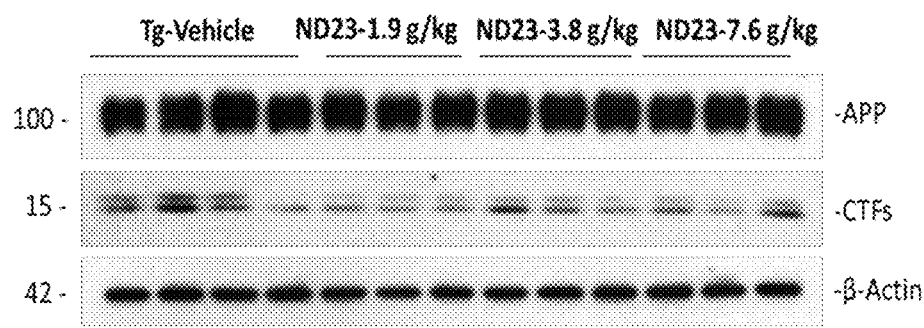
FIG. 25A shows ND23 reduced the levels of CTFs in brain homogenates of 3XTg-AD mice by western blot
Figure 25B:
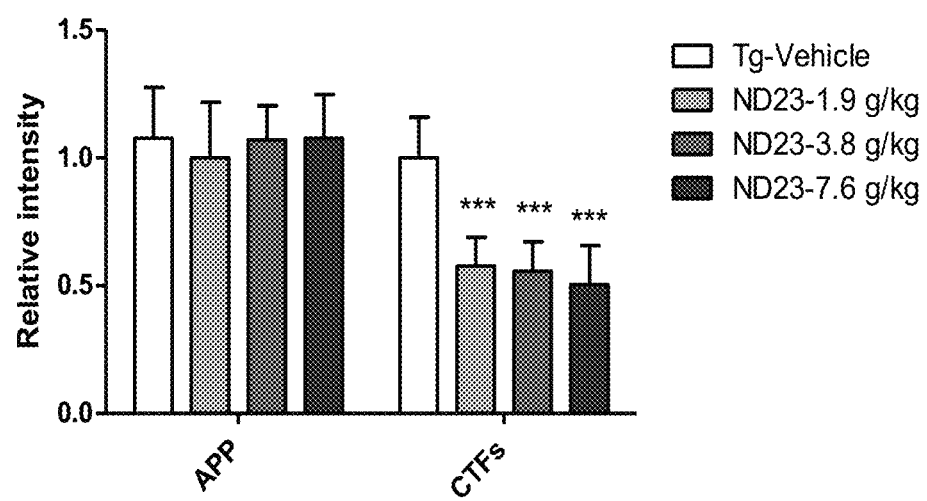
FIG. 25B shows the quantitative analysis of the ND23 treated 3XTg-AD animal's APP and CTFs levels.
Figure 26A:
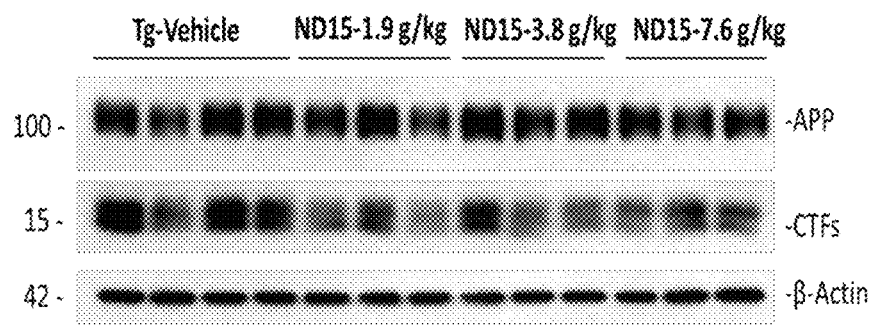
FIG. 26A shows ND15 reduced the levels of CTFs in brain homogenates of 3XTg-AD mice by western blot
Figure 26B:
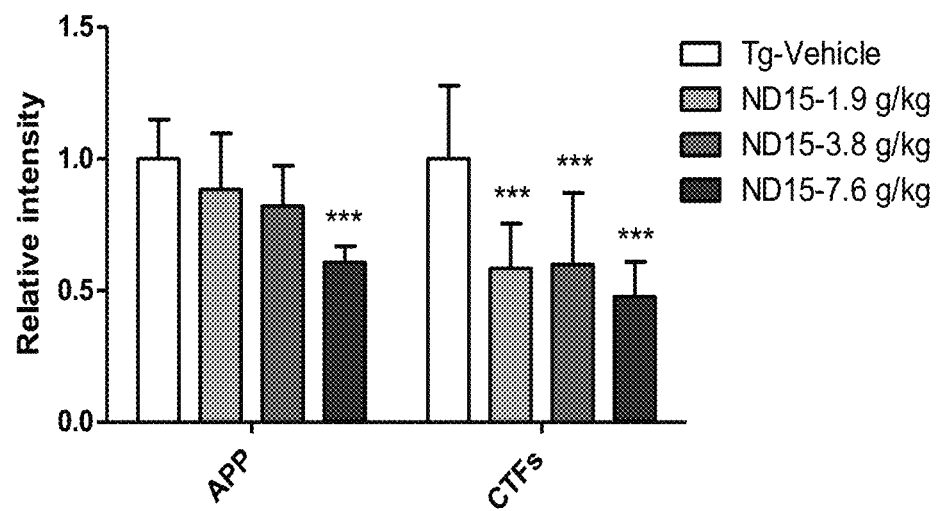
FIG. 26B shows the quantitative analysis of the ND15 treated 3XTg-AD animal's APP and CTFs levels.

ND1, ND23 and ND15 Reduces the Level of APP Processing in 3XTg-AD Mice:

The inventors further investigated Anti-AD effect and bioactivity of ND1, ND23 and ND15 in vivo to test the long-term effect of ND1, ND23 and ND15 (1.9, 3.8, 7.6 g/kg/day) on the Aβ reduction; the inventors carried out studies in 3XTg-AD mouse model. The herbal extract of the present invention is orally administered to 6-months old 3XTg-AD mouse for 8 months. Further, the inventors performed the western blot analysis with the brain homogenate, the treatment with ND1, ND23 and ND15 (1.9, 3.8, 7.6 g/kg/day) significantly and dose-dependently reduced the levels CTFs in brain homogenates (FIGS. 24A-24B), (FIGS. 25A-25B) (FIGS. 26A-26B). ND1, ND23 and ND15 reduce the levels of CTFs in dose dependent manner and the quantification of the APP and CTFs was assessed by Image J software. These in vivo data confirms the use of ND1, ND23 and ND15 to reduce Tau pathology and Aβ pathology in 3XTg-AD mouse model.

ND1, ND23 and ND15 Treatment Mitigates Tau Pathology in 3XTg-AD Mice

Figure 27A:
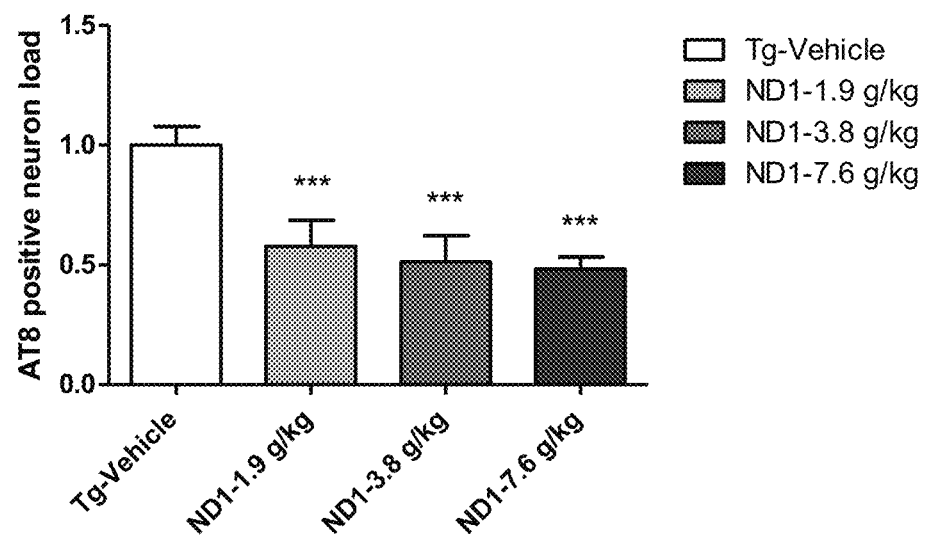
FIG. 27A shows the quantitative analysis of the ND1 treated 3XTg-AD animal's AT8 positive NFT load were assessed by Image J software.
Figure 27B:
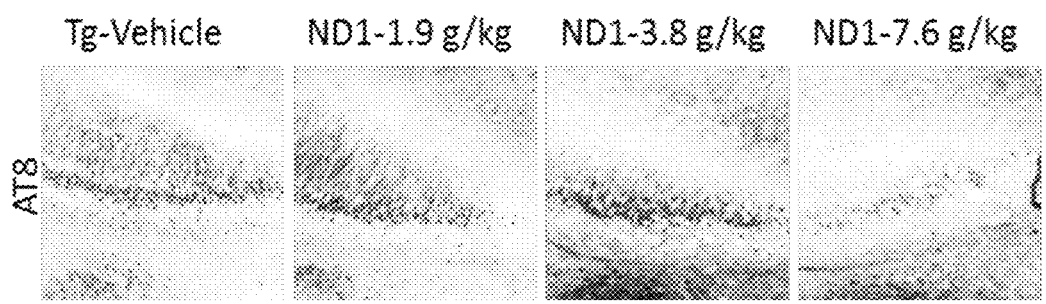
FIG. 27B shows ND1 (1.9, 3.8, 7.6 g/kg/day) reduces the AT8 positive neuron load in 3XTg-AD mice by immunohistochemistry.
Figure 28A:
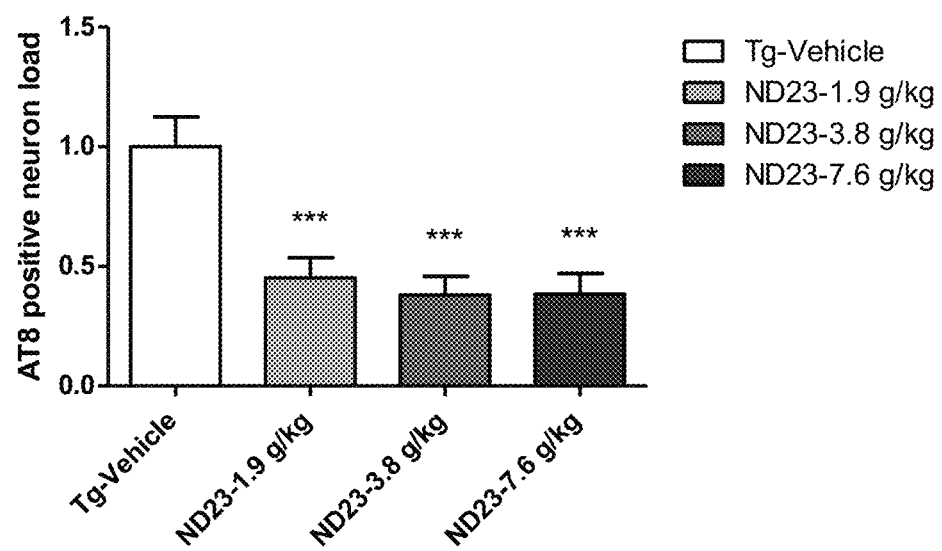
FIG. 28A shows the quantitative analysis of the ND23 treated 3XTg-AD animal's AT8 positive NFT load were assessed by Image J software.
Figure 28B:
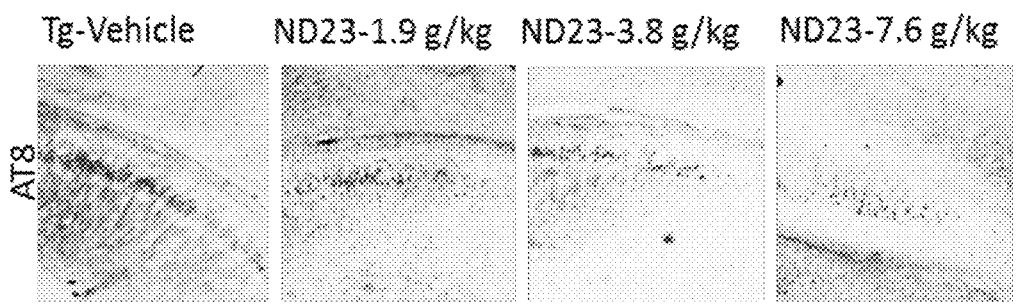
FIG. 28B shows ND23 (1.9, 3.8, 7.6 g/kg/day) reduces the AT8 positive neuron load in 3XTg-AD mice by immunohistochemistry.
Figure 29A:
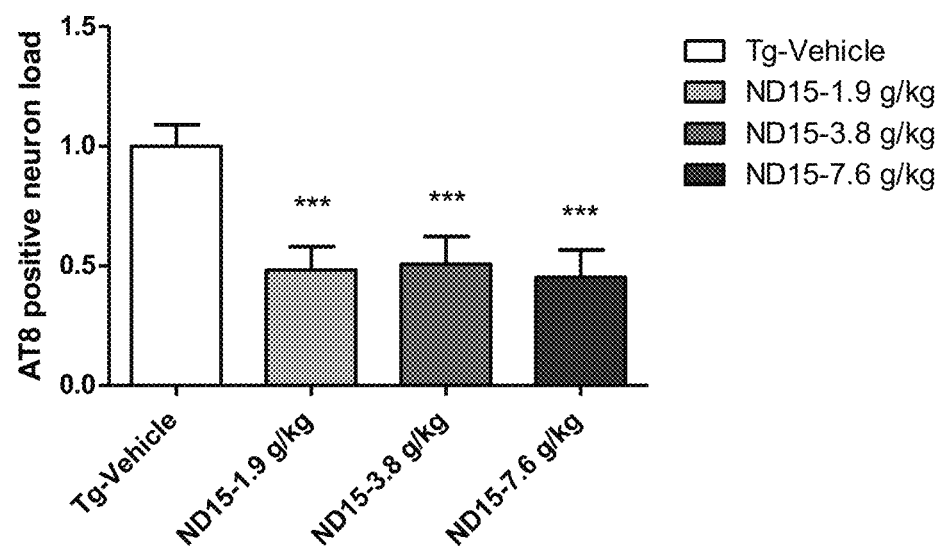
FIG. 29A shows the quantitative analysis of the ND15 treated 3XTg-AD animal's AT8 positive NFT load were assessed by Image J software.
Figure 29B:
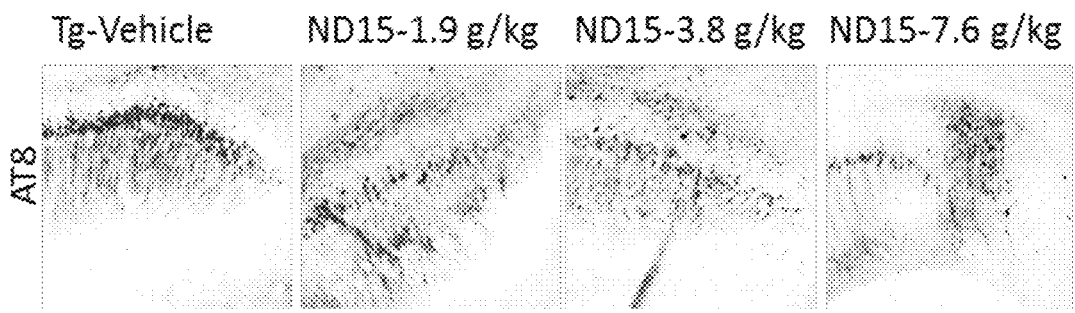
FIG. 29B shows ND15 (1.9, 3.8, 7.6 g/kg/day) reduces the AT8 positive neuron load in 3XTg-AD mice by immunohistochemistry.

To assess tau pathology in the brains of 3XTg-AD mice, the inventors used AT8 monoclonal antibodies to assess the insoluble tau pathology load in the brain by immunohistochemistry. The epitope of AT8 is located outside the region of internal repeats of microtubule binding domains (RT1-4) and requires the phosphorylation of Se96/Ser404. Immunostaining of AT8-positive neurons in the brains of 3XTg-AD mice revealed the insoluble tau pathology load and neuro fibrillary tangles load. To further confirm the Anti-Tau pathology, the inventors performed immunohistochemistry in the 30 μm brain slices at different regions namely anterior, medial and posterior. ND1, ND23 and ND15 reduce hippocampal neuro fibrillary tangles load in brain significantly and dose-dependently compared to the Tg-Vehicle group. These in vivo data confirms use of ND1, ND23 and ND15 to reduce Tau pathology in 3XTg-AD mouse model. ND1, ND23 and ND15 reduces hippocampal insoluble tau pathology load and neuro fibrillary tangles burden of brain in dose dependent manner and the quantification of the AT8 positive neuron load was assessed by Image J software (FIGS. 27A-27B), (FIGS. 28A-28B) (FIGS. 29A-29B). Altogether, these results demonstrate use of ND1, ND23 and ND15 to reduce Tau pathology in 3XTg-AD mouse model.

Blood Biochemistry Test for the Sub-Chronic Toxicity of ND1, ND23 and ND15 in WT Mice:

Further the inventors carried out the sub-chronic toxicity of ND1, ND23 and ND15 in wild type C57BL/6 mice. At the end of 28 days the animals were euthanized and the blood plasma was collected and stored at −80° C. Blood biochemistry tests were conducted for detecting if ND1, ND23 and ND15 affect the function of liver, kidney and heart. Further the alanine aminotransferase (ALT), aspartate aminotransferase (AST) activities, blood urea nitrogen (BUN), creatinine (Cr), total protein, albumin and globulin contents were tested using commercial kits. The biochemical constituents of the blood plasma were assessed for the ND1, ND23 and ND15 (1.9, 3.8, 7.6 g/kg/day) treated groups. Quantified results of the biochemical constituents of the blood plasma of ND1, ND23 and ND15 (1.9, 3.8, 7.6 g/kg/day) treated groups were assessed and tabulated in the tables (FIGS. 30A-30C).

ND Treatment Mitigates Neuroinflammation in 3XTg-AD and 5XFAD Mice.

Figure 31A:
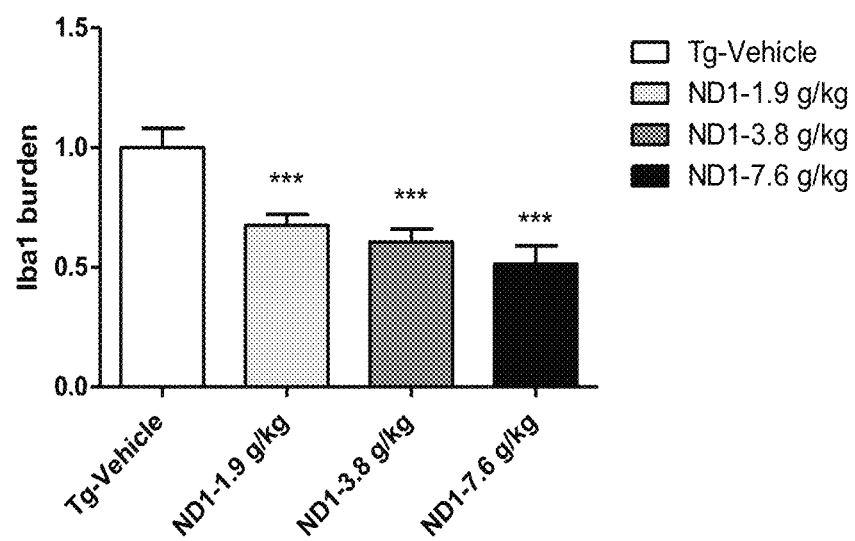
Figure 31B:
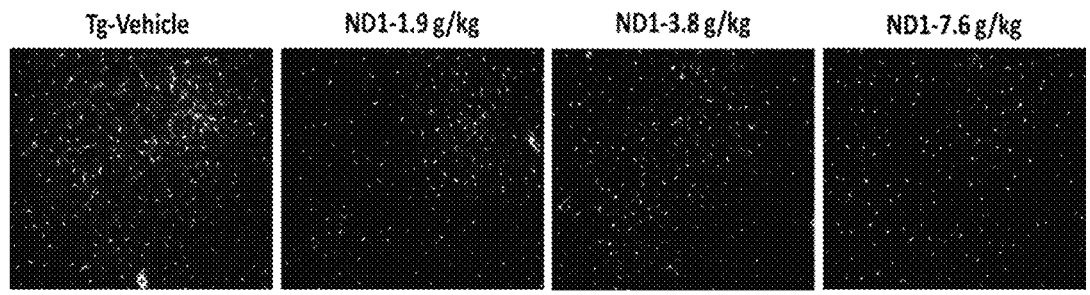
Figure 32A:
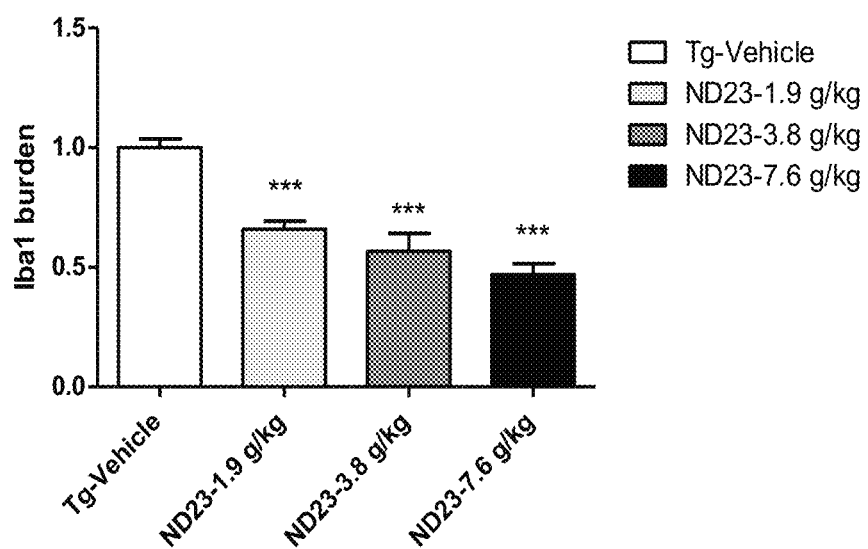
Figure 32B:
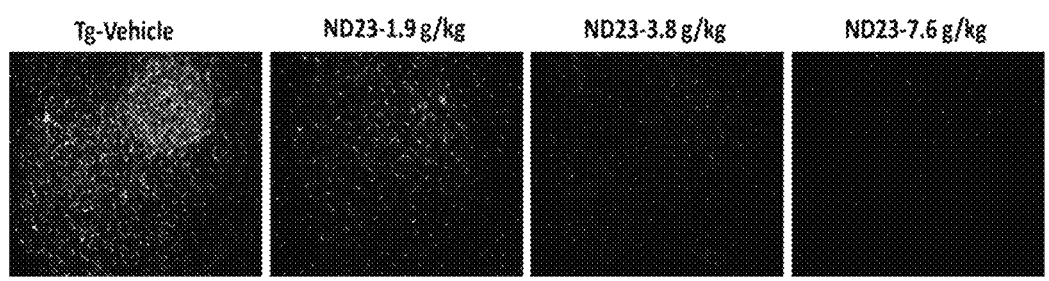
Figure 33A:
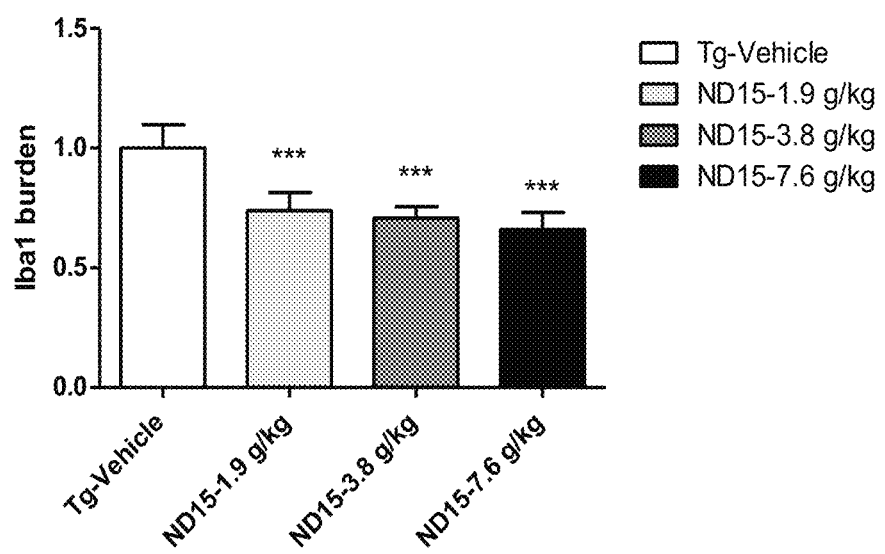
Figure 33B:
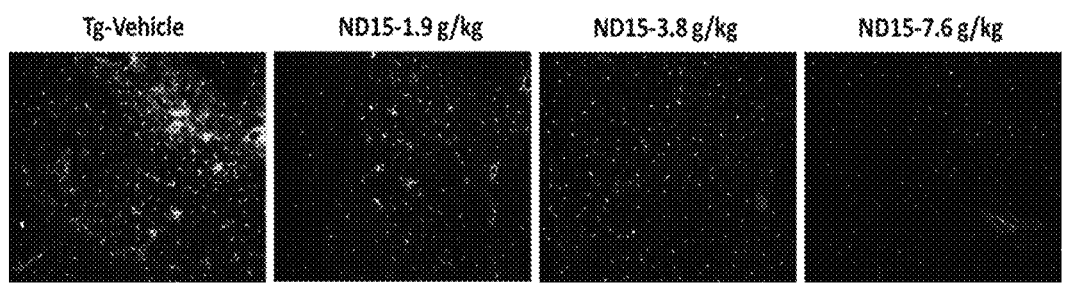

Further we investigated whether ND1, ND23 and ND15 (1.9, 3.8, 7.6 g/kg/day) reduces neuroinflammation in 3XTg-AD mice. The herbal extract of the present invention is orally administered to 6-months old 3XTg-AD mouse for 8 months. As activated microglial cells and reactive astrocytes are closely associated with neurofibrillary tangles and Aβ pathology. Expression of ionized calcium binding adapter molecule 1 (Iba-1) (microgliosis) is evaluated to identify the condition of neuroinflammation in ND1, ND23 and ND15 (1.9, 3.8, 7.6 g/kg/day) treated 3XTg-AD mice. Immunostaining of Iba-1-positive cells in the brain slice of 3XTg-AD mice revealed that ND1, ND23 and ND15 (1.9, 3.8, 7.6 g/kg/day) treatment decrease reactive Iba-1 positive cell count in dose dependent manner compared to the Tg-vehicle-treated group of 3XTg-AD mice (FIGS. 31A-31B), (FIGS. 32A-32B), (FIGS. 33A-33B).

Figure 34A:
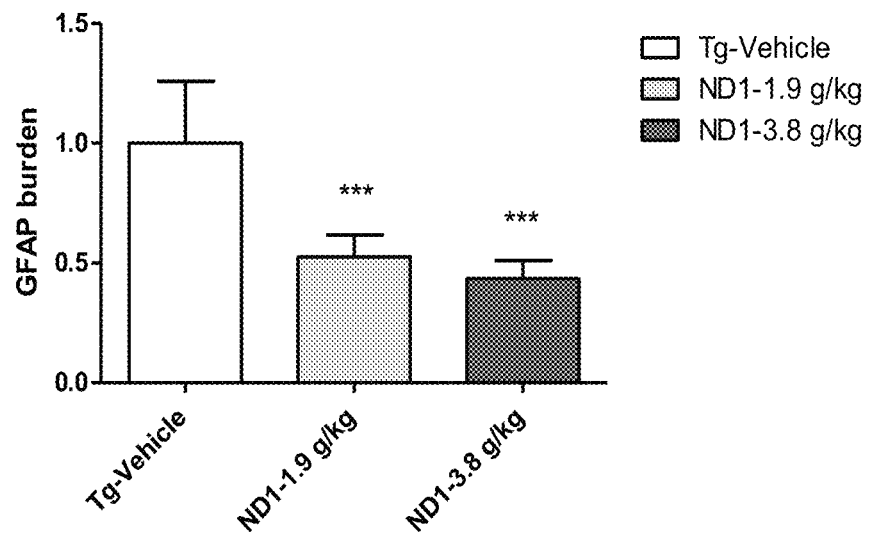
Figure 34B:
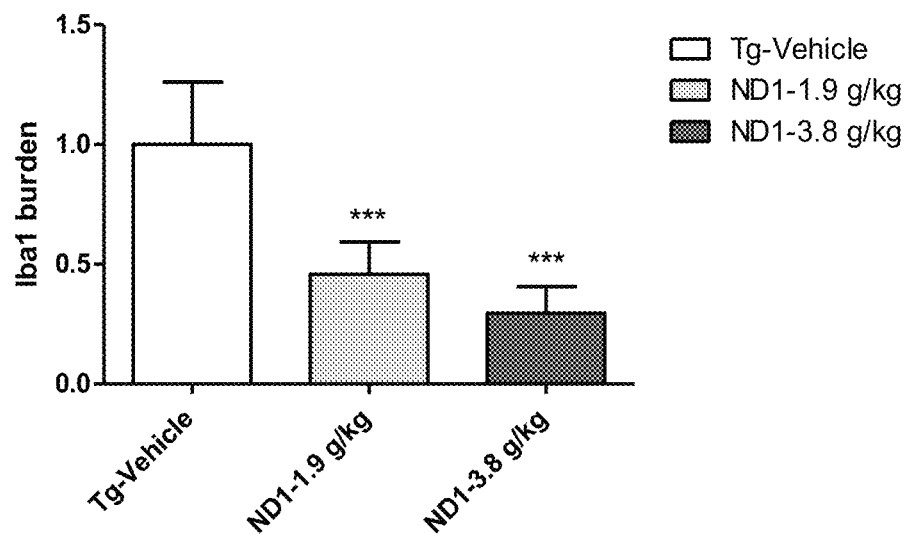
Figure 34C:
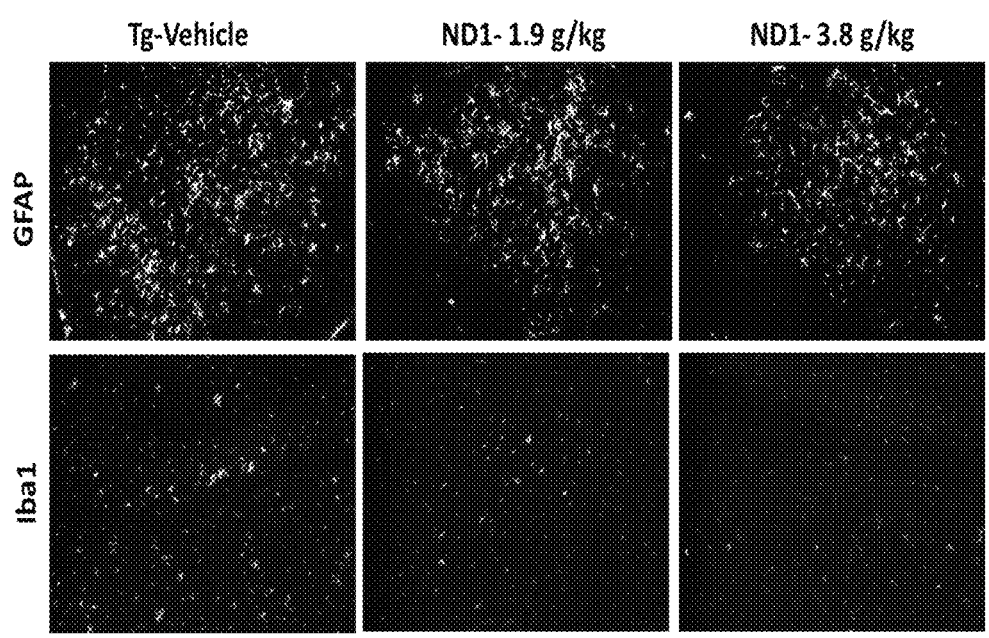
Figure 35A:
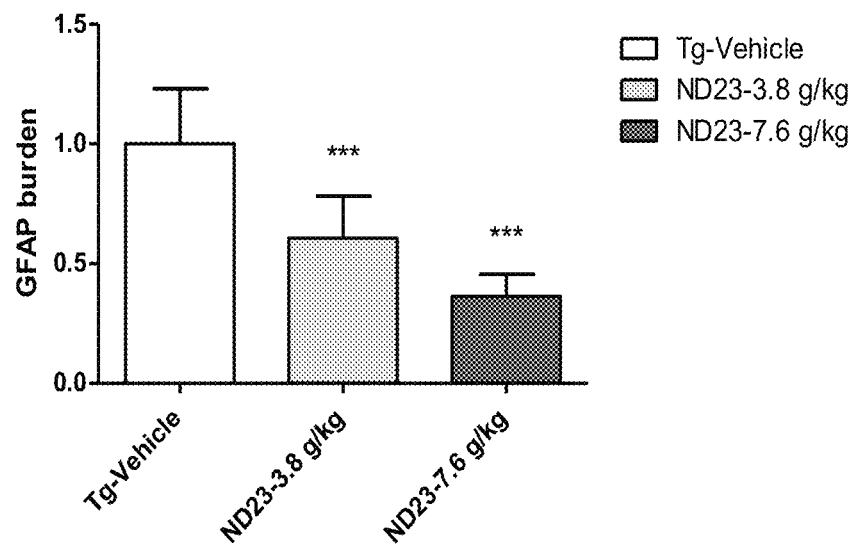
Figure 35B:
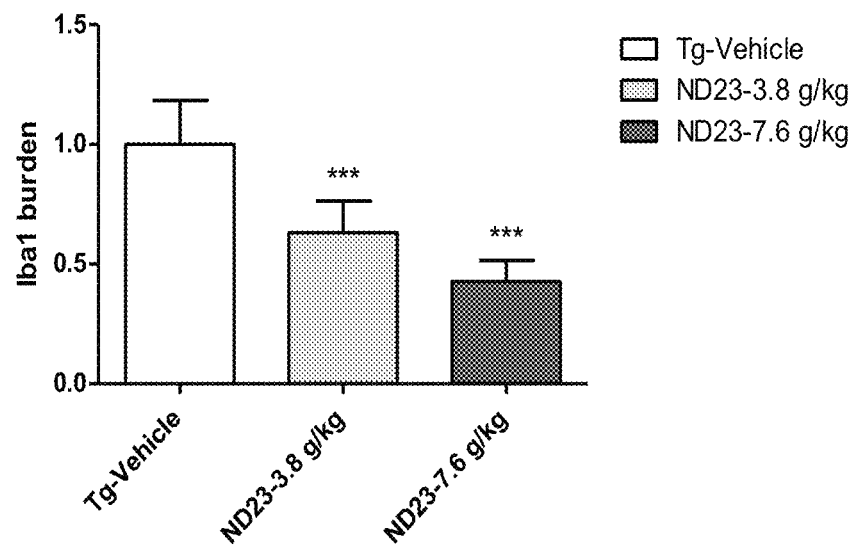
Figure 35C:
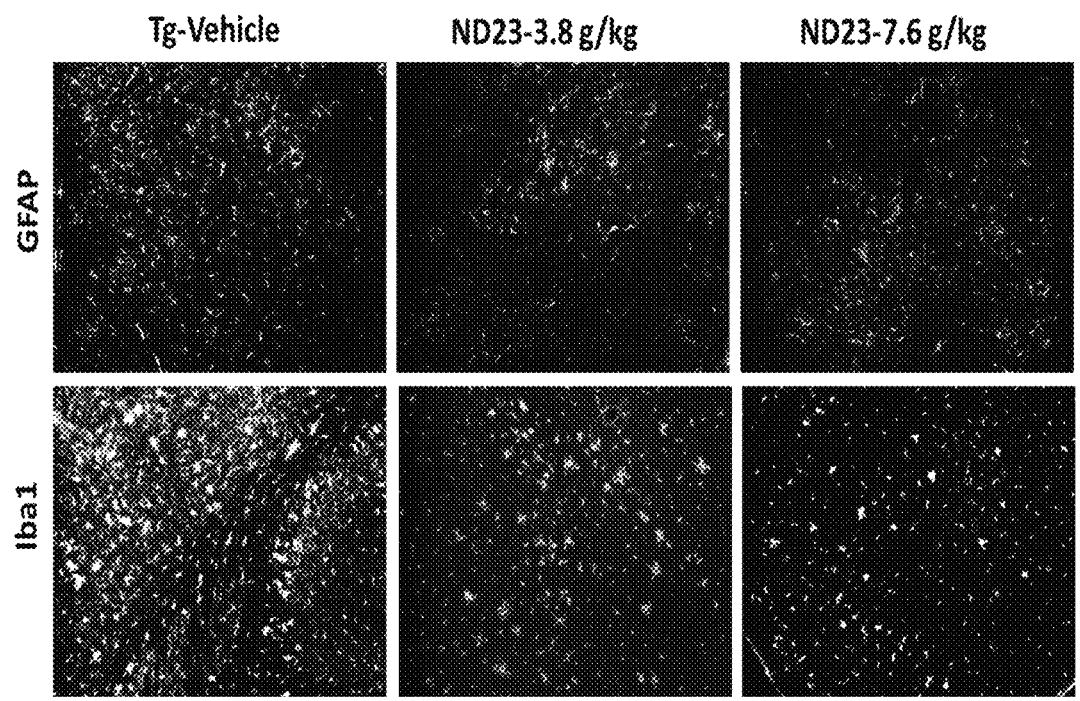

To further confirm the above results, we investigated activated microglial cells and reactive astrocytes in the brain slices of 5XFAD mice model. The herbal extract of the present invention is orally administered to 6-months old 3XTg-AD mouse for 8 months. To evaluate the neuroinflammation, we performed immunohistochemistry in the 30 μm brain slices at different regions namely anterior, medial and posterior. As activated microglial cells and reactive astrocytes are closely associated with neurofibrillary tangles and Aβ pathology. Expression of ionized calcium binding adapter molecule 1 (Iba-1) (microgliosis) and glial fibrillary acidic protein (GFAP) (astrocytosis) are evaluated to identify the situation of neuroinflammation in ND1 and ND23 treated 5XFAD mice. Immunostaining of Iba-1 and GFAP in the brain slices of 5XFAD mice revealed that ND1 and ND23 treatment decrease activated GFAP and reactive Iba-1 positive cell count in dose dependent manner compared to the Tg-vehicle-treated group of 5XFAD mice (FIGS. 34A-34C), (FIGS. 35A-35C). Putting together, these results demonstrate that ND1, ND23 and ND15 have the potential to reduce neuroinflammation in 3XTg-AD and 5XFAD mouse model.

CONCLUSION

The present invention provides composition comprising a extract of Huanglian, Huangbai, Zhizi, Danshen, Gouteng and Yanhusuo and use of the composition for the treatment of AD. The present composition is shown to reduce Tau pathology and Aβ pathology, as demonstrated in vitro and in vivo studies. The inventors' study reveals for the first time that oral feed admixture of the present composition reduces Tau pathology and Aβ pathology and enhances memory retention function in 5XFAD and 3XTg-AD mice, respectively. In a preferred embodiment, formula ND1, ND23 and ND15 reduce Tau pathology and Aβ pathology and enhances memory retention function in mice models. Moreover, the inventors have shown that the active components of the present composition are brain permeable by crossing the blood-brain barrier. Not only can the active components reach the brain, the ND also possess a peripheral mode of therapy. In another embodiment. the present composition is formulated to health food supplement or medicaments to prevent or remedy AD. In another embodiment, the use of the present composition to treat Alzheimer's disease is provided.

INDUSTRIAL APPLICABILITY

This invention provides a herbal composition with significant potent therapeutic effects for treating neurodegenerative diseases by targeting both amyloid-β (Aβ) and tau-associated neurofibrillary tangles (NFTs).

What we claim:

1. A herbal composition comprising a herbal extract of:
Huanglian,
Huangbai,
ZhiZi,
Yanhusuo,
Danshen, and
Gouteng
wherein the herbal extract comprises said Huanglian, Huangbai, ZhiZi, Yanhusuo, Danshen and Gouteng in the weight ratios of 0.83-4.15:1.66-3.46:1.53-4.16:2.69-2.91: 4.57-6.22:4.22-6.24, respectively.

2. The herbal composition according to claim 1, wherein the herbal extract comprises Huanglian, Huangbai, ZhiZi, Yanhusuo, Danshen and Gouteng in a weight ratio of 0.83: 1.66: 4.16: 2.91: 4.57: 6.24.

3. A pharmaceutical composition for treating neurodegenerative diseases caused by amyloid-β (Aβ) and tau-associated neurofibrillary tangles comprising the herbal composition according to claim 2.

4. The pharmaceutical composition according to claim 3 wherein the pharmaceutical composition is in oral form.

5. The pharmaceutical composition according to claim 3 wherein the neurodegenerative diseases caused by amyloid-β (Aβ) and tau-associated neurofibrillary tangles in human comprising Alzheimer's disease.

6. The herbal composition according to claim 1, wherein the herbal extract comprises Huanglian, Huangbai, ZhiZi, Yanhusuo, Danshen and Gouteng in a weight ratio of 4.15: 3.46: 3.46: 2.76: 6.22: 6.22.

7. A pharmaceutical composition for treating neurodegenerative diseases caused by amyloid-β (Aβ) and tau-associated neurofibrillary tangles comprising the herbal composition according to claim 6.

8. The pharmaceutical composition according to claim 7 wherein the pharmaceutical composition is in oral form.

9. The pharmaceutical composition according to claim 7 wherein the neurodegenerative diseases caused by amyloid-β (Aβ) and tau-associated neurofibrillary tangles in human comprising Alzheimer's disease.

10. The herbal composition according to claim 1, wherein the herbal extract comprises Huanglian, Huangbai, ZhiZi, Yanhusuo, Danshen and Gouteng in a weight ratio of 3.45: 1.92: 1.53: 2.69: 5.76: 4.22.

11. A pharmaceutical composition for treating neurodegenerative diseases caused by amyloid-β (Aβ) and tau-associated neurofibrillary tangles comprising the herbal composition according to claim 1.

12. The pharmaceutical composition according to claim 11 wherein the pharmaceutical composition is in oral form.

13. The pharmaceutical composition according to claim 11 wherein the neurodegenerative diseases caused by amyloid-β (Aβ) and tau-associated neurofibrillary tangles in human comprising Alzheimer's disease.

14. A method of treating neurodegenerative diseases caused by amyloid-β (Aβ) and tau-associated neurofibrillary tangles in human comprising administering the composition according to claim 1, wherein said composition is administered in a dosage from 0.154 g of said herbal extract per kg of a subject per day to 0.617 g of said herbal extract per kg of a subject per day.

15. The method of claim 14, wherein said composition is administered orally.

16. The method of claim 14, wherein the neurodegenerative diseases comprise Alzheimer's disease.

* * * * *